(12) United States Patent
Rossello et al.

(10) Patent No.: US 9,617,213 B2
(45) Date of Patent: Apr. 11, 2017

(54) SYNTHETIC ANALOGUES OF XANTHOHUMOL

(71) Applicants: UNIVERSITA' DI PISA, Pisa (PI) (IT); AZIENDA OSPEDALIERA ARCISPEDALE SANTA MARIA NUOVA / IRCCS ISTITUTO IN TECNOLOGIE AVANZATE E MODELLI ASSISTENZIALI IN ONCOLOGIA, Reggio Emilia (RE) (IT)

(72) Inventors: Armando Rossello, Pisa (IT); Elisa Nuti, Pisa (IT); Elisabetta Orlandini, Pisa (IT); Susanna Nencetti, Pisa (IT); Adriana Albini, Reggio Emilia (IT); Anna Rita Cantelmo, Milan (IT); Desiree Bartolini, Reggio Emilia (IT); Douglas M. Noonan, Varese (IT); Cristina Gallo, Reggio Emilia (IT)

(73) Assignees: UNIVERSITA' DI PISA, Pisa (IT); Azienda Ospedaliera Arcispedale Santa Maria Nuova/IRCCS Instituto in Tecnologie Avanzate e Modelli Assistenziali in Oncologia, Reggio Emilia (IT)

( * ) Notice: Subject to any disclaimer, the term of this patent is extended or adjusted under 35 U.S.C. 154(b) by 0 days.

(21) Appl. No.: 14/782,623

(22) PCT Filed: Apr. 7, 2014

(86) PCT No.: PCT/IB2014/060496
§ 371 (c)(1),
(2) Date: Oct. 6, 2015

(87) PCT Pub. No.: WO2014/167481
PCT Pub. Date: Oct. 16, 2014

(65) Prior Publication Data
US 2016/0075652 A1  Mar. 17, 2016

(30) Foreign Application Priority Data
Apr. 8, 2013 (IT) .............................. MI2013A0536

(51) Int. Cl.
| | | |
|---|---|---|
| C07D 213/50 | (2006.01) |
| C07C 205/45 | (2006.01) |
| C07C 311/29 | (2006.01) |
| C07C 49/84 | (2006.01) |
| C07D 213/61 | (2006.01) |
| C07D 311/58 | (2006.01) |
| C07C 311/08 | (2006.01) |
| C07C 311/51 | (2006.01) |
| C07C 233/33 | (2006.01) |
| C07C 205/61 | (2006.01) |
| C07C 233/55 | (2006.01) |
| C07D 311/04 | (2006.01) |

(52) U.S. Cl.
CPC ............ *C07D 213/50* (2013.01); *C07C 49/84* (2013.01); *C07C 205/45* (2013.01); *C07C 205/61* (2013.01); *C07C 233/33* (2013.01); *C07C 233/55* (2013.01); *C07C 311/08* (2013.01); *C07C 311/29* (2013.01); *C07C 311/51* (2013.01); *C07D 213/61* (2013.01); *C07D 311/04* (2013.01); *C07D 311/58* (2013.01)

(58) Field of Classification Search
CPC ...... A61K 31/00; C07C 49/54; C07C 205/45; C07C 205/61; C07D 213/50; C07D 213/61; C07D 311/04; C07D 311/58; A01B 12/00
See application file for complete search history.

(56) References Cited

U.S. PATENT DOCUMENTS 9,290,427 B2 * 3/2016 Bracke .................. A61K 31/12
2008/0233221 A1 * 9/2008 Ho ....................... A61K 36/899
424/750

OTHER PUBLICATIONS

Dietz et al. Xanthohumol Isolated from Humulus Iupulus Inhibits Menadione-Induced DNA Damage through Induction of Quinone Reductase. Chem. Res. Toxicol. vol. 18, 2005, 1296-1305.*
Mukherjee et al. Synthetic and Biological Activity Evaluation Studies on Novel 1,3-Diarylpropanes. Bioorganic & Medicinal Chemistry, vol. 9, 2001, 337-345.*
Katritzky et al. QSAR modeling of anti-invasive activity of organic compounds using structural descriptors. Biorganic & Medicinal Chemistry, vol. 14, 2006, 6933-6939.*
International Search Report and Written Opinion of PCT/IB2014/060496 of Jul. 1, 2014.
Parmar, et al., "Anti-invasive Activity of Alkaloids and Polyphenolics in Vitro", Biiorganic & Medicinal Chemistry, vol. 5, No. 8 pp. 1609-1619, 1997.

* cited by examiner

*Primary Examiner* — Sikarl Witherspoon
(74) *Attorney, Agent, or Firm* — Silvia Salvadori, P.C.; Silvia Salvadori

(57) ABSTRACT

The present invention relates to novel synthetic analogs of xanthohumol and the use thereof.

13 Claims, 9 Drawing Sheets

Tables summarising MTT assays; values standardised on control

| | IC50 24h | IC50 96h |
|---|---|---|
| XN | 47 μM | 20 μM |
| LR6 | 39 μM | 17 μM |
| LR7 | 59 μM | 26 μM |
| LR10 | 36 μM | 24 μM |
| LR14 | 25 μM | 24 μM |
| LR15 | 110 μM | 134 μM |
| LR16 | 23 μM | 26 μM |
| LR17 | 30 μM | 22 μM |
| LR18 | 527 μM | 126 μM |
| LR18 B | 37 μM | 52 μM |
| LR19 | 24 μM | 17 μM | compound with the highest % of inhibition

| | 24 | 48 | 72 | 96 |
|---|---|---|---|---|
| 1 nM | LR6 2,7 | LR14 4 | LR19 1,6 | LR15 10,2 |
| 10 nM | LR7 4,7 | LR18B 3,9 | LR16 2,5 | LR16 14,8 |
| 100 nM | LR18B 1,9 | LR18B 4,2 | XN 4 | LR15 13 |
| 1 μM | LR18B 1,4 | LR18B 5,3 | LR16 4,6 | LR16 11,4 |
| 10 μM | LR16 30,6 | LR16 36,9 | LR16 40,7 | LR16 36,1 |
| 20 μM | LR19 51,4 | LR19 62,5 | LR19 74,4 | XN 65 |

Figure 8

Reduction of NO release (a) and NF-kB action (b) by XN

SYNTHETIC ANALOGUES OF XANTHOHUMOL

This application is a U.S. national stage of PCT/IB2014/060496 filed on 7 Apr. 2014, which claims priority to and the benefit of Italian Application No. MI2013A000536 filed on 8 Apr. 2013, the contents of which are incorporated herein by reference in their entireties.

TECHNICAL FIELD OF INVENTION

The present invention relates to novel synthetic analogues of xanthohumol (XN), a prenylated chalcone of natural origin present in hops (*Humulus lupulus*).

STATE OF THE ART

Natural compounds extracted from plants, such as flavonoids, exhibit chemopreventive or therapeutic properties in various disorders.

The flavonoids contained in many foods and drinks commonly used for human consumption include compounds belonging to various structural classes, such as flavones, flavonols (quercetin), catechins, flavonones (naringenin), isoflavones and chalcones (xanthohumol). Xanthohumol (XN) is the main chalcone contained in the female inflorescence of the hop plant (*Humulus lupulus* L.—Cannabaceae), and is extensively used in beer manufacturing processes for adding flavour and aroma and stabilising the froth. Beer, wherein XN is present in concentrations of about 0.96 mg/l (1.95 μM), can represent one of the major sources of flavones in the diet.

Although polyphenol compounds are poorly absorbed at intestinal level, XN is extensively metabolised in the stomach to isoxanthohumol (IXN) which, in turn, is converted to 8-prenylnaringenin (8SE) by the intestinal flora and hepatic microsomal enzymes (Scheme 1).

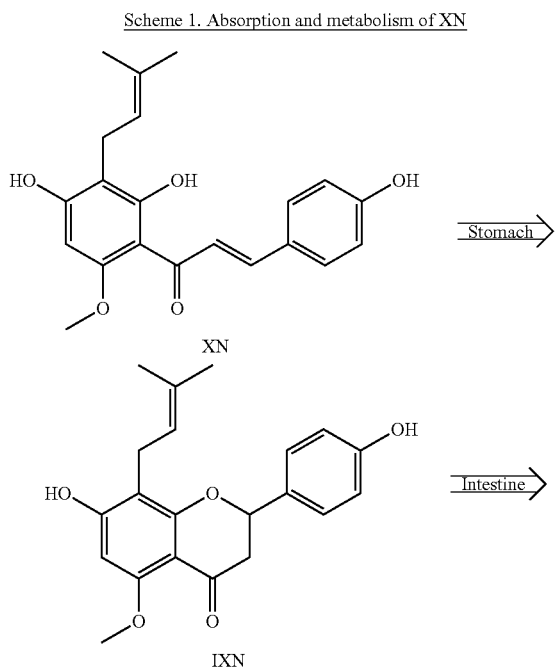

Scheme 1. Absorption and metabolism of XN

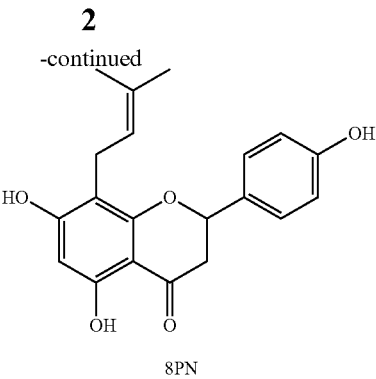

8PN

XN, a prenylated chalcone which has the structure of flavonoids with an open carbon ring, accounts for 82-89% of the prenylated chalcones known among the European hop varieties.

The biological effects of some chalcones are closely correlated with their chemical structure; substitutions induce significant changes in the pharmacological effects of these compounds [Nikolic D, Li Y, Chadwick L. R; "Metabolism of xanthohumol and isoxanthohumol, prenylated flavonoids from hops, by human lever microsomes"; Journal Mass Spectrom: 40, 289-299, (2005)].

XN possesses anti-invasive, anti-proliferative, anti-angiogenic, pro-apoptotic, anti-infective and inhibiting activities on the enzymes of cytochrome P450 involved in the metabolic activation of carcinogenesis. The properties of XN also include anti-inflammatory activity, exercised by reducing the production of nitric oxide (NO), a free radical involved in carcinogenesis and angiogenic processes [Zhao F, Nozawa H, Daikonnya A, Kondo K, Kitanaka S. Inhibitors of nitric oxide production from hops (*Humulus lupulus* L.). Biol Pharm Bull. 2003 January; 26(1):61-5]. XN has an inductive effect on quinone reductase, which modulates the hepatic expression of the genes involved in the distribution, in the metabolism of thyroid hormones, and the metabolism of glucose and lipids, and an immunomodulating affect against skin aging [Dietz B M, Kang Y H, Liu G, Eggler A L, Yao P, Chadwick L R, Pauli G F, Farnsworth N R, Mesecar A D, van Breemen R B, Bolton J L. Xanthohumol isolated from *Humulus lupulus* Inhibits menadione-induced DNA damage through induction of quinine reductase. Chem Res Toxicol. 2005 August; 18(8):1296-305].

Recent studies conducted on breast cancer cell lines have demonstrated the anti-invasive and anti-proliferative activity of XN. XN has proved able to restore the function of the E-cadherin-catenin complex, thus stimulating cell aggregation [Barbara Vanhoecke, Lara Derycke, Veerle Van Marck; "Antiinvasive effect of xanthohumol, a prenylated chalcone present in hops (*Humulus lupulus* L.) and beer"; Int. J. Cancer: 117, 889-895 (2005)]. To evaluate the anti-proliferative potential of XN on breast cancer cells, its influence on DNA synthesis in MDA-MB435 cells was studied in an in vitro system, and it was found that said compound inhibits the activity of the human DNA polymerase-α enzyme. It has also been demonstrated that treatment with XN induces cell accumulation in the S phase of the cell cycle and a terminal differentiation in HL-60 myelocytic leukaemia cells [Harikumar K B, Kunnumakkara A B, Ahn K S, Anand P, Krishnan S, Guha S, Aggarwal B B. Modification of the cysteine residues in IkappaBalpha kinase and NF-kappaB (p65) by xanthohumol leads to suppression of NF-kappaB-regulated gene products and potentiation of apoptosis in leukaemia cells. Blood. 2009 Feb. 26; 113(9):2003-13].

XN induces apoptosis in breast cancer cells by inducing cleavage of the PARP (Poly-ADP-Ribose-Polymerase) protein, the nuclear substrate of caspase [Barbara Vanhoecke, Lara Derycke, Veerle Van Marck; "Antiinvasive effect of xanthohumol, a prenylated chalcone present in hops (*Humulus lupulus* L.) and beer"; Int. J. Cancer: 117, 889-895 (2005)].

Its anti-proliferative activity has also been investigated on hepatocarcinoma cell lines, wherein XN, administered at the concentration of 25 µM, induces apoptosis [Ho Y C, Liu C H, Chen C N, Duan K J, Lin M T. Inhibitory effects of xanthohumol from hops (*Humulus lupulus* L.) on human hepatocellular carcinoma cell lines. Phytother Res. 2008 November; 22(11):1465-8]. At low concentrations, it represses the proliferation and migration and the pro-inflammatory activity of NF-kB and the expression of Interleukin-8 [Christoph Dorn, Thomas S. Weiss, Jorg Heilmann; "Xanthohumol, a prenylated chalcone derived from hops, inhibits proliferation, migration and interleukin-8 expression of hepatocellular carcinoma cells"; International Journal of Oncology: 36, 435-441 (2010)]. High concentrations of XN (exceeding 100 µM) have no effect on the viability of the hepatocytes, which indicates the low toxicity and safety of the natural product [Christoph Dorn, Thomas S. Weiss, Jorg Heilmann; "Xanthohumol, a prenylated chalcone derived from hops, inhibits proliferation, migration and interleukin-8 expression of hepatocellular carcinoma cells"; International Journal of Oncology: 36, 435-441 (2010)]. Jung A. et al. compared the anti-invasive effects of XN and its synthetic derivatives O-methylxanthohumol ether SEM (XN-SEM), xanthohumol C (XNC) and xanthohumol C ether MOM (XNC-MOM) (Scheme 2) with the expression of extracellular matrix metalloproteases (MMPs) in fibrosarcoma cells.

Scheme 2. Structures of XN, XN-SEM, XNC and XNC-MOM

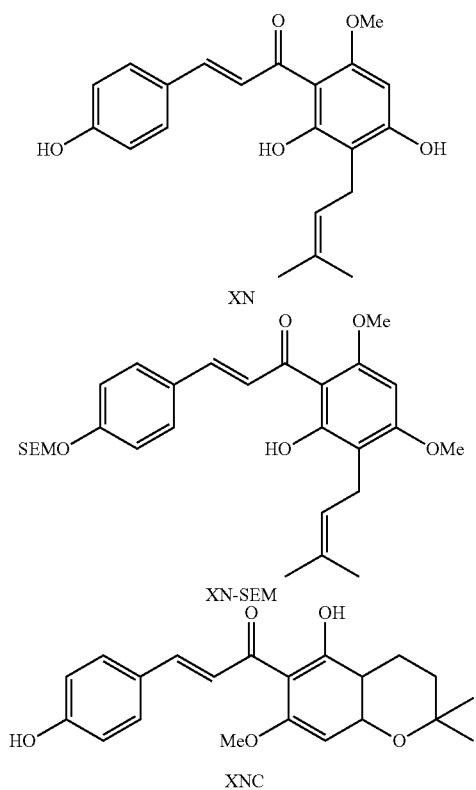

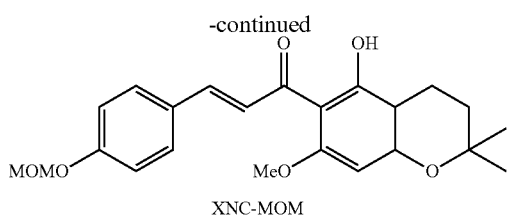

XNC-MOM

Of the various MMPs, those most often expressed in malignant tumours and vascular disease are gelatinase A (MMP-2) and B (MMP-9). XN inhibits invasion by fibrosarcoma cells and the activity of MMP-9 at the concentration of 10 µM; it inhibits the expression of TIMP-1, an MMP tissue inhibitor which forms a complex with pro-MMP9, preventing its activation. The activity of MMP-2 is also strongly inhibited by XN (10 µM) [Philips N, Samuel M, Arena R, Chen Y J, Conte J, Natarajan P, Haas G, Gonzalez S. Direct inhibition of elastase and matrixmetalloproteinases and stimulation of biosynthesis of fibrillar collagens, elastin, and fibrillins by xanthohumol. J Cosmet Sci. 2010 March-April; 61(2):125-32. Erratum in: J Cosmet Sci. 2010 November-December; 61(6):485. Natrajan, Prashanti [corrected to Natarajan, Prashanthi]. XN has therefore exhibited excellent anti-invasive properties on breast cancer and fibrosarcoma cell lines [Goto K, Asai T, Hara S, Namatame I, Tomoda H, Ikemoto M, Oku N. Enhanced antitumor activity of xanthohumol, a diacylglycerol acyltransferase inhibitor under hypoxia. Cancer Lett. 2005 Mar. 10; 219(2):215-22]. XNC, also known as dehydroxanthohumol, is a pyranochalcone whose principal activities are antifungal, anti-proliferative, anti-mutagenic and antioxidant. This compound, unlike XN, has a pyranose ring instead of the prenyl group on C-3', which involves loss of cytotoxic activity. Moreover, although XN-SEM presents the prenyl group as XN, it has no cytotoxic effect on fibrosarcoma cells.

XN also exhibits anti-angiogenic activity. Vascularisation of the tumour is necessary for its growth and metastatic spread. Inhibiting and delaying angiogenesis are therefore possible strategies for the treatment and prevention of cancer. Studies have been conducted on the changes induced by XN in the various cell populations most involved in tumour angiogenesis, namely endothelial cells. XN, at µM concentrations, reduces in vitro the proliferation, invasive activity and ability of the endothelial cells to form a tubular network in extracellular matrix. At molecular level, XN inhibits activation of NF-kB and phosphorylation of IkBα, preventing the translocation of NF-kB to the nucleus and the expression of pro-inflammatory genes [Monteiro R, Calhau C, Silva A O, Pinheiro-Silva S, Guerreiro S, Gartner F, Azevedo I, Soares R. Xanthohumol inhibits inflammatory factor production and angiogenesis in breast cancer xenografts. J Cell Biochem. 2008 Aug. 1; 104(5):1699-707]. XN also prevents angiogenesis and reduces tumour growth in assays conducted in vivo [Adriana Albini, Raffaella Dell'Eva, Nicoletta Ferrari; "Mechanisms of the antiangiogenic activity by the hop flavonoid xanthohumol: NF-kB and Akt as targets"; The FASEB Journal: 10.1096/fj.05-5128fje, 30 Dec. 2005]. In endothelial cells, XN inhibits the phosphorylation of AKT, a serine/threonine kinase which is important in regulating cell migration and survival signals [Adriana Albini, Raffaella Dell'Eva, Nicoletta Ferrari; "Mechanisms of the antiangiogenic activity by the hop flavonoid xanthohumol: NF-kB and Akt as targets"; The FASEB Journal: 10.1096/fj.05-5128fje, 30 Dec. 2005]. Endothelial cells activated by an angiogenic stimulus enter a proliferative state. XN performs a potent cytotoxic activity against these cells at the dose of 10 μM, whereas at lower concentrations it does not exhibit any significant effect, even after long exposure times. Cell death is only observed at concentrations exceeding 25 μM. XN inhibits chemotaxis of the endothelial cells and invasion in vitro at low concentrations (5 μM), with complete inhibition at 10 μM [Adriana Albini, Raffaella Dell'Eva, Nicoletta Ferrari; "Mechanisms of the antiangiogenic activity by the hop flavonoid xanthohumol: NF-kB and Akt as targets"; The FASEB Journal: 10.1096/fj.05-5128fje, 30 Dec. 2005]. The doses of XN which are effective on migration have not, however, led to the activation of apoptotic mechanisms, suggesting that migration and growth are the main targets for the reduction of angiogenesis and tumour growth observed in vivo. In vitro assays have demonstrated that XN also interferes to a dose-dependent extent with the morphogenesis of the endothelial cells in the matrix, in the presence of which they spontaneously form structures resembling a network of capillaries [Adriana Albini, Raffaella Dell'Eva, Nicoletta Ferrari; "Mechanisms of the antiangiogenic activity by the hop flavonoid xanthohumol: NF-kB and Akt as targets"; The FASEB Journal: 10.1096/fj.05-5128fje, 30 Dec. 2005]. The effects are evident in a concentration interval of 5-10 μM, and no toxicity was observed, even at 200 μM. Other studies, conducted in vivo on tumour angiogenesis, demonstrate that XN, when administered orally, inhibits vascularisation in xenograft models [Adriana Albini, Raffaella Dell'Eva, Nicoletta Ferrari; "Mechanisms of the antiangiogenic activity by the hop flavonoid xanthohumol: NF-kB and Akt as targets"; The FASEB Journal: 10.1096/fj.05-5128fje, 30 Dec. 2005].

Kuzlil et al. have demonstrated that XN induces apoptosis, boosting the tumour necrosis factor in myeloma and leukaemia cells [Kuzlil B. Harikumar, Ajaikumar B. Kunnumakkara, Kwang S. Ahn; "Modification of the cysteine residues in IkBα kinase and NF-kB (p65) by xanthohumol leads to suppression of NF-kB-regulated gene products and potentiation of apoptosis in leukaemia cells"; Blood: 113(9), 2003-2013 (2009)]. These researchers observed that XN, containing a Michael acceptor and an electrophilic carbonyl group, determines down-regulation of constitutive, inducible NF-kB activation, interacting with subunit p65 via cysteine residue 38 [Kuzlil B. Harikumar, Ajaikumar B. Kunnumakkara, Kwang S. Ahn; "Modification of the cysteine residues in IkBα kinase and NF-kB (p65) by xanthohumol leads to suppression of NF-kB-regulated gene products and potentiation of apoptosis in leukaemia cells"; Blood: 113(9), 2003-2013 (2009)]. XN also acts directly on the activation of the NF-kB dependent kinase IkBα (IKK), interacting with the sulphydryl group of cysteine 179 of IKK. Through interaction with these cysteine groups, XN boosts its apoptotic action and suppresses the production of antiapoptotic genes [Kuzlil B. Harikumar, Ajaikumar B. Kunnumakkara, Kwang S. Ahn; "Modification of the cysteine residues in IkBα kinase and NF-kB (p65) by xanthohumol leads to suppression of NF-kB-regulated gene products and potentiation of apoptosis in leukaemia cells"; Blood: 113(9), 2003-2013 (2009)].

Prostate cancer is the most common form of cancer diagnosed in men. Deeb et al. have studied the effects of XN on hormone-sensitive and hormone-refractory prostate cancer. The results demonstrate the inhibitory effect of XN on the growth of prostate cancer cell lines (40 μM) and the induction of apoptosis via the intrinsic pathway, which involves activation of pro-caspases-3, -8 and -9, mitochondrial depolarisation and the release of cytochrome C from the mitochondrion [Deeb D, Gao X, Jiang H, Arbab A S, Dulchaysky S A, Gautam S C. Growth inhibitory and apoptosis-inducing effects of xanthohumol, a prenylated chalcone present in hops, in human prostate cancer cells. Anticancer Res. 2010 September; 30(9):3333-9]. XN also inhibits antiapoptotic proteins Akt, mTOR and NF-kB, suggesting that their inactivation is necessary for the induction of apoptosis [D. Deeb, X. Gao, H. Jiang; "Growth inhibitory and apoptosis-inducing effects of xanthohumol, a prenylated chalcone present in hops, in human prostate cancer cells"; Internation Journal of Cancer Research and Treatment: 30 (9), 3333-3339 (2010)].

XN possesses other biopharmacological activities, such as antibacterial activity [Clarissa Gerhauser; "Broad spectrum antiinfective potential of xanthohumol from hop (*Humulus lupulus* L.) in comparison with activities of other hop constituents and xanthohumol metabolites"; Mol. Nutr. Food Res: 49, 827-831 (2005); Teuber M., Schmalreck A. F., "Membrane leakage in *Bacillus subtilis* 168 induced by the hop constituents lupulone, humulone, isohumulone and humulinic acid"; Arch. Mikrobiol: 94, 159-171 (1973; Mizobuchi S., Sato Y; "A new Flavone with antifungal activity isolated from hops"; Agricultural and Biological Chemistry: 48, 2771-2775 (1984); Bhattacharya S., Virani S. Zavro M., Haas G. J.; "Inhibition of *streptococcus mutans* and other oral streptococci by hop (*Humulus Lupulus* L.) constituents"; Economic Botany: 57, 118-125 (2003)].

XN inhibits the cytopathic effects induced by the HIV-1 virus, the production of viral antigen P24, and reverse transcriptase activity [Buckwold V. E., Wilson R. J., Nalca A., Beer B. B. et Al.; "Antiviral activity of hop constituents against a series of DNA and RNA viruses"; Antiviral Research: 61, 57-62 (2004)]. In a study by Buckwold et al., XN and other constituents of hops exhibited inhibitory activity in vitro against a series of RNA and DNA viruses. XN inhibits the growth of the RNA virus BVDV (bovine diarrhoea virus, an analogue of the hepatitis C virus, HCV) and of the DNA viruses CMV (cytomegalovirus), HSV-1 (Herpes simplex type 1) and HSV-2 (Herpes simplex type 2), but has no effect on the RNA virus HRV (human rhinovirus). However, IXN is active at higher concentrations on all the species cited [Buckwold V. E., Wilson R. J., Nalca A., Beer B. B. et Al.; "Antiviral activity of hop constituents against a series of DNA and RNA viruses"; Antiviral Research: 61, 57-62 (2004)]. The BVDV and HCV viruses belong to the Flaviviridae family, and share homologous protein regions, such as virion structure, genome organisation and replication strategy [Buckwold V. E., Wilson R. J., Nalca A., Beer B. B. et Al.; "Antiviral activity of hop constituents against a series of DNA and RNA viruses"; Antiviral Research: 61, 57-62 (2004)]. BVDV is often used as a surrogate model to evaluate potential compounds with antiviral activity on HCV. In view of these factors, XN can be used as a base for the development of novel anti-HCV compounds. For this purpose, studies have been conducted on the effect of XN in combination with interferon-α (IFN-α), using the expression of viral protein E2 as the evaluation parameter. The results demonstrate that the inhibitory activity of XN combined with IFN-α is greater than that of IFN-α used alone, thus emphasising the synergic effect of the two compounds on BVDV replication [Zhang N, Liu Z, Han Q, Chen J, Lv Y. Xanthohumol enhances antiviral effect of interferon alpha-2b against bovine viral diarrhea virus, a surrogate of hepatitis C virus. Phytomedicine. 2010 April; 17(5):310-6]. The combination of the two may therefore offer substantial benefits to individuals who are particularly sensitive to high doses of interferon [Ni Zhang, Zhengwen Liu, Qunying Han; "Xanthohumol enhances antiviral effect of interferon α-2b against bovine viral diarrhea virus, a surrogate of hepatitis C virus"; Phytomedicine: 17, 310-316 (2010)].

The constituents of hops have also been analysed for their antifungal activity. XN and some correlated compounds, such as naringenin, 6-prenylnaringenin, 8-prenylnaringenin and IXN (Scheme 3), have been tested against fungi pathogenic for humans [Frölich S, Schubert C, Bienzle U, Jenett-Siems K. In vitro antiplasmodial activity of prenylated chalcone derivatives of hops (*Humulus lupulus*) and their interaction with haemin. J Antimicrob Chemother. 2005 June; 55(6):883-7]. XN and 6-prenylnaringenin proved to be the most potent antifungal agents, inhibiting the growth of the dermatophytes *T. mentagrophytes, T. rubrum* and *M. rouxianus* more efficiently than griseofulvin, used as reference. However, IXN is inactive. *C. albicans* does not respond to XN or naringenin [Frölich S, Schubert C, Bienzle U, Jenett-Siems K. In vitro antiplasmodial activity of prenylated chalcone derivatives of hops (*Humulus lupulus*) and their interaction with haemin. J Antimicrob Chemother. 2005 June; 55(6):883-7].

Scheme 3. Molecular structure of naringenin (a), 6-prenylnaringenin (b) and 8-prenylaringenin (c)

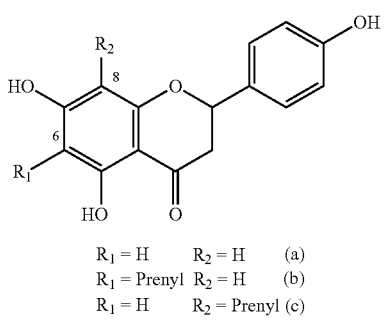

$R_1 = H$   $R_2 = H$   (a)
$R_1 = Prenyl$   $R_2 = H$   (b)
$R_1 = H$   $R_2 = Prenyl$   (c)

XN also exhibits antiprotozoal activities by acting on cell strains of chloroquine-sensitive and chloroquine-resistant plasmodia, by means of an mechanism action which is not yet clear [Frölich S., Schubert C., Bienzle U.; "In vitro antiplasmodial activity of prenylated chalcone derivates of hops (*Humulus lupulus*) and their interaction with haemin"; Journal of Antimicrobial Chemotherapy: 55, 883-887 (2005)].

Another pharmacological activity of XN is its anti-inflammatory activity. Chronic neuroinflammation is a characteristic of neurodegenerative disorders, such as Parkinson's disease (PD), involving activation of the microglial cells in the substantia nigra, increased levels of pro-inflammatory cytokines in the striata and the substantia nigra, and activation of the pro-inflammatory NE-kB signalling pathway, [Lee I S, Lim J, Gal J, Kang J C, Kim H J, Kang B Y, Choi H J. Anti-inflammatory activity of xanthohumol involves heme oxygenase-1 induction via NRF2-ARE signaling in microglial BV2 cells. Neurochem Int. 2011 February; 58(2):153-60]. Some studies demonstrate that XN significantly inhibits excessive production of inflammation mediators (NO, IL-1β, TNF-α) and activation of transcription factor NF-kB in the glial cells (FIG. 9) [Lee I S, Lim J, Gal J, Kang J C, Kim H J, Kang B Y, Choi H J. Anti-inflammatory activity of xanthohumol involves heme oxygenase-1 induction via NRF2-ARE signaling in microglial BV2 cells. Neurochem Int. 2011 February; 58(2):153-60].

XN also increases the levels of NRF2 (Nuclear Factor-like 2), promoting the activation of specific regions of the promoter (Antioxidant Responsive Element, ARE) and consequently giving rise to overexpression of transcription of the target genes, such as quinone oxidoreductase-1 (NQO1) and haem-oxgenase-1 (HO-1) [Ik-Soo Lee, Juhee Lim, Jiyeong Gal; "Anti-inflammatory activity of xanthohumol involves heme oxygenase-1 induction via NRF2-ARE signaling in microglial BV2 cells"; Neurochemistry International: 58, 153-160 (2011)]. Studies conducted in vitro demonstrate that flavonoids can alter the thyroid functions [Radović B, Hussong R, Gerhauser C, Meinl W, Frank N, Becker H, Kohrle J. Xanthohumol, a prenylated chalcone from hops, modulates hepatic expression of genes involved in thyroid hormone distribution and metabolism. Mol Nutr Food Res. 2010 July; 54 Suppl 2:S225-35].

XN modulates the expression of hepatic enzymes and the proteins essential for maintaining the homeostasis of the thyroid hormone (TH). XN acts on the TH levels and the hepatic enzymes which are important for its breakdown and elimination [Branislav Radovic, Ragna Hussong, Clarissa Gerhauser; "Xanthohumol, a prenylated chalcone from hops, modulates hepatic expression of genes involved in thyroid hormone distribution and metabolism"; Mol. Nutr. Food Res: 54, S225-S235 (2010)].

XN also reduces the genotoxicity caused by reactive oxygen species and by various groups of carcinogenic mutagens ingested with food [Franziska Felk, Wolfgang W. Huber, Metka Filipic; "Xanthohumol, a prenylated flavonoid contained in beer, prevents the induction of preneoplastic lesions and DNA damage in liver and colon induced by the heterocyclic aromatic amine amino-3-methyl-imidazo[4,5-f]quinoline (IQ)"; Mutation Research: 691, 17-22 (2010)].

Nuclear hormone receptors are part of a very large group of transcription factors, and are efficient targets for a therapeutic strategy designed to control the metabolism of glucose, lipids, lipoproteins, bile acids, etc., whose alterations are correlated with the onset of metabolic syndrome. FXR (Farnesoid X Receptor) is a member of the superfamily of nuclear hormone receptors. It regulates the synthesis of bile acids by means of a negative feedback mechanism. FXR therefore plays an important role in the metabolism of cholesterol, lipids, lipoproteins and carbohydrates. Natural ligands which act on this receptor can regulate metabolic syndrome, reducing cardiovascular risks. In vitro, XN can activate FXR and modulate the genes involved in the metabolism of lipids and glucose [Hajime Nozawa; "Xanthohumol, the chalcone from beer hops (*Humulus lupulus* L.), is the ligand for farnesoid X receptor and ameliorates lipid and glucose metabolism in KK-Ay mice"; Biochemical and Biophysical Research Communications: 336, 754-761 (2005)].

XN also has an immunosuppressant effect on the proliferation of T cells, the development of killer cells activated by IL-2 (LAK), cytotoxic T lymphocytes (CTL) and the production of cytokines released by the Th1 helper cells (IL-2, IFN-γ and TNF-α) [Gao X, Deeb D, Liu Y, Gautam S, Dulchaysky S A, Gautam S C. Immunomodulatory activity of xanthohumol: inhibition of T cell proliferation, cell-mediated cytotoxicity and Th1 cytokine production through suppression of NF-kappaB. Immunopharmacol Immunotoxicol. 2009; 31(3):477-84]. The suppression of the cell-mediated immune response by XN is associated with inhibition of NF-kB transcription [Xiaohua Gao, Dorrah Deeb, Yongbo Liu; "Immunomodulatory activity of xanthohumol: inhibition of T cell proliferation, cell-mediated cytotoxicity and Th1 cytokine production through suppression of NF-kB"; Immunopharmacol Immunotoxicol: 31, 477-484 (2009)].

The use of XN can also have important implications for the cosmetic industry. Skin aging, the most common clinical symptoms of which are wrinkles, loss of elasticity and sagging, is the result of deterioration of extracellular matrix (ECM), formed by collagen and elastin. Type I, III and V collagen fibres form the structural component of the skin, and are broken down by collagenases (MMP-1), whereas elastin, a substrate of gelatinase (MMP-2 and MMP-9), forms elastic fibres with fibrillin, providing stability and elasticity. Atrophy of the elastin and collagen fibres in elderly skin is due to reduced synthesis of its constituents and increased expression of degradation enzymes, such as collagenase (MMP-1), gelatinase 2 and 9 (MMP-2, MMP-9), and elastase. The great attention paid nowadays to maintaining physical fitness and beauty has led the cosmetic industry to seek new molecules of natural origin which inhibit MMPs and elastase, and at the same time stimulate the formation of collagen and elastin. Topical administration of XN is an effective aid against the signs of aging. XN exhibits a dual activity: at low concentrations it inhibits the activity of MMP-9 and elastase, and at slightly higher concentrations that of MMP-1 and MMP-2; at the same time, it stimulates the expression of type I, III and V collagen, elastin and fibrillin 1 and 2 in the fibroblasts of the dermis [M. Samuel, R. Arena, J. Conte; "Direct inhibition of elastase and matrixmetalloproteinases and stimulation of biosynthesis of fibrillar collagens, elastin, and fibrillins by Xanthohumol"; International Journal of Cosmetic Science: 61, 125-132 (2010)].

Natural XN can be obtained by extraction from the female inflorescence of the hop plant, or synthesised. XN, some of its natural metabolites and a few synthetic analogues have so far been little studied for their biopharmacological properties [Vogel S, Heilmann J; "Synthesis, Cytotoxicity, and Antioxidative Activity of Minor Prenylated Chalcones from *Humulus Lupulus*"; Journal Nat. Prod: 71, 1237-41 (2008); Emily Ho, Frederik Stevens, Cristobal L. Miranda, et Al; "Prostate cancer and benign prostatic hyperplasia treatments" US 2008/0233221; R. S. Khupse, P. W. Erhardt; "Total Synthesis of Xanthohumol"; J. Nat. Prod: 70, 1507-1509 (2007)].

Trimethoxychalcone derivatives which inhibit the growth of *Leishmania braziliensis* are described by Bello M L et al., Biorg. & Med. Chem. Lett., 19(16), 5046-5052, 2011.

CN 101906029 discloses flavonoid derivatives with a chalcone structure and their cyclised derivatives with a 2-arylidenebenzofuranone structure as tyrosine kinase inhibitors.

Chalcone derivatives which inhibit the tyrosine phosphatase A of *Mycobacterium tuberculosis* are described by Chiaradia L D et al, Biorg. & Med. Chem. Lett., 18(23), 6227-6230, 2008.

Chalcone derivatives obtained from 2,4,6-trimethoxyacetophenone, which inhibit the release of NO in murine macrophages in vitro, are described by Chiaradia L D et al. in Biorg. & Med. Chem., 16(2), 658-667, 2008.

CN 101041646 discloses 4',6'-disubstituted 2'-hydroxyl-3'-alkylaminopropyl chalcone derivatives which are useful as antitumoral agents.

C-prenyl and O-allyl chalcones able to inhibit the invasion of human breast cancer cells MCF7/6 in vitro are described by Mukherjee S et al., Biorg. & Med. Chem., 9(2), 337-345, 2001.

Parmar V S et al., Indian Journal of Chemistry, Section B, 37B(7), 628-643, 1998 describes chalcones bearing various substituents such as prenyl, methoxy and benzhydryl, able to inhibit in vitro the invasion of human breast cancer cells MCF7/6. Some of these compounds also exhibit herbicidal activity.

In view of the low potency and selective action of XN and its synthetic analogues known to date, there is still a need to identify new molecules which are more effective in degenerative processes characterised by cell hyperproliferation, angiogenesis and tissue destruction caused by uncontrolled hyperproteolysis, and which possess better properties in terms of bioavailability, efficacy and reduced toxicity than those currently known.

SUMMARY OF THE INVENTION

The present invention relates to compounds of general formula:

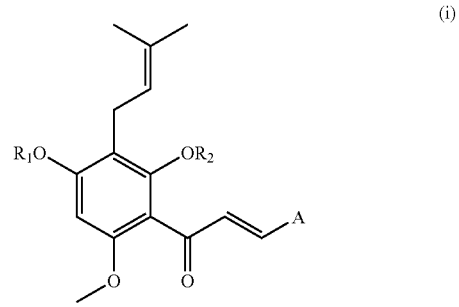

(i)

wherein the substituents can have the meanings described below.

The invention also relates to the use of said compounds as medicaments, and to compositions containing them.

LIST OF FIGURES

FIG. 8 contains tables summarising the results of the MTT assays.

Figure 9:
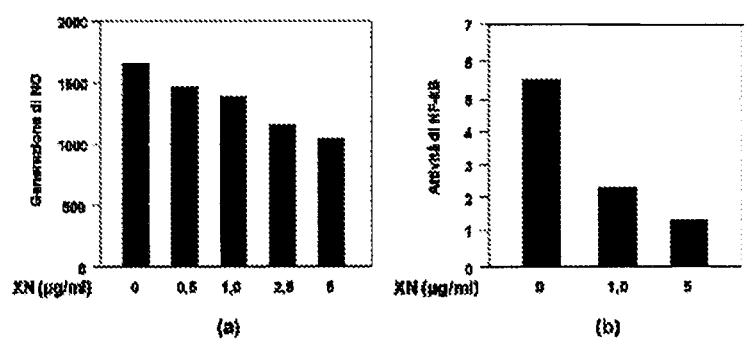

FIG. 9 shows reduction of NO release (a) and NF-kB action (b) by XN.

DETAILED DESCRIPTION OF THE INVENTION

The present invention relates to a compound of general formula (i):

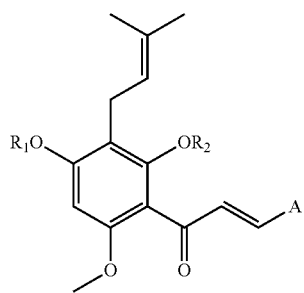

(i)

wherein:

$R_1$ and $R_2$ can be, independently of one another, selected from the group comprising H; methyl; straight or branched alkyl with 2 to 10 carbon atoms; straight or branched alkyl with 2 to 10 carbon atoms containing 1 or 2 unsaturations; cycloalkyl with 4 to 6 carbon atoms; cycloalkyl with 4 to 6 carbon atoms containing 1 or 2 unsaturations; alkoxyalkyl, which can be selected from the group comprising $CH_3OCH_2—$, $CH_3OCH_2CH_2—$ or $CH_3(OCH_2CH_2)_n—$, $CH_3(NHCH_2CH_2)_n—$, $CH_3(CH_2)_nCO(NHCH_2CH_2)_n—$, $CH_3(CH_2)_nSO_2(NHCH_2CH_2)_n—$, $HN(CH_2CH_2)_2N—(CH_2CH_2)_n—$, $CH_3N(CH_2CH_2)_2N—(CH_2CH_2)_n—$, $CH_3(CH_2)_nCO—N(CH_2CH_2)_2N—(CH_2CH_2)_n—$, $CH_3(CH_2)_nSO_2—N(CH_2CH_2)_2N—(CH_2CH_2)_n—$, $O(CH_2CH_2)_2N—(CH_2CH_2)_n—$; benzyl; benzyl optionally substituted in any of the substitutable positions by 1 to 5 halogen atoms independently selected from the group comprising F, Cl, Br and I; benzyl substituted by —$NH_2$, —$NHCH_3$, —$NHCOCH_3$, —NHCO— alkyl, —$NHSO_2CH_3$, —$NHSO_2$-alkyl, —$SO_2CH_3$, —$SO_2$-alkyl, —$SO_2NHCH_3$, —$SO_2NHCO$-alkyl, —$NO_2$, —$OCH_3$, —$CO_2H$, —$CONHCH_3$, —CONH-alkyl, —$CO_2CH_3$, —$CO_2$-alkyl, —$CONHSO_2CH_3$, —$CONHSO_2$-alkyl, alkyl being as defined above;

n is an integer between 1 and 5;

A can be a monocyclic or bicyclic aryl or a heterocyclic, aromatic or non-aromatic, monocyclic or bicyclic ring, selected from the group comprising pyrrole, pyrrolidine, 3-pyrroline, 2H-pyrrole, 2-pyrroline, indole, isoindole, 3H-indole, indolizine, indoline, carbazole, furan, benzofuran, isobenzofuran, 2H-pyran, 4H-pyran, benzo[b]thiophene, thiophene, pyridine, piperidine, 4H-quinolizine, isoquinoline, quinoline, tetrahydroquinoline, 1,8-naphthyridine, acridine, oxazole, isoxazole, benzoxazole, benzothiazole, isothiazole, thiazole, imidazole, 2-imidazole, imidazolidine, tetrazole, 1,2,3-triazole, 1,2,4-triazole, 1,2,3-oxadiazole, benzoimidazole, purine, 1,4-dioxane, 1,3-dioxolane, 1,3-dithiane, 1,4-dithiane, 1,3,5-trithiane, morpholine, thiomorpholine, phenothiazine, pyrazole, 2-pyrazoline, pyrazolidine, quinazoline, cinnoline, pyrimidine, pyrazine, pteridine, phthalazine, 1,2,4-triazine, 1,3,5-triazine, pyridazine, piperazine, quinoxaline, phenazine and 1H-indazole, wherein said aromatic or non-aromatic heterocyclic ring can be benzocondensed and/or further substituted with halogen, alkyl, alkenyl, alkinyl, alkoxy, amino, amido, acylamido, sulphonamido, acyl, sulphonyl, aryl or heteroaryl;

wherein the substituents on the A ring are independently selected from the group comprising H, —O-alkyl, —$OCH_3$, Cl, F, Br, I, —$NO_2$, —$NH_2$, —$NHCH_3$, —NH-alkyl, —$NHCOCH_3$, —NHCO-alkyl, —$NHSO_2CH_3$, —$NHSO_2$-alkyl, —$SO_2CH_3$, —$SO_2$-alkyl, —$SO_2NH_2$, —$SO_2NHCH_3$, —$SO_2NH$-alkyl, —$SO_2NHCOCH_3$, —$SO_2NHCO$-alkyl, —$CO_2H$, —$CONHCH_3$, —CONH-alkyl, —$CO_2CH_3$, —$CO_2$-alkyl, —$CONHSO_2CH_3$ and —$CONHSO_2$-alkyl, alkyl being as defined above for $R_1$, $R_2$, wherein at least one of the substituents on the A ring is H;

provided that the compound of general formula (i) is not:
(E)-3-phenyl-1-(2,4,6-trimethoxy-3-(3-methylbut-2-enyl)phenyl)prop-2-en-1-one; or
(E)-3-phenyl-1-(2-hydroxy-4,6-dimethoxy-3-(3-methylbut-2-enyl)phenyl)prop-2-en-1-one.

When $R_1$ is H or $R_2$ is H, the isoprenyl group of general formula (i) can optionally cyclise to form a benzocondensed system of 2,2-dimethylchroman, giving a compound of general formula (ii) or (iii):

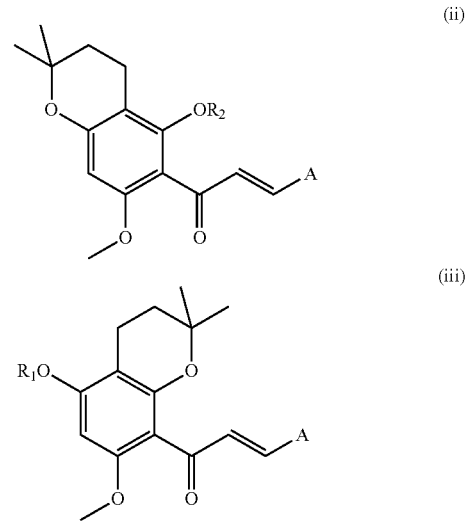

wherein $R_1$, $R_2$ and A are as defined above for formula (i).

In a preferred embodiment, the invention relates to compounds of general formula (iv):

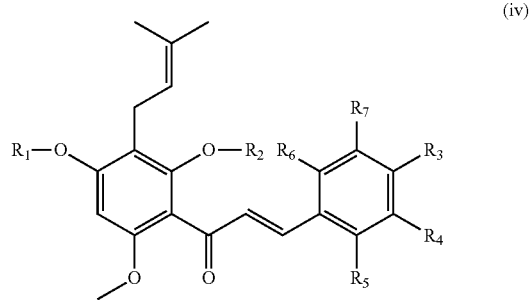

wherein $R_1$, $R_2$ are as defined above for formula (i) and $R_3$, $R_4$, $R_5$, $R_6$ and $R_7$ are selected independently from the group comprising H, —O-alkyl, —$OCH_3$, Cl, F, Br, I, —$NO_2$, —$NH_2$, —$NHCH_3$, —NH-alkyl, —$NHCOCH_3$, —NHCO-alkyl, —$NHSO_2CH_3$, —$NHSO_2$-alkyl, —$SO_2CH_3$, —$SO_2$-alkyl, —$SO_2NH_2$, —$SO_2NHCH_3$, —SO$_2$NH-alkyl, —SO$_2$NHCOCH$_3$, —SO$_2$NHCO-alkyl, —CO$_2$H, —CONHCH$_3$, —CONH-alkyl, —CO$_2$CH$_3$, —CO$_2$-alkyl, —CONHSO$_2$CH$_3$ and —CONHSO$_2$-alkyl, alkyl being as defined above for R$_1$, R$_2$; wherein at least one of the substituents on the A ring R$_3$, R$_4$, R$_5$, R$_6$ and R$_7$ is H; provided that when R$_1$ is methyl, R$_3$, R$_4$, R$_5$, R$_6$ and R$_7$ are H, and R$_2$ is not H or methyl.

When R$_1$ is H or R$_2$ is H, the isoprenyl, group of general formula (iv) can optionally cyclise to form a benzocondensed system of 2,2-dimethylchroman, giving a compound of general formula (v) or (vi):

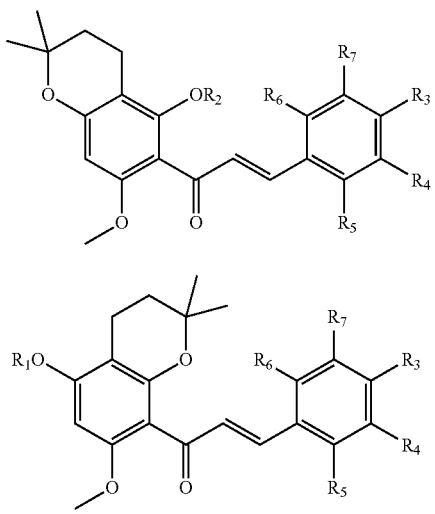

wherein R$_1$, R$_2$, R$_3$, R$_4$, R$_5$, R$_6$ and R$_7$ are as defined above for formula (iv).

In a preferred embodiment of the invention A is a phenyl ring, as in the compounds of general formula (iv), (v) and (vi).

In another preferred embodiment of the invention A is a 2-, 3- or 4-pyridyl ring.

R$_1$ and R$_2$ are preferably, independently of one another, hydrogen or methoxymethyl.

According to a preferred aspect of the invention, R$_3$, R$_4$, R$_5$, R$_6$ and R$_7$ are, independently of one another, H, —OCH$_3$, F, Cl, —NO$_2$, —CONHCH$_3$, —SO$_2$NH$_2$, —NHSO$_2$CH$_3$, or the —SO$_2$NHCOCH(Et)NHCOOCH$_2$Ph group; wherein at least one of R$_3$, R$_4$, R$_5$, R$_6$ and R$_7$ is H.

According to a further preferred aspect of the invention, A is phenyl or 2-, 3- or 4-pyridyl; R$_1$ and R$_2$ are, independently of one another, hydrogen or methoxymethyl, and R$_3$, R$_4$, R$_5$, R$_6$ and R$_7$ are, independently of one another, H, —OCH$_3$, F, Cl, —NO$_2$, —CONHCH$_3$, —SO$_2$NH$_2$, —NHSO$_2$CH$_3$, or the —SO$_2$NHCOCH(Et)NHCOOCH$_2$Ph group; wherein at least one of R$_3$, R$_4$, R$_5$, R$_6$ and R$_7$ is H.

The preferred compounds according to the invention are:
(E)-3-(3,4-dichloro-phenyl)-1-(6-methoxy-2,4-bis (methoxymethoxy)-3-(3-methylbut-2-enyl)phenyl)prop-2-en-1-one;
(E)-3-(3,4-dichloro-phenyl)-1-[2-hydroxy-6-methoxy-4-(methoxymethyloxy)-3-(3-methyl-but-2-enyl)-phenyl]-prop-2-en-1-one;
(E)-3-(3,4-dichloro-phenyl)-1-[2,4-dihydroxy-6-methoxy-3-(3-methyl-but-2-enyl)-phenyl]-prop-2-en-1-one;
(E)-3-(3,4-dichlorophenyl)-1-(5-hydroxy-7-methoxy-2,2-dimethylchroman-6-yl)prop-2-en-1-one;
(E)-3-(4-fluorophenyl)-1-[6-methoxy-2,4-di-methoxymethyloxy-3-(3-methyl-but-2-enyl)-phenyl]-prop-2-en-1-one;
(E)-1-[2,4-dihydroxy-6-methoxy-3-(3-methyl-but-2-enyl) prenyl]-3-(4-fluorophenyl)-prop-2-en-1-one;
(E)-3-(4-fluorophenyl)-1-[2-hydroxy-6-methoxy-4-(methoxymethyloxy)-3-(3-methyl-but-2-enyl]-phenyl) prop-2-en-1-one;
(E)-1-[6-methoxy-2,4-dimethoxymethyloxy)-3-(3-methyl-but-2-enyl)phenyl]-3-(4-nitrophenyl)prop-2-en-1-one;
(E)-1-[2-hydroxy-6-methoxy-4-(methoxymethyloxy)-3-(3-methylbut-2-enyl)phenyl]-3-(4-nitrophenyl)prop-2-en-1-one;
(E)-1-[2,4-dihydroxy-6-methoxy-3-(3-methylbut-2-enyl) phenyl]-3-(4-nitrophenyl)prop-2-en-1-one;
(E)-N-(4-{3-[6-methoxy-2,4-bis-methoxymethyloxy-3-(3-methyl-but-2-enyl)phenyl]-3-(oxoprop-1-enyl}phenyl)-acetamide;
(E)-N-(4-{3-[2-hydroxy-6-methoxy-4-methoxymethyloxy-3-(3-methyl-but-2-enyl)phenyl]-3-oxoprop-1-enyl}phenyl)acetamide;
(E)-N-(4-{3-[2,4-dihydroxy-6-methyloxy-3-(3-methyl-but-2-enyl}-3-oxoprop-1-enyl}-phenyl)acetamide;
(E)-3-(3,4-difluoro-phenyl)-1-[6-methoxy-2,4-bis-methoxymethyloxy-3-(3-methyl-but-2-enyl)phenyl-prop-2-en-1-one;
(E)-3-(3,4-difluorophenyl)-1-[2-hydroxy-6-methoxy-4-methoxymethyloxy-3-(3-methyl-but-2-enyl)phenyl]prop-2-en-1-one;
(E)-3-(3,4-difluorophenyl)-1-[2,4-dihydroxy-6-methoxy-3-(3-methyl-but-2-enyl)-phenyl]-prop-2-en-1-one;
(E)-3-(2,4-difluoro-phenyl)-1-[6-methoxy-2,4-dimethoxymethyloxy-3-(3-methyl-but-2-enyl)phenyl]-prop-2-en-1-one;
(E)-3-(2,4-difluoro-phenyl)-1-[2-hydroxy-6-methoxy-4-methoxymethyloxy-3-(3-methyl-but-2-enyl)-phenyl]-prop-2-en-1-one;
(E)-3-(2,4-difluoro-phenyl)-1-[4-hydroxy-6-methoxy-2-methoxymethyloxy-3-(3-methyl-but-2-enyl)-phenyl]-prop-2-en-1-one;
(E)-3-(2,4-difluoro-phenyl)-1-[2,4-dihydroxy-6-methoxy-3-(3-methyl-but-2-enyl)-phenyl]-prop-2-en-1-one;
1-[6-methoxy-2,4-bis-methoxymethoxy-3-(3-methyl-but-2-enyl)-phenyl]-3-pyridin-2-yl-propenone;
1-[2-hydroxy-6-methoxy-4-methoxymethoxy-3-(3-methyl-but-2-enyl)-phenyl]-3-pyridin-2-yl-propenone hydrochloride;
1-[4-hydroxy-6-methoxy-2-methoxymethoxy-3-(3-methyl-but-2-enyl)-phenyl]-3-pyridin-2-yl-propenone hydrochloride;
1-[2,4-dihydroxy-6-methoxy-3-(3-methyl-but-2-enyl)-phenyl]-3-pyridin-2-yl-propenone hydrochloride;
3-(5-chloro-pyridin-3-yl)-1-[6-methoxy-2,4-bis-methoxymethoxy-3-(3-methyl-but-2-enyl)-phenyl]-propenone;
3-(5-chloro-pyridin-3-yl)-1-[2-hydroxy-6-methoxy-4-methoxymethoxy-3-(3-methyl-but-2-enyl)-phenyl]-propenone hydrochloride;
3-(5-chloro-pyridin-3-yl)-1-[4-hydroxy-6-methoxy-2-methoxymethoxy-3-(3-methyl-but-2-enyl)-phenyl]-propenone hydrochloride;
3-(5-chloro-pyridin-3-yl)-1-[2,4-dihydroxy-6-methoxy-3-(3-methyl-but-2-enyl)-phenyl]-propenone hydrochloride;
1-[6-methoxy-2,4-bis-methoxymethoxy-3-(3-methyl-but-2-enyl)-phenyl]-3-pyridin-4-yl-propenone;
1-[2-hydroxy-6-methoxy-4-methoxymethoxy-3-(3-methyl-but-2-enyl)-phenyl]-3-pyridin-4-yl-propenone hydrochloride;

1-[4-hydroxy-6-methoxy-2-methoxymethoxy-3-(3-methyl-but-2-enyl)-phenyl]-3-pyridin-4-yl-propenone hydrochloride;

1-[2,4-dihydroxy-6-methoxy-3-(3-methyl-but-2-enyl)-phenyl]-3-pyridin-4-yl-propenone hydrochloride;

N-(4-{3-[6-methoxy-2,4-bis-methoxymethoxy-3-(3-methyl-but-2-enyl)-phenyl]-3-oxo-propenyl}-phenyl)-methanesulphonamide;

N-(4-{3-[2-hydroxy-6-methoxy-4-methoxymethoxy-3-(3-methyl-but-2-enyl)-phenyl]-3-oxo-propenyl}-phenyl)-methanesulphonamide;

N-(4-{3-[4-hydroxy-6-methoxy-2-methoxymethoxy-3-(3-methyl-but-2-enyl)-phenyl]-3-oxo-propenyl}-phenyl)-methanesulphonamide;

N-(4-{3-[2,4-dihydroxy-6-methoxy-3-(3-methyl-but-2-enyl)-phenyl]-3-oxo-propenyl}-phenyl)-methanesulphonamide;

2-chloro-5-{3-[2-hydroxy-6-methoxy-4-methoxymethoxy-3-(3-methyl-but-2-enyl)-phenyl]-3-oxo-propenyl}-benzenesulphonamide;

2-chloro-5-{3-[4-hydroxy-6-methoxy-2-methoxymethoxy-3-(3-methyl-but-2-enyl)-phenyl]-3-oxo-propenyl}-benzenesulphonamide;

2-chloro-5-{3-[2,4-dihydroxy-6-methoxy-3-(3-methyl-but-2-enyl)-phenyl]-3-oxo-propenyl}-benzenesulphonamide;

2-chloro-5-{3-[6-methoxy-2,4-bis-methoxymethoxy-3-(3-methyl-but-2-enyl)-phenyl]-3-oxo-propenyl}-benzenesulphonamide;

2-chloro-5-[3-(5-hydroxy-7-methoxy-2,2-dimethyl-chroman-6-yl)-3-oxo-propenyl]-benzenesulphonamide;

[1-(2-chloro-5-{3-[6-methoxy-2,4-methoxymethoxy-3-(3-methyl-but-2-enyl)-phenyl]-3-oxo-propenyl}-benzenesulphonylaminocarbonyl)-propyl]-benzyl-carbamate;

[1-(2-chloro-5-{3-[2,4-dihydroxy-6-methoxy-3-(3-methyl-but-2-enyl)-phenyl]-3-oxo-propenyl}-benzenesulphonylaminocarbonyl)-propyl]-benzyl-carbamate.

Further preferred compounds according to the invention are:

(E)-3-(2-fluorophenyl)-1-(6-methoxy-2-hydroxy-4-methoxymethoxy-3-(3-methylbut-2-enyl)phenyl)prop-2-en-1-one, [compound (58)];

(E)-3-(2-fluorophenyl)-1-(6-methoxy-2,4-dihydroxy-3-(3-methylbut-2-enyl)phenyl)prop-2-en-1-one, [compound (59)];

(E)-3-(3-fluoro-4-methoxyphenyl)-1-(6-methoxy-2,4-bis(methoxymethoxy)-3-(3-methylbut-2-enyl)phenyl)prop-2-en-1-one [compound (60)];

(E)-3-(3-fluoro-4-methoxyphenyl)-1-(6-methoxy-2-hydroxy-4-methoxymethoxy-3-(3-methylbut-2-enyl)phenyl)prop-2-en-1-one [compound (61)];

(E)-3-(3-fluoro-4-methoxyphenyl)-1-(6-methoxy-2,4-dihydroxy-3-(3-methylbut-2-enyl)phenyl)prop-2-en-1-one [compound (62)];

(E)-3-(2-fluoro-4-methoxyphenyl)-1-(6-methoxy-2,4-bis(methoxymethoxy)-3-(3-methylbut-2-enyl)phenyl)prop-2-en-1-one [compound (63)];

(E)-3-(2-fluoro-4-methoxyphenyl)-1-(6-methoxy-2-hydroxy-4-methoxymethoxy-3-(3-methylbut-2-enyl)phenyl)prop-2-en-1-one [compound (64)];

(E)-3-(2-fluoro-4-methoxyphenyl)-1-(6-methoxy-4-hydroxy-2-methoxymethoxy-3-(3-methylbut-2-enyl)phenyl)prop-2-en-1-one [compound (65)];

(E)-3-(2-fluoro-4-methoxyphenyl)-1-(6-methoxy-2,4-dihydroxy-3-(3-methylbut-2-enyl)phenyl)prop-2-en-1-one [compound (66)];

(E)-3-(4-nitrophenyl)-1-(6-methoxy-2-hydroxy-4-methoxymethoxy-3-(3-methylbut-2-enyl)phenyl)prop-2-en-1-one [compound (67)].

Further subjects of the present invention are tautomeric mixtures of the compounds of formula (i).

The present invention also relates to the pharmaceutically acceptable salts and prodrugs of the compounds of general formula (i).

Pharmaceutically acceptable salts comprise salts with alkaline metals and salts with free bases or acids. In general, said salts can be prepared by conventional methods. The pharmaceutically acceptable acids and bases used to form the salts according to the present invention can be inorganic or organic. The salts, preferably metal salts, can be formed with alkaline or alkaline earth metals or other salts with physiologically acceptable metals. The salts can be also formed with aluminium, calcium, lithium, magnesium, potassium, sodium and zinc. The preferred organic salts can be prepared from tertiary amines and quaternary ammonium salts.

The compounds according to the invention can also be used in the form of prodrugs, such as those obtained by reacting the compounds according to the invention containing —$NH_2$ or —COOH groups with alpha-amino acids or derivatives thereof protected at the amino or carboxyl group. The alpha-amino acids can be either natural or non-natural. An alpha-amino acid which can be used for the purposes of the present invention is N-benzyloxycarbonyl-2-aminobutyric acid.

The compounds according to the invention can be obtained by following the synthesis schemes described below.

The synthesis scheme illustrates a method of preparing compounds of general formula (i). The key points of the syntheses are a Mitsunobu reaction (b), a Claisen-Schmidt condensation (c) and the removal of the methoxymethyl (MOM) protecting group (g) when $R_1$ and/or $R_2$ is hydrogen. The first step (a) involves partial functionalisation of 2',4',6'-trihydroxyacetophenone, I (commercial product) with suitable halides $R_1X$ and $R_2X$ (wherein X can be chloro or bromo or iodo), alkyl sulphates $(R_1)_2SO_4$ and $(R_2)_2SO_4$, t-$BuMe_2SiCl$ (from which the corresponding ether t-$BuMe_2$ can easily be converted to alkyl ether wherein $R_1$ or $R_2$ is Me or Bn), diazomethane or diazoalkyls, under suitable basic conditions, using alkaline or neutral carbonates or hydroxides as bases (see, for example, protection of phenols in Wuts P. G. M. and Greene T., Greene's Protective Groups in organic synthesis, 5th edition, John Wiley & Sons 2007). Depending on the synthesis route, said group must be stable under basic conditions and easily removed under mild acidity conditions, or stable under acid conditions and easily removed under mild alkalinity conditions, or stable under both acid and basic conditions but removable by catalytic hydrogenation. These delicate deprotection conditions avoid spontaneous intramolecular cyclisations which give undesirable flavone structures.

Step (b) (Mitsunobu reaction) allows the introduction of the prenyl group onto intermediate 2, giving prenyl ether 3 with acceptable yields. In this reaction, phenol 2, solubilised in anhydrous THF or in a suitable anhydrous solvent, is reacted with the alcohol 3-methyl-2-buten-1-ol, diethylazadicarboxylate (DEAD) and triphenylphosphine (TPP). In some cases the yields of this step may be low, in which case the reaction is conducted with phenol 2 in anhydrous toluene, using DEAD as dehydrating agent and adding triphenylphosphine and 3-methyl-2-buten-1-ol in small portions. Under these new conditions, although the reaction times remain unchanged (about 20-24 h), the yield can be much better (up to 90-95%). Typically, the reaction can also be conducted with other solvents such as dichloromethane, acetonitrile, N-methylpyrrolidinone, benzene, m-xylene and mixtures thereof. The above reaction can also use other suitable condensing agents supported on polymer resins. Diisopropylazadicarboxylate (DIAD), 1,1'-azodicarbonyl-dipiperidine (ADDP), N,N,N',N'-tetramethylazodicarbox-amide (TMAD), tributylphosphine (PBu$_3$) and the like can also be used as condensing agents as well as DEAD and TPP.

The third step (c) involves a Claisen rearrangement to obtain the intermediate chalcone 4. Precursor 3, solubilised in N,N-dimethylaniline, is maintained for a time of between 1 and 48 hours, preferably 4 hours, at a temperature ranging between 60 and 240° C., preferably 200° C., under stirring, to obtain the product of transposition onto the para position of aromatic ring 4 with a 44% yield when R$_1$=R$_2$=methoxymethyl.

The fourth step (d) consists of methylation of the hydroxyl in the ortho position (position 6') using dimethyl-sulphate in the presence of potassium carbonate, to give derivative 5 with yields ranging between 45 and 70%.

Step (f) involves aldol condensation, which leads to the protected chalcone (E)-6 (50-62%).

From this, via a synthesis step of hydrolysis or controlled deprotection, such as conditions (g) if R$_1$ and/or R$_2$ is methoxymethyl, the compounds of general formula (i) are obtained as monodeprotected derivatives type 7a and 7b, and type 8 totally deprotected on the phenol groups in the 2 and 4 position on the phenyl substituted with the isoprenyl group. The controlled conditions allow the removal of group R$_1$ or R$_2$ or both, avoiding cyclisation to isoxanthohumols.

Synthesis scheme 1.

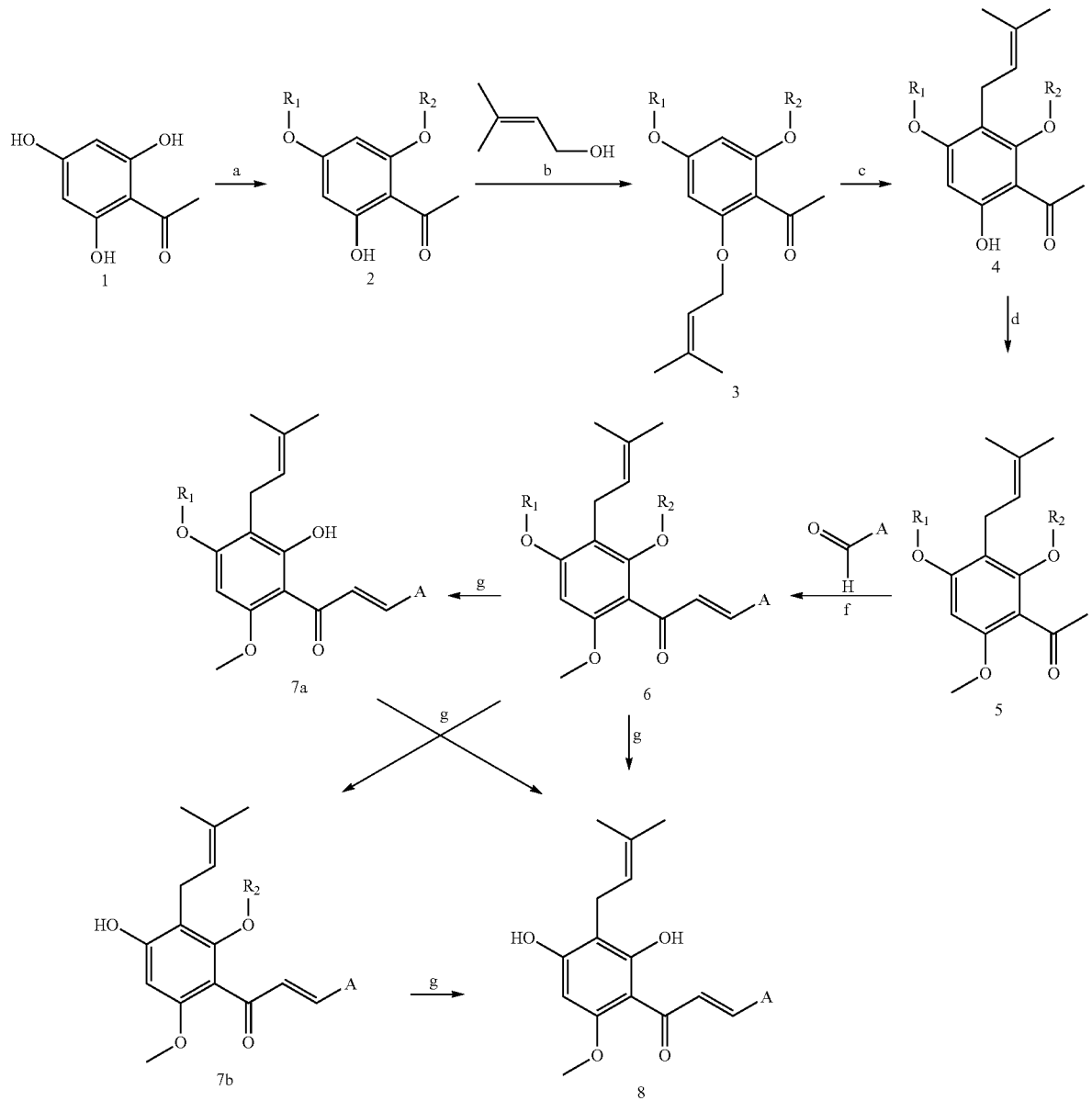

(a) R$_1$X, R$_2$X, base or other; (b) 3-methyl-2-buten-1-ol, DEAD, PPh$_3$, THF/toluene or other; (c) N,N-dimethylaniline, reflux, 200° C.; (d) (CH$_3$O)$_2$SO$_2$, K$_2$CO$_3$, acetone, reflux, 60° C.; (e) mono/disubstituted arylaldehyde; (f) aqueous NaOH, MeOH, reflux, 65° C.; (g) HCl/MeOH (1.25M).

The compounds of formula (i), wherein A is a monocyclic aryl substituted in the 4 position by a methoxyl group and in the 2 or 3 position by a fluorine atom can also be obtained by reacting the compounds of formula (i), wherein A is a monocyclic difluoro aryl substituted in the 3,4 or 2,4 positions with sodium methylate or potassium methylate, under the classic conditions used for aromatic nucleophilic substitution reactions.

Derivatives of type (ii) and (iii) can be obtained from the compounds of type (i), 7a or (i), 7b under appropriate acid conditions (pH=1 in appropriate water-alcohol solvent mixtures) and temperature conditions, as reported in synthesis scheme 2. Under certain conditions the cyclisation reaction is possible or facilitated by using microwaves in an appropriate solvent or solvent mixture. Under certain conditions, mixtures of type (i) compounds can be obtained together with the type (ii) or (iii) cyclised compounds, and then easily separated by chromatography. n-propanol, isopropanol, n-butanol, isobutanol, cyclohexanol and various glycols can be used as alcoholic solvents, depending on the necessary conditions, in addition to methanol (MeOH).

Synthesis scheme 2

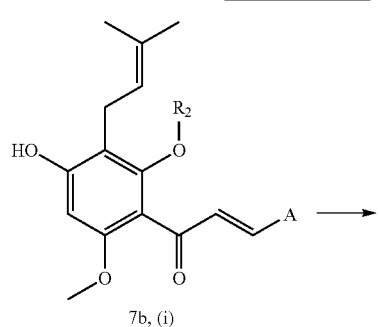

7b, (i)

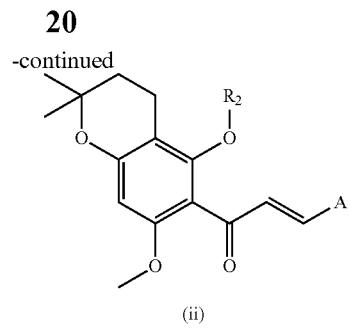

(ii)

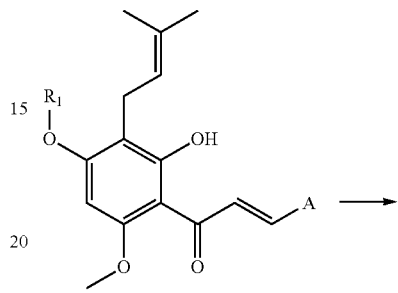

7a, (i)

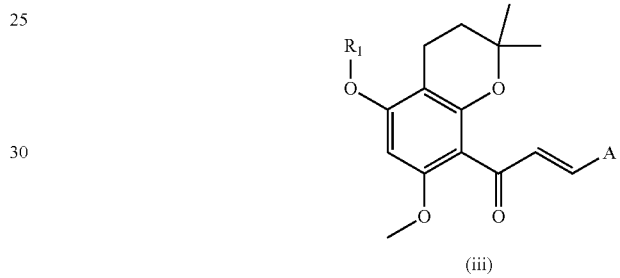

(iii)

The synthesis of type (i-vi) isoprenylated chalcone analogue structures is therefore possible on these bases.

Synthesis scheme 3

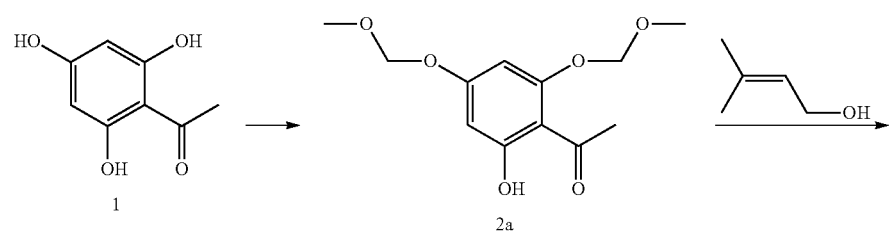

1    2a

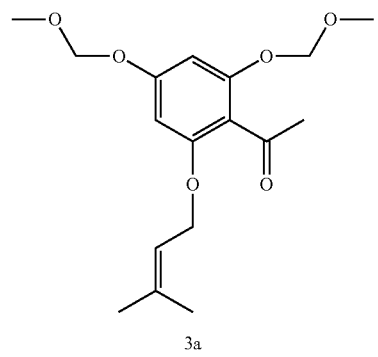

3a

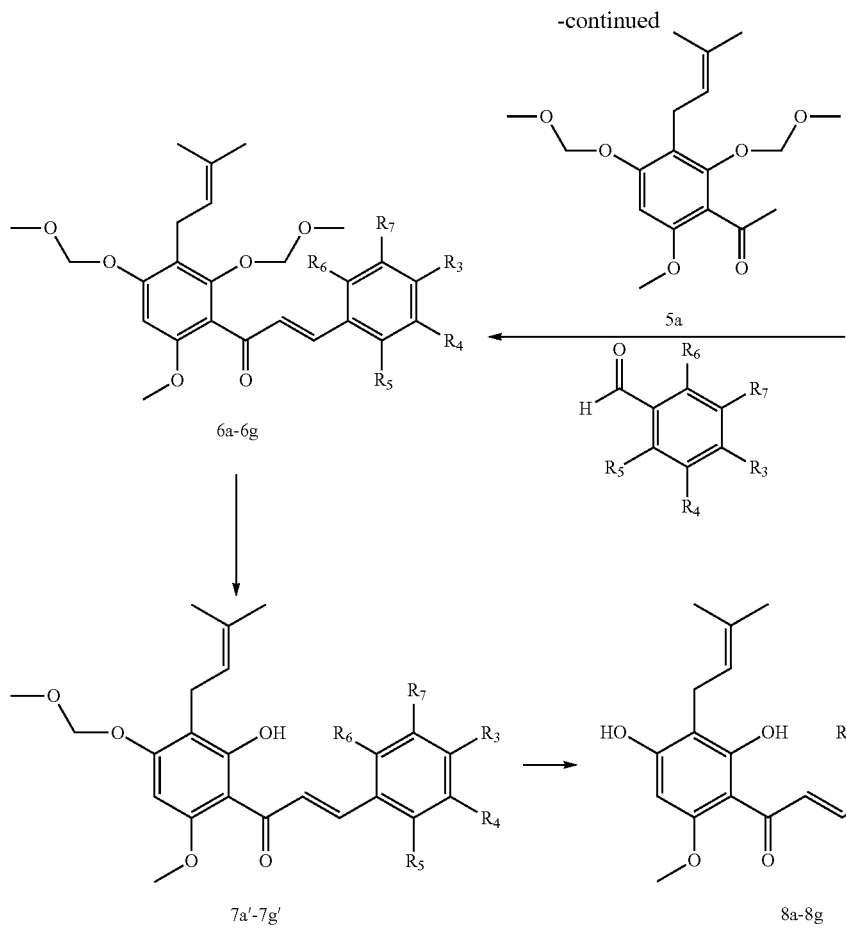
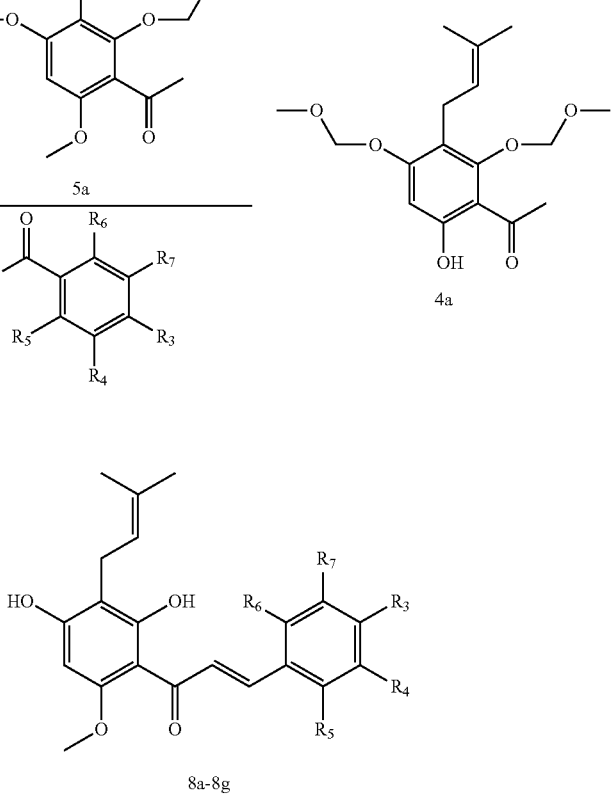

The partial protection of 2',4',6'-trihydroxyacetophenone 1 with methoxymethylchloride (MOMCl) using DIPEA as base in DCM as solvent leads to di-MOM derivative 2a with yields of 66%. A subsequent Mitsunobu reaction using phenol 2a in the presence of 3-methyl-2-buten-1-ol with DEAD as dehydrating agent and TPP allows the introduction of the prenyl group, giving prenyl ether 3a (1-[2,4-dimethoxymethyloxy-6-(3-methyl-but-2-enyloxy)-phenyl]-ethanone) with yields of 38%. A subsequent Claisen rearrangement of allyl ether 3a in N,N-dimethylaniline at 200° C. for 4 hours gives chalcone 4a, 1-[6-hydroxy-2,4-dimethoxymethyloxy-3-(3-methyl-but-2-enyl)-phenyl]-ethanone, with yields of 44%. Subsequently, methylation of 4a with dimethylsulphate in the presence of potassium carbonate gives the desired key intermediate 5a (1-[6-methoxy-2,4-dimethoxymethyloxy-3-(3-methyl-but-2-enyl)-phenyl]-ethanone), with yields of 62%.

At this point, an aldol condensation using an appropriate aldehyde, conducted in methanol using 10% aqueous sodium hydroxide as base, gives di-MOM substituted 6-methoxy chalcone intermediates (E)-6a-(E)-6g with yields of around 60%. Subsequently, by deprotection of MOM under controlled temperature and acidity conditions, the mono-MOM substituted chalcones (E)-7a'-(E)-7g' are obtained, mixed with deprotected XN analogue chalcones with suitable 8a-8g substitutions on the B ring. Appropriate chromatography conditions on Isolute Flash (Biotage) or Flash silica gel columns allow the isolation of both the mono MOM derivatives of type (1), (E)-7a'-(E)-7g' and the desired deprotected chalcones of type (1), 8a-8g (Synthesis scheme 3).

The compounds according to the invention exhibit anti-proliferative effects against human tumour lines, such as breast cancer, hepatocarcinoma, prostate carcinoma, myeloma and leukaemia lines.

The compounds according to the invention also inhibit the proliferation of human umbilical vein endothelial cells (HUVEC).

The compounds according to the invention also inhibit the chemotaxis and invasion of HUVEC and human tumour cell lines, such as breast cancer and fibrosarcoma cells.

The compounds according to the invention therefore possess anti-angiogenic, antioxidant and chemopreventive properties.

The anti-proliferative, anti-invasive and anti-angiogenic activity possessed by the compounds according to the invention is greater than the activities exhibited by XN when used as control in parallel experiments.

The compounds according to the invention modulate the catalytic activity of extracellular matrix metalloproteases, especially between MMP-2 and MMP-9, with different selectivities from XN.

A further subject of the present invention is the use of the compounds according to the invention as medicaments.

In particular, the compounds according to the invention can be used in the prevention and/or treatment of tumoral, inflammatory, cardiovascular or neurodegenerative disorders, or as angiogenesis inhibitors, for example in the prevention and/or treatment of tumour angiogenesis.

The compounds according to the invention can be suitably formulated with pharmaceutically acceptable excipients or carriers. The suitable pharmaceutical forms can vary according to the specific compound and the administration route. The dose of active ingredient will be determined on each occasion, according to the severity of the disorder to be treated and the patient's general condition. Suitable pharmaceutical compositions can be prepared in accordance with the indications reported in Remington's Pharmaceutical Sciences, 18th ed., Mack Publishing Co.

The examples given below further illustrate the invention.

EXAMPLES

Materials and Methods

All the reactions were conducted under nitrogen, in anhydrous solvents. The structure of the compounds was established by 1H-NMR, 13C-NMR and mass spectrometry. The nuclear magnetic resonance spectra were recorded on a Varian Gemini 200 spectrometer operating at 200 MHz for 1H and 50.3 MHz for 13C in CDCl3, DMSO-d6, acetone-d6, D2O and MeOD; the chemical shifts (δ) are expressed in ppm. The reaction solvents were evaporated under vacuum in a rotary evaporator, while anhydrous $Na_2SO_4$ was used as drying agent for the organic solvent solutions. The preparatory liquid chromatographies were conducted with flash chromatography on prepacked (Biotage) Isolute Si II columns or on columns packed by us containing 230-400 mesh silica gel. The thin-layer chromatographies (TLC) were conducted with 60 F254 (MERCK) silica gel plates containing a fluorescent indicator. The various spots were highlighted with a UV lamp (256 nM). The melting points were determined under the Kofler microscope.

Preparation Example 1: Preparation of 1-(2-hydroxy-4,6-dimethoxymethyloxy-phenyl)-ethanone [compound (2)]

Diisopropylethylamine, DIPEA (8.4 mL, 48.327 mmols), followed by MOM chloride (3.7 mL, 48.327 mmols), was added drop by drop to a suspension, stirred and cooled in an ice bath, of 2',4'6'-trihydroxyacetophenone monohydrate, 1, (3 g, 16.115 mmols), in anhydrous CH2Cl2 (36 mL). When the addition was complete, the temperature was gradually increased to RT, and the reaction was maintained under stirring, under these conditions, for 6 h. After that time the reaction mixture was returned to the ice bath and treated with a saturated aqueous solution of ammonium chloride (30 mL). The reaction was then heated to RT and left under stirring for 30 min. The resulting mixture was then extracted with CH2Cl2/water [3×100 mL (1:1)], and the resulting separated organic phase was dried on sodium sulphate, filtered and evaporated. The dark crude oil obtained (4.268 g) was then purified, after adsorption on 4.50 g of silica 230-400 mesh, by flash chromatography on silica gel column (silica 230-400 mesh, diameter 4 cm, height 17 cm) using n-hexane/AcOEt (6:1) as eluent, and collecting 12 mL fractions. 2.716 g of 2 in the form of a thick, transparent oil, tending to solidify at low temperature, was obtained from the fractions (test tubes 5-30, Vm: 500 mL).

Yield: 66%

TLC Rf: 0.16 in n-hexane/AcOEt (5:1);

1H-NMR (200 MHz, CDCl3): 6.27 (d, 1H, J=2.2 Hz, Ar—H), 6.24 (d, 1H, J=2.2 Hz, Ar—H), 5.25 (s, 2H, O—CH2-O), 5.17 (s, 2H, O—CH2-O), 3.51 (s, 3H, OCH3), 3.47 (s, 3H, OCH3), 2.66 (s, 3H, COCH3).

Preparation Example 2: Preparation of 1-[2,4-dimethoxymethyloxy-6-(3-methyl-but-2-enyloxy)-phenyl]-ethanone [compound (3)]

Procedure A

Triphenyl phosphine (1.879 g, 7.165 mmols, 1.2 equiv) and the alcohol 3-methyl-2-buten-1-ol (0.9 mL, 8.956 mmols, 1.5 equiv) were added to a solution of 1-(2-hydroxy-4,6-dimethoxyphenyl)ethanone, 2 (1.530 g, 5,971 mmols, 1 equiv) in tetrahydrofuran (30 mL), placed under stirring in an ice bath. The DEAD (1.5 ml, 9.554 mmols, 1.6 equiv) was dripped and the solution was heated to RT and left under stirring for 21 h. The solvent was then evaporated and the residue suspended in ethyl ether, in which the formation of a white crystalline precipitate was observed. The solid was filtered under vacuum and the filtrate evaporated, to obtain 11.725 g of a sticky yellow oil with a pungent odour, purified with a flash chromatography column on silica gel (silica 230-400 mesh, diameter 6 cm, height 18 cm) after preparation of the absorbate (silica 230-400 mesh, 12.0 g). The eluent mixture used for the resolution of the column was n-hexane/AcOEt in the ratio of 6:1. 0.738 g of 13, which appeared as a clear oil, was obtained from evaporation of the organic fraction (test tubes 41-78, 12 mL fractions, Vm: 1100 mL).

Yield: 38%

TLC Rf: 0.36 in n-hexane/AcOEt 7:1;

1H-NMR (200 MHz, CDCl3): 6.44 (d, 1H J=2.01 Hz, Ar—H), 6.31 (d, 1H, J=2.01 Hz, Ar—H), 5.4 (t, 1H, J=6.6 Hz, CH=), 5.14 (s, 2H, O—CH2-O), 5.12 (s, 2H, O—CH2-O), 4.49 (d, 2H, J=6.6 Hz, CH2), 3.47 (s, 3H, OCH3), 3.45 (s, 3H, OCH3), 2.47 (s, 3H, COCH3), 1.75 (s, 3H, CH3), 1.70 (s, 3H, CH3).

Procedure B

Triphenyl phosphine (2.068 g, 7.884 mmols, 1.4 equiv) and the alcohol 3-methyl-2-buten-1-ol (1.1 ml, 11.238 mmols, 2 equiv) were added to a solution of 1-(2-hydroxy-4,6-dimethoxyphenyl)ethanone, 2 (1.440 g, 5.619 mmols, 1 equiv) in toluene (29 mL), placed under stirring in an ice bath. The DEAD (1.8 mL, 11.238 mmols, 2 equiv) was dripped and the solution was heated to RT and left under stirring for 21 h. The solvent was then evaporated and the residue suspended in ethyl ether, in which the formation of a white crystalline precipitate was observed. The solid was filtered under vacuum and the filtrate evaporated, to obtain a sticky yellow oil with a pungent odour (6.260 g). The crude product was purified with a flash chromatography column on silica gel (silica 230-400 mesh, diameter 6 cm, height 17 cm) after preparation of the absorbate (silica 230-400 mesh, 7.0 g). The eluent mixture used for the resolution of the column was n-hexane/AcOEt in the ratio of 7:1. 1.660 g of 3, which presented as a pale oil, was obtained from evaporation of the organic fraction (test tubes 72-123, 15 mL fractions, Vm: 750 mL).

Yield: 91%

TLC Rf: 0.36 in n-hexane/AcOEt 7:1;

1H-NMR (200 MHz, CDCl3): 6.44 (d, 1H J=2.01 Hz, Ar—H), 6.31 (d, 1H, J=2.01 Hz, Ar—H), 5.4 (t, 1H, J=6.6 Hz, CH=), 5.14 (s, 2H, O—CH2-O), 5.12 (s, 2H, O—CH2-O), 4.49 (d, 2H, J=6.6 Hz, CH2), 3.47 (s, 3H, OCH3), 3.45 (s, 3H, OCH3), 2.47 (s, 3H, COCH3), 1.75 (s, 3H, CH3), 1.70 (s, 3H, CH3).

Preparation Example 3: Preparation of 1-[6-hydroxy-2,4-dimethoxymethyloxy-3-(3-methyl-but-2-enyl)-phenyl]-ethanone [compound (4)]

A solution of 1-[2,4-dimethoxymethyloxy-6-(3-methyl-but-2-enyloxy)-phenyl]-ethanone 3 (0.300 g, 0.925 mmols) in N,N-dimethylaniline (8 mL, 0.063 mmols) was heated to 200° C. and maintained at that temperature for 4 h. After this interval, the resulting mixture was cooled to room temperature and extracted with AcOEt/HCl [4×100 ml (1:1)], and the separated organic phase was dried on sodium sulphate, filtered and evaporated. The residue, a dark, almost black, sticky oil (0.383 g), only soluble in CHCl$_3$, was chromatographed on silica (silica 230-400 mesh, diameter 4 cm, height 20 cm) after preparation of the absorbate (silica 230-400 mesh, 0.500 g). n-hexane/AcOEt in the ratio of 7:1 was selected as eluent mixture. 0.075 g of 4, which presented as a bright yellow oil, was obtained from evaporation of the organic fraction (test tubes 16-20, 12 ml fractions, Vm: 150 ml).

Yield: 44%

TLC Rf: 0.39 in n-hexane/AcOEt 5:1

1H-NMR: (200 MHz, CDCl3): δ 6.53 (s, 1H, Ar—H), 5.20 (s, 2H, O—CH2-O), 5.13 (t, 1H, J=6.6 Hz, CH=), 4.90 (s, 2H, O—CH2-O), 3.79 (s, 3H, OCH3), 3.48 (s, 3H, OCH3), 3.30 (d, 2H, J=6.6 Hz, CH2), 2.49 (s, 3H, COCH3), 1.74 (s, 3H, CH3), 1.65 (s, 3H, CH3).

Preparation Example 4: Preparation of 1-[6-methoxy-2,4-dimethoxymethyloxy-3-(3-methyl-but-2-enyl)-phenyl]-ethanone [compound (5)]

Potassium carbonate (0.407 g, 2.948 mmols, 2 equiv) and dimethyl sulphate (0.3 mL, 2.948 mmols, 2 equiv) were added to a solution, placed under stirring, of 1-[6-hydroxy-2,4-dimethoxymethyloxy-3-(3-methyl-but-2-enyl)-phenyl]-ethanone (4) (0.478 g, 1.474 mmols, 1 equiv) in acetone (25 mL). The reaction was maintained under stirring at 60° C. for 6 h. The reaction was then heated to RT and quenched with a 30% aqueous solution of NH$_3$ (28 mL). The resulting mixture was then extracted with CH$_2$Cl$_2$/water [3×60 mL (1:1)], and the resulting separated organic phase was dried on sodium sulphate and evaporated. The residue, a bright yellow oil (0.475 g), was chromatographed on an Isolute Si II 20 g flash chromatography column using n-hexane/AcOEt 9:1. 0.380 g (1.123 mmols) of 5, a dark yellow oil, was obtained from evaporation of the organic fraction (test tubes 31-52, 5 ml fractions).

Yield: 76%

TLC Rf: 0.38 in n-hexane/AcOEt 3:1

1H-NMR: (200 MHz, CDCl3): δ 6.54 (s, 1H, Ar—H), 5.21 (s, 2H, O—CH2-O), 5.14 (t, 1H, J=6.6 Hz, CH=), 4.90 (s, 2H, O—CH2-O), 3.79 (s, 3H, OCH3), 3.48 (s, 3H, OCH3), 3.47 (s, 3H, OCH3), 3.27 (d, 2H, J=6.6 Hz CH2), 2.50 (s, 3H, COCH3), 1.75 (s, 3H, CH3), 1.66 (s, 3H, CH3).

Example 5: Preparation of (E)-3-(3,4-dichlorophenyl)-1-(6-methoxy-2,4-bis(methoxymethoxy)-3-(3-methylbut-2-enyl)phenyl)prop-2-en-1-one [compound (6)]

(6)

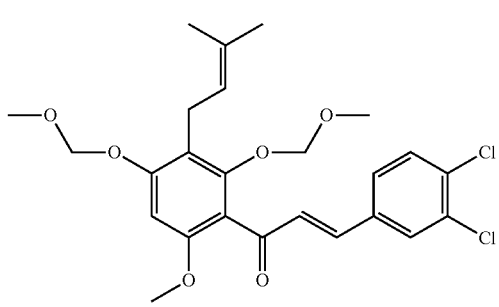

A 10% saturated aqueous solution of NaOH (1 mL) was added to a solution, placed under stirring, of 1-[6-methoxy-2,4-dimethoxymethyloxy-3-(3-methyl-but-2-enyl)-phenyl]-ethanone, 5 (0.180 g, 0.53 mmols) and 3,4-dichlorobenzaldehyde (0.0927 g, 0.53 mmols) in anhydrous methanol (21 mL). The reaction temperature was increased to 65° C. and maintained for 6 h. The reaction was then restored to RT, extracted with AcOEt (100 mL) and washed with H2O [3×50 mL]0.1)]. The separated organic phase was dried on sodium sulphate, filtered and evaporated, to obtain a yellow oil (0.278 g). The crude product was purified on an Isolute Si II 10g flash chromatography column using n-hexane/AcOEt 12:1 as eluent. When the organic fraction had been evaporated (test tubes 25-36, 5 mL fractions), a fluorescent yellow semisolid 6 (0.163 g) was obtained.

Yield: 62%

TLC Rf: 0.26 in n-hexane/AcOEt 7:1.

1H-NMR (200 MHz, CDCl3): δ 7.60 (d, 1H, J=16 Hz, =CHAr—H), 7.38 (t, 2H, J=16 Hz, =CHAr—H), 7.28 (d, 1H, J=16 Hz, CH=), 6.92 (d, 1H, J=15.9 Hz, CH=), 6.59 (s, 1H, Ar—H), 5.24 (s, 2H, O—CH2-O), 5.14 (t, 1H, J=6.9 Hz, CH2CH=), 4.90 (s, 2H, O—CH2-0), 3.77 (s, 3H, OCH3), 3.50 (s, 3H, CH2OCH3), 3.41 (s, 3H, CH2OCH3), 3.32 (d, 2H, J=6.9 Hz, CH2), 1.76 (s, 3H, CH3), 1.68 (s, 3H, CH3).

Example 6: Preparation of (E)-3-(3,4-dichloro-phenyl)-1-[2-hydroxy-6-methoxy-4-(methoxymethyloxy)-3-(3-methyl-but-2-enyl)-phenyl-prop-2-en-1-one [compound (7)]

(7)

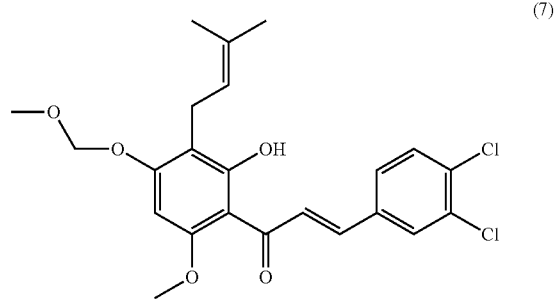 [SMILES: COCOc1cc(OC)c(C(=O)/C=C/c2ccc(Cl)c(Cl)c2)c(O)c1CC=C(C)C]

Concentrated HCl was added to a solution, placed under stirring, of (6) (0.100 g, 0.2 mmols) in MeOH/H20 (12 mL:1.3 mL) until the pH reached 1. The resulting mixture was left to react at RT for 12 h, and then extracted with AcOEt/H2O (1:1). The organic phase was dried on sodium sulphate, filtered and evaporated at 20° C., to obtain an orange solid (0.094 g). The crude product was crushed with Et2O/n-hexane to give 7 (0.082 g), an orange solid.

TLC Rf: 0.5 in n-hexane/AcOEt 6:1, MP: 230-235° C.

1H-NMR (200 MHz, CDCl3): δ 7.82 (d, 1H, J=15.7 Hz, =CHAr—H), 7.61 (d, 1H, J=15.7 Hz, CH=), 7.47 (d, 1H, J=8.4 Hz, Ar—H), 7.39 (d, 1H, J=8.4 Hz, ArH), 7.38 (2d, 1H, J=1.83 e 8.4 Hz, Ar—H), 6.24 (s, 1H, ArH), 5.27 (s, 2H, O—CH2-O), 5.17 (t, 1H, J=6.9 Hz, CH=), 3.90 (s, 3H, OCH3), 3.49 (s, 3H, CH2OCH3), 3.30 (d, 2H, J=6.9 Hz, CH2), 1.78 (s, 3H, CH3), 1.67 (s, 3H, CH3).

The NMR analysis demonstrated that only one of the two protecting groups of 6, namely the one in the 2 position, was hydrolysed.

Example 7: Preparation of (E)-3-(3,4-dichloro-phenyl)-1-[2,4-dihydroxy-6-methoxy-3-(3-methyl-but-2-enyl)-phenyl]-prop-2-en-1-one [compound (8a)] (chalcone 8) and (E)-3-(3,4-dichlorophenyl)-1-(5-hydroxy-7-methoxy-2,2-dimethylchroman-6-yl)prop-2-en-1-one [compound (8b)]

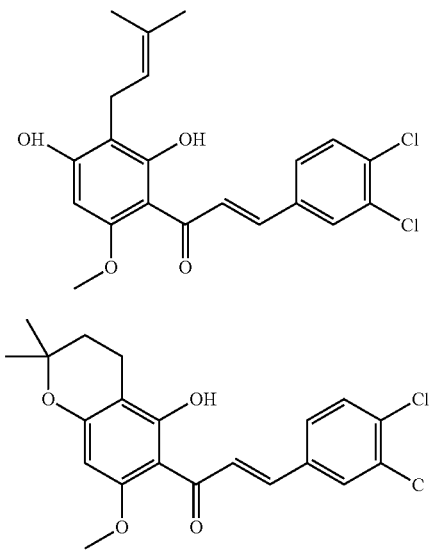

The procedure described in example 6 was repeated at a higher reaction temperature.

Concentrated HCl was added to a solution of (E)-3-(3,4-dichlorophenyl)-1-[2-hydroxy-6-methoxy-4-(methoxymethyloxy)-3-(3-methyl-but-2-enyl)-phenyl]-prop-2-en-1-one, 7 (0.072 g, 0.16 mmols) in MeOH/H20 (12 mL:1.3 mL) until the pH reached 1. The reaction mixture was heated to 40° C. and left under stirring for 48 h. The resulting mixture was then extracted with AcOEt/H2O (1:1). The organic phase was dried on sodium sulphate, filtered and evaporated at 20° C., to obtain an orange solid (0.066 g). The crude product was chromatographed on a an Isolute Si II 5 g flash chromatography column, using n-hexane/AcOEt in the ratio of 7:1 as eluent mixture. 8a (0.008 g) was obtained from evaporation of the organic fraction (test tubes 5-10, 5 mL fractions) as a yellow solid. 8b (0.004 g) was obtained from evaporation of test tubes 1-3 (5 mL fractions) as a yellow oil.

TLC (8a) Rf: 0.17 in n-hexane/AcOEt 7:1, MP: 240-246° C.

1H-NMR (200 MHz, CDCl3): δ 7.83 (d, 1H, J=15.6 Hz, CH=), 7.61 (d, 1H, J=15.6 Hz, CH=), 7.58 (d, 1H, J=8.3 Hz, =CHAr—H), 7.37 (m, 1H, =CHAr—H), 6.28 (s, 1H, Ar—H), 5.92 (d, 1H, OH), 5.28 (t, 1H, J=7.1 Hz, CH2CH=), 3.88 (s, 3H, OCH3), 3.88 (d, 2H, J=7.1 Hz, CH2), 1.83 (s, 3H, CH3), 1.77 (s, 3H, CH3).

TLC (8b) Rf: 0.87 in n-hexane/AcOEt 2:1

1H-NMR (200 MHz, CDCl3): δ 7.84 (d, 1H, J=16 Hz, CH=), 7.57 (d, 1H, J=16 Hz, CH=), 7.4 (d, 1H, J=8 Hz, =CHAr—H), 7.37 (d, 1H, J=8 Hz, =CHAr—H), 5.88 (s, 1H, Ar—H), 5.86 (s, 1H, OH), 3.88 (s, 3H, OCH3), 2.63 (t, 2H, J=4 Hz, CH2), 1.81 (t, 2H, J=4 Hz, CH2), 1.36 (s, 3H, CH3), 1.25 (s, 3H, CH3).

Example 8: Preparation of (E)-3-(4-fluorophenyl)-1-[6-methoxy-2,4-di-methoxymethyloxy-3-(3-methyl-but-2-enyl)-phenyl]-prop-2-en-1-one [compound (9)]

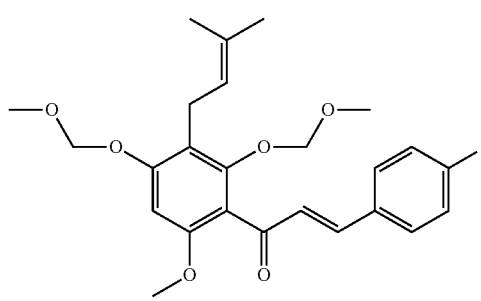

A 10% aqueous solution of NaOH (2 mL) was added to a suspension of 1-[6-methoxy-2,4-dimethoxymethyloxy-3-(3-methyl-but-2-enyl)-phenyl]-ethanone (5) (0.285 g, 0.842 mmols, 1 equiv) and 4-fluorobenzaldehyde (0.09 mL, 0.842 mmols, 1 equiv) in MeOH (33 mL), placed under stirring. The reaction mixture was heated to 65° C. and maintained under the same conditions for 6 h. It was then extracted with AcOEt (100 ml) and washed with H2O (3×50 mL). The organic phase was dried on sodium sulphate, filtered and evaporated, to obtain a yellow oil (0.183 g). The crude reaction product was purified on a an Isolute Si II 10 g flash chromatography column using n-hexane/AcOEt 14:1 as eluent mixture. 9 (0.091 g), a bright yellow oil, was obtained from evaporation of the organic fraction (test tubes 23-27, 5 mL fractions).

Yield: 25%

TLC Rf: 0.29 in n-hexane/AcOEt 5:1

1H-NMR (200 MHz, CDCl3): δ 7.49 (2d, 2H, J=8.4 Hz, =CHAr—H), 7.34 (d, 1H, J=16 Hz, CH=), 7.02 (2d, 2H, J=8.4 Hz, =CHAr—H), 6.88 (d, 1H, J=16 Hz, CH=), 6.59 (s, 1H, Ar—H), 5.24 (s, 2H, O—CH2-O), 5.18 (t, 1H, J=6.9 Hz, CH2CH=), 4.91 (s, 2H, O—CH2-0), 3.76 (s, 3H, OCH3), 3.50 (s, 3H, CH2OCH3), 3.42 (s, 3H, CH2OCH3), 3.33 (d, 2H, J=6.9 Hz, CH2), 1.76 (s, 3H, CH3), 1.67 (s, 3H, CH3).

Example 9: Preparation of (E)-1-[2,4-dihydroxy-6-methoxy-3-(3-methyl-but-2-enyl)prenyl]-3-(4-fluorophenyl)-prop-2-en-1-one [compound (10)] and (E)-3-(4-fluorophenyl)-1-[2-hydroxy-6-methoxy-4-(methoxymethyloxy)-3-(3-methyl-but-2-enyl]-phenyl)prop-2-en-1-one [compound (11)]

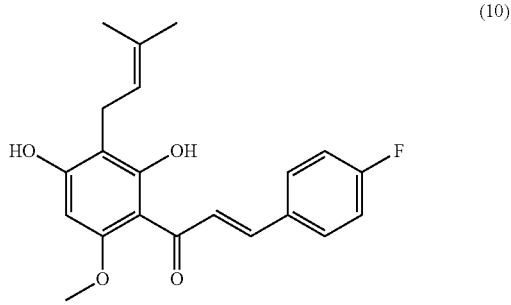

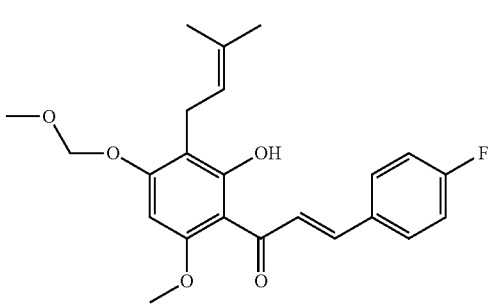

A solution of (E)-3-(4-fluorophenyl)-1-[6-methoxy-2,4-di-methoxymethyloxy-3-(3-methyl-but-2-enyl)-phenyl]-prop-2-en-1-one, 9 (0.091 g, 0.205 mmols) in MeOH/HCl 1.25 M (2.5 mL) was heated to 45° C. and left under stirring for 45 min. It was then extracted with AcOEt (100 mL) and washed with H2O (3×50 mL). The organic phase was dried on sodium sulphate, filtered and evaporated at 20° C., to obtain a golden yellow solid (0.074 g). The crude product was purified after adsorption on silica (silica 230-400 mesh, 0.080 g) by flash chromatography on silica gel column (silica 230-400 mesh, diameter 2 cm, height 15 cm) using n-hexane/EtOAc 7:1. 11 (0.006 g) was obtained as an orange oil and 10 (0.021 g) as a golden yellow solid from evaporation of the organic fractions (test tubes 8-10, test tubes 16-33, 8 mL fractions).

TLC (11) Rf: 0.16 in n-hexane/AcOEt 5:1

1H-NMR (200 MHz, CDCl3): δ 7.82 (d, 1H, J=15.4 Hz, CH=), 7.70 (d, 1H, J=15.4 Hz, CH=), 7.59 (2d, 2H, J=8.0 Hz, =CHAr—H), 7.13 (2d, 2H, J=8.0 Hz, =CHAr—H), 6.24 (s, 1H, Ar—H), 5.27 (s, 2H, O—CH2-O), 5.24 (t, 1H, J=6.8 Hz, CH2CH=), 3.93 (s, 3H, OCH3), 3.50 (s, 3H, CH2OCH3), 3.31 (d, 2H, J=6.8 Hz, CH2), 1.79 (s, 3H, CH3), 1.67 (s, 3H, CH3).

TLC (10) Rf: 0.28 in n-hexane/AcOEt 2:1, MP: 235-237° C.

1H-NMR (200 MHz, CDCl3): δ 7.82 (d, 1H, J=15.4 Hz, CH=), 7.70 (d, 1H, J=15.4 Hz, CH=), 7.59 (2d, 2H, J=8.0 Hz, =CHAr—H), 7.13 (2d, 2H, J=8.0 Hz, =CHAr—H), 6.24 (s, 1H, Ar—H), 5.27 (s, 2H, O—CH2-O), 5.24 (t, 1H, J=6.8 Hz, CH2CH=), 3.93 (s, 3H, OCH3), 3.50 (s, 3H, CH2OCH3), 3.31 (d, 2H, J=6.8 Hz, CH2), 1.79 (s, 3H, CH3), 1.67 (s, 3H, CH3).

Example 10: Preparation of (E)-1-[6-methoxy-2,4-dimethoxymethyloxy)-3-(3-methylbut-2-enyl)phenyl]-3-(4-nitrophenyl)prop-2-en-1-one [compound (12)]

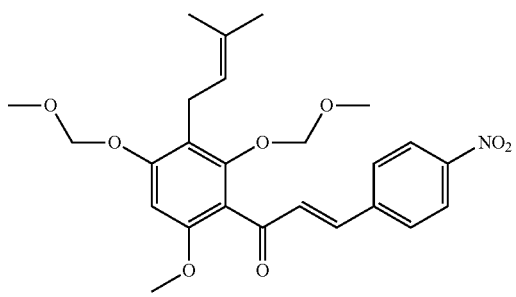

A 10% aqueous solution of NaOH (1.5 mL) was added to a solution of 1-[6-methoxy-2,4-dimethoxymethyloxy-3-(3-methyl-but-2-enyl)-phenyl]-ethanone, 5 (0.225 g, 1.330 mmols, 1 equiv) and 4-nitrobenzaldehyde (0.201 g, 1.330 mmols, 1 equiv) in MeOH (26 mL). The reaction mixture was heated to 65° C. and maintained under the same conditions and under stirring for 6 h. It was then extracted with AcOEt (100 mL) and washed with H2O (4×50 mL). The organic phase was dried on sodium sulphate, filtered and evaporated. The brown crude oil (0.382 g) was purified on an Isolute Si II 10 g flash chromatography column, using an n-hexane/AcOEt 6:1 eluent mixture. When the organic fraction (test tubes 20-44, 5 mL fractions) had evaporated, a yellow oil 12 (0.274 g) was obtained.

Yield: 44%

TLC Rf: 0.14 in n-hexane/AcOEt 4:1.

1H-NMR (200 MHz, CDCl3): δ 8.24 (d, 2H, J=8 Hz, =CHAr—H), 7.70 (d, 2H, J=8 Hz, =CHAr—H), 7.47 (d, 1H, J=16.2 Hz, CH=), 7.11 (d, 1H, J=16.2 Hz, CH=), 6.61 (s, 1H, Ar—H), 5.26 (s, 2H, O—CH2-O), 5.16 (t, 1H, J=6.8 Hz, CH2CH=), 4.91 (s, 2H, O—CH2-O), 3.79 (s, 3H, OCH3), 3.51 (s, 3H, CH2OCH3), 3.43 (s, 3H, CH2OCH3), 3.25 (d, 1H, J=6.8 Hz, CH2), 1.77 (s, 3H, CH3), 1.73 (s, 3H, CH3).

Example 11: Preparation of (E)-1-[2-hydroxy-6-methoxy-4-(methoxymethyloxy)-3-(3-methylbut-2-enyl)phenyl]-3-(4-nitrophenyl)prop-2-en-1-one [compound (13)]

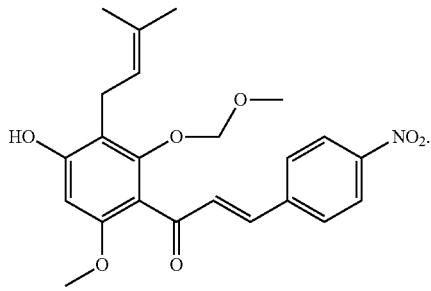

A solution, placed under stirring, of (12) (0.274 g, 0.581 mmols) in MeOH/HCl 1.25 M (8.6 mL) was heated to 45° C. for 1.5 h. The reaction mixture was extracted with AcOEt/H2O [(3×50 mL), 1:1]. The organic phase was dried on sodium sulphate, filtered and evaporated at 20° C., to obtain an orange-yellow solid (0.433 g). The crude product was purified on an Isolute Si II 10 g flash chromatography column, using n-hexane/EtOAc 7:1 as eluent mixture. The organic fraction (test tubes 6-16, 5 mL fractions) was evaporated at RT to obtain (13) (0.251 g), a bright orange solid.

TLC Rf: 0.2 in n-hexane/AcOEt 4:1, MP: 230-235° C. (dec).

1H-NMR (200 MHz, CDCl3): 8.25 (d, 2H, J=8.9 Hz, =CHAr—H), 7.92 (d, 2H, J=16 Hz, CH=), 7.74 (d, 1H, J=16 Hz, CH=), 7.73 (d, 1H, J=8.9 Hz, =CHAr—H), 6.27 (s, 1H, OH), 5.30 (s, 2H, O—CH2-O), 5.16 (t, 1H, J=6.8 Hz, CH2CH=), 3.95 (s, 3H, OCH3), 3.51 (s, 3H, CH2OCH3), 3.34 (d, 2H, J=6.8 Hz, CH2), 1.80 (s, 3H, CH3), 1.69 (s, 3H, CH3).

Example 12: Preparation of (E)-N-(4-{3-[6-methoxy-2,4-bis-methoxymethyloxy-3-(3-methyl-but-2-enyl)phenyl]-3-(oxoprop-1-enyl}phenyl)-acetamide [compound (15)]

(15)

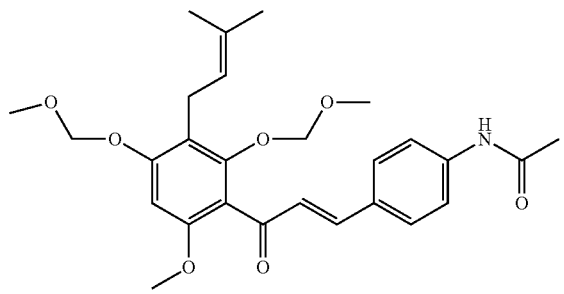

A 10% aqueous solution of NaOH (1.5 mL) was added to a solution, under stirring, of 1-[6-methoxy-2,4-dimethoxymethyloxy-3-(3-methyl-but-2-enyl)-phenyl]-ethanone (5) (0.225 g, 1.330 mmols, 1 equiv) and 4-acetamide benzaldehyde (0.217 g, 1.330 mmols, 1 equiv) in MeOH (26 mL). The reaction mixture was heated to 65° C. for 6 h. It was then extracted with AcOEt (100 mL) and washed with H2O (4×50 mL). The organic phase was dried on sodium sulphate, filtered and evaporated. The crude product (0.386 g), a bright yellow oil, was purified by Isolute Si II 10 g flash chromatography using n-hexane/AcOEt 5:1 as eluent mixture. (15) (0.090 g), which presented as a yellow oil, was obtained from evaporation of the organic fraction (test tubes 115-121, 5 mL fractions).

Yield: 14% TLC Rf: 0.08 in n-hexane/AcOEt 2:1.

1H-NMR (200 MHz, CDCl3): δ 7.79 (s, 1H, NH), 7.28 (d, 2H, J=8.6 Hz, =CHAr—H), 7.18 (d, 2H, J=8.6 Hz, =CHAr—H), 7.08 (d, 1H, J=16 Hz, CH=), 6.64 (d, 1H, J=16 Hz, CH=), 6.30 (s, 1H, Ar—H), 4.95 (s, 2H, O—CH2-O), 4.89 (t, 1H, J=6.8 Hz, CH2CH=), 4.62 (s, 2H, O—CH2-O), 3.46 (s, 3H, OCH3), 3.22 (s, 3H, CH2OCH3), 3.14 (s, 3H, CH2OCH3), 3.06 (d, 2H, J=6.8 Hz, CH2), 1.88 (s, 3H, COCH3), 1.48 (s, 3H, CH3), 1.39 (s, 3H, CH3).

Example 13: Structural formulas of (E)-1-[2,4-dihydroxy-6-methoxy-3-(3-methylbut-2-enyl)phenyl]-3-(4-nitrophenyl)prop-2-en-1-one [compound (14)], (E)-N-(4-{3-[2-hydroxy-6-methoxy-4-methoxymethyloxy-3-(3-methyl-but-2-enyl)phenyl]-3-oxoprop-1-enyl}phenyl)acetamide [compound (16)] and (E)-N-(4-{3-[2,4-dihydroxy-6-methoxy-3-(3-methyl-but-2-enyl)phenyl]-3-oxoprop-1-enyl}-phenyl)acetamide [compound (17)]

(14)

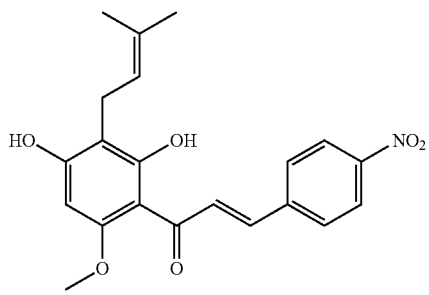

(16)

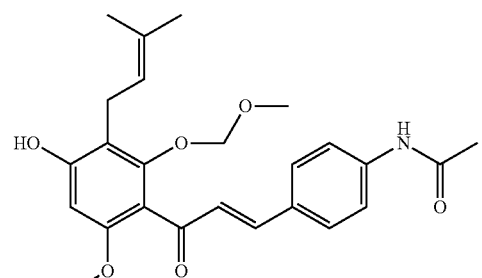

(17)

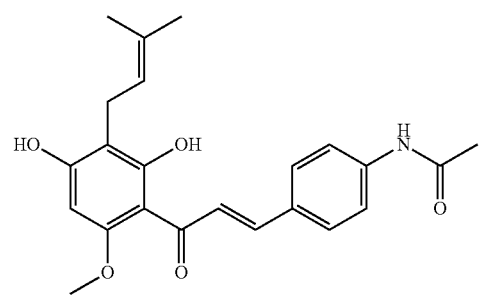

Example 14: Preparation of (E)-3-(3,4-difluorophenyl)-1-[6-methoxy-2,4-bis-methoxymethyloxy-3-(3-methyl-but-2-enyl)phenyl]-prop-2-en-1-one [compound (18)]

(18)

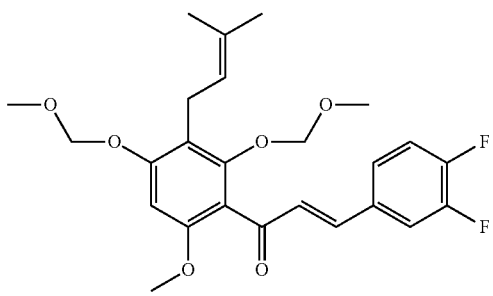

A 10% aqueous solution of NaOH (0.9 mL) was added to a solution, placed under stirring, of 1-[6-methoxy-2,4-dimethoxymethyloxy-3-(3-methyl-but-2-enyl)-phenyl]-ethanone (5) (0.267 g, 0.789 mmols, 1 equiv) and 3,4-difluorobenzaldehyde (0.09 mL, 0.789 mmols, 1 equiv), in MeOH (16 mL). The mixture was then left at 65° C. for 20 h. After that time, the solution was extracted with AcOEt/H2O [(3×50 ml), 2:1]. The organic phase was dried on sodium sulphate, filtered and evaporated. The crude product (0.434 g), a bright yellow oil, was purified after adsorption on silica (silica 230-400 mesh, 0.600 g), by flash chromatography on silica gel column (silica 230-400 mesh, diameter 3 cm, height 15 cm), using n-hexane/AcOEt 7:1 as eluent mixture. (18) (0.276 g, 0.597 mmols) was obtained as a yellow oil from evaporation of the organic fraction (test tubes 43-50, 12 mL fractions, Vm: 200 mL).

Yield: 55% TLC Rf: 0.26 in n-hexane/AcOEt 2:1.

1H-NMR (200 MHz, CDCl3): δ 7.35 (d, 1H, J=15.7 Hz, CH=), 7.26 (d, 1H, J=16 Hz, =CHAr—H), 6.96 (d, 1H, J=16 Hz, =CHAr—H), 6.84 (d, 1H, J=15.7 Hz, CH=), 6.60 (s, 1H, Ar—H), 5.25 (s, 2H, O—CH2-O), 5.21 (t, 1H, J=6.8 Hz, CH2CH=), 4.92 (s, 2H, O—CH2-O), 3.93 (s, 3H, OCH3), 3.78 (s, 3H, CH2OCH3), 3.52 (s, 3H, CH2OCH3), 3.35 (d, 2H, J=6.8 Hz CH2), 1.78 (s, 3H, CH3), 1.70 (s, 3H, CH3).

Example 15: Preparation of (E)-3-(3,4-difluorophenyl)-1-[2-hydroxy-6-methoxy-4-methoxymethyloxy-3-(3-methyl-but-2-enyl)phenyl]prop-2-en-1-one [compound (19)] and (E)-3-(3,4-difluorophenyl)-1-[2,4-dihydroxy-6-methoxy-3-(3-methyl-but-2-enyl)-phenyl]-prop-2-en-1-one [compound (20)]

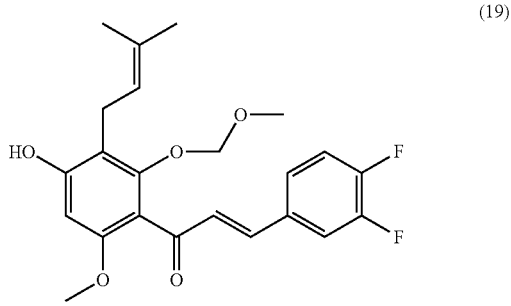

(19)

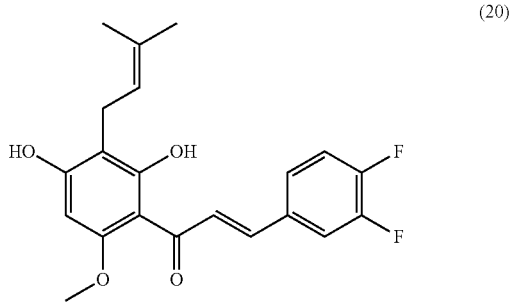

(20)

A solution of (18) (0.275 g, 0.595 mmols) in MeOH/HCl 1.25 M (7.3 ml) was heated to 45° C. and maintained under those conditions, under stirring, for 1.15 h. The reaction mixture was extracted with AcOEt/H2O [(3×60 mL), 2:1]. The organic phase was dried on sodium sulphate, filtered and evaporated at RT. The yellow crude oil (0.196 g) was purified, after adsorption on 0.300 g of silica 230-400 mesh, by flash chromatography on silica gel column (silica 230-400 mesh, diameter 2 cm, height 17 cm), using n-hexane/EtOAc 4:1 as eluent mixture. (19) (0.024 g) was obtained as an orange-yellow oil and (20) (0.111 g) as a yellow solid from evaporation of the organic fractions (test tubes 11-16, test tubes 23-36, 8 mL fractions). TLC Rf 19: 0.24 in n-hexane/AcOEt 2:1

1H-NMR (200 MHz, CDCl3): δ 7.85 (d, 1H, J=16 Hz, CH=), 7.76 (d, 1H, J=16 Hz, CH=), 7.28-7.44 (m, 2H, =CHAr—H), 6.98 (m, 1H, =CHAr—H), 6.29 (s, 1H, Ar—H), 5.32 (s, 2H, O—CH2-O), 5.24 (t, 1H, J=6.9 Hz, CH2CH=), 3.98 (s, 3H, OCH3), 3.54 (s, 3H, CH2OCH3), 3.35 (d, 2H, J=7.2 Hz, CH2), 1.84 (s, 3H, CH3), 1.72 (s, 3H, CH3).

TLC Rf 20: 0.23 in n-hexane/AcOEt 2:1, MP: 237-240° C.

1H-NMR (200 MHz, CDCl3): δ 7.84 (d, 1H, J=15.4 Hz, CH=), 7.73 (d, 1H, J=15.4 Hz, CH=), 7.28-7.44 (m, 2H, =CHAr—H), 6.98 (m, 1H, =CHAr—H), 6.24 (s, 1H, Ar—H), 5.96 (d, 1H, OH), 5.27 (t, 1H, J=7.1 Hz, CH2CH=), 3.95 (s, 3H, OCH3), 3.40 (d, 2H, J=7.4 Hz, CH2), 1.84 (s, 3H, CH3), 1.79 (s, 3H, CH3).

Example 16: Preparation of (E)-3-(2,4-difluoro-phenyl)-1-[6-methoxy-2,4-dimethoxymethyloxy-3-(3-methyl-but-2-enyl)phenyl]-prop-2-en-1-one [compound (21)]

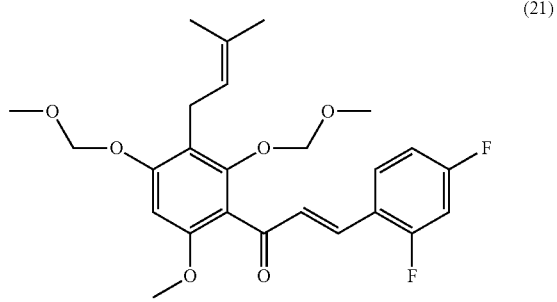 [SMILES: COCOc1cc(OC)c(C(=O)/C=C/c2ccc(F)cc2F)c(OCOC)c1CC=C(C)C]

(21)

A 10% aqueous solution of NaOH (0.9 mL) was added to a solution, placed under stirring, of 1-[6-methoxy-2,4-dimethoxymethyloxy-3-(3-methyl-but-2-enyl)-phenyl]-ethanone (5) (0.271 g, 0.802 mmols, 1 equiv) and 2,4-difluoro-benzaldehyde (0.09 mL, 0.802 mmols, 1 equiv), in MeOH (16.3 mL). The mixture was then left at 65° C. for 20 h. After that time, the solution was extracted with AcOEt/H2O [(3×50 mL), 2:1]. The organic phase was dried on sodium sulphate, filtered and evaporated. The crude product (0.453 g), a bright yellow oil, was purified after adsorption on silica (silica 230-400 mesh, 0.600 g), by flash chromatography on silica gel column (silica 230-400 mesh, diameter 3 cm, height 15 cm), using n-hexane/AcOEt 8:1 as eluent mixture. (21) (0.118 g, 0.255 mmols) was obtained as a yellow oil from evaporation of the organic fraction (test tubes 56-67, 12 mL fractions, Vm: 250 mL).

Yield: 32% TLC Rf: 0.16 in n-hexane/AcOEt 4:1

1H-NMR (200 MHz, CDCl3): δ 7.73 (d, 1H, J=16 Hz, =CHAr—H), 7.56 (d, 1H, J=16 Hz, CH=) 7.50 (t, 1H, J=16 Hz, =CHAr—H), 7.08 (d, 1H, J=16 Hz, CH=), 7.02 (d, 1H, J=16 Hz, CH=), 6.75-6.62 (m, 3H, =CHAr—H), 6.59 (s, 1H, Ar—H), 5.24 (s, 2H, O—CH2-O), 5.19 (t, 1H, J=6.9 Hz, CH=), 4.92 (s, 2H, O—CH2-O), 3.83 (s, 3H, OCH3), 3.77 (s, 3H, CH2OCH3), 3.51 (s, 3H, CH2OCH3), 3.34 (d, 2H, J=7.1 Hz, CH2), 1.77 (s, 3H, CH3), 1.68 (s, 3H, CH3).

Example 17: Preparation of (E)-3-(2,4-difluorophenyl)-1-[2-hydroxy-6-methoxy-4-methoxymethyloxy-3-(3-methyl-but-2-enyl)-phenyl]-prop-2-en-1-one [compound (22)], (E)-3-(2,4-difluorophenyl)-1-[4-hydroxy-6-methoxy-2-methoxymethyloxy-3-(3-methyl-but-2-enyl)-phenyl]-prop-2-en-1-one [compound (23)] and (E)-3-(2,4-difluorophenyl)-1-[2,4-dihydroxy-6-methoxy-3-(3-methyl-but-2-enyl)-phenyl]-prop-2-en-1-one [compound (24)]

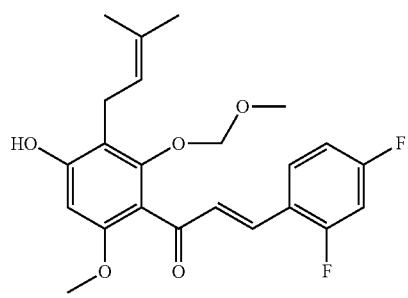
(22)

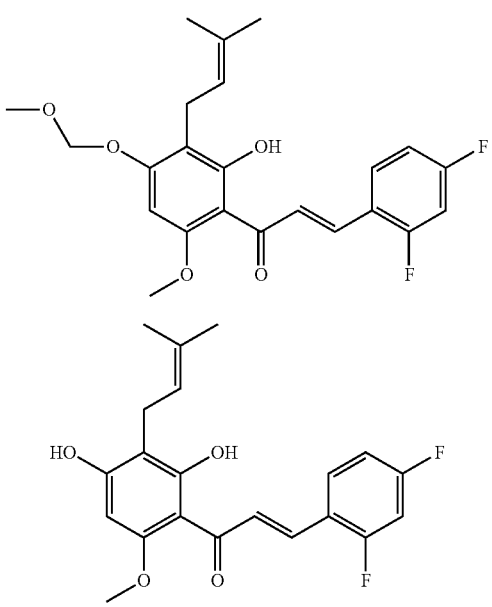
(23)

(24)

A solution of (21) (0.100 g, 0.216 mmols) in MeOH/HCl 1.25 M (2.6 mL) was heated to 45° C. and maintained under these conditions, under stirring, for 1 h. The reaction mixture was extracted with AcOEt/H2O [(3×60 mL), 2:1]. The organic phase was dried on sodium sulphate, filtered and evaporated at RT. The yellow-orange crude oil (0.121 g) was purified, after adsorption on 0.200 g of silica 230-400 mesh, by flash chromatography on silica gel column (silica 230-400 mesh, diameter 2 cm, height 15 cm) using n-hexane/EtOAc 7:1 as eluent mixture. (22) (0.004 g) was obtained as a yellow oil, (23) (0.041 g) as an orange-yellow oil and (24) (0.015 g) as a yellow solid from evaporation of the organic fractions (test tubes 70-72, test tubes 73-81, test tubes 102-103, 12 mL fractions). TLC Rf 22: 0.7 in n-hexane/AcOEt 2:1

1H-NMR (200 MHz, CDCl3): δ 8.02 (d, 1H, J=16 Hz, CH═), 7.83 (d, 1H, J=16 Hz, CH═), 7.54 (t, 1H, ═CHAr—H), 6.75-6.63 (m, 2H, ═CHAr—H), 6.25 (s, 1H, Ar—H), 5.28 (s, 2H, O—CH2-O), 5.20 (t, 1H, J=6 Hz, CH2CH═), 3.92 (s, 3H, CH2OCH3), 3.91 (s, 3H, OCH3), 3.32 (d, 2H, J=6 Hz, CH2), 1.80 (s, 3H, CH3), 1.68 (s, 3H, CH3).

TLC Rf 23: 0.57 in n-hexane/AcOEt 2:1

1H-NMR (200 MHz, CDCl3): δ 7.95 (d, 1H, J=16 Hz, CH═), 7.77 (d, 1H, J=16 Hz, CH═), 7.52 (t, 1H, ═CHAr—H), 6.77-6.62 (m, 2H, ═CHAr—H), 6.24 (s, 1H, Ar—H), 5.28 (s, 2H, O—CH2-O), 5.20 (t, 1H, J=7 Hz, CH2CH═), 3.92 (s, 3H, OCH3), 3.85 (s, 3H, CH2OCH3), 3.32 (d, 2H, J=7 Hz, CH2), 1.80 (s, 3H, CH3), 1.68 (s, 3H, CH3).

TLC Rf 24: 0.37 in n-hexane/AcOEt 2:1, MP: 245-248° C.

1H-NMR (200 MHz, CDCl3): δ 7.98 (d, 1H, J=16 Hz, CH═), 7.87 (d, 1H, J=16 Hz, CH═), 7.49 (t, 1H, ═CHAr—H), 6.77-6.63 (m, 2H, ═CHAr—H), 6.22 (s, 1H, Ar—H), 5.95 (d, 1H, OH), 5.28 (t, 1H, J=7.2 Hz, CH2CH═), 3.90 (s, 3H, OCH3), 3.40 (d, 2H, J=7.2 Hz, CH2), 1.85 (s, 3H, CH3), 1.79 (s, 3H, CH3).

Example 18: Preparation of 1-[6-methoxy-2,4-bis-methoxymethoxy-3-(3-methyl-but-2-enyl)-phenyl]-3-pyridin-2-yl-propenone [compound (25)]

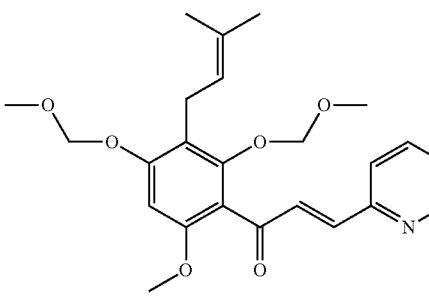
(25)

A 10% aqueous solution of NaOH (0.9 mL) was added to a solution, placed under stirring, of 1-[6-methoxy-2,4-dimethoxymethyloxy-3-(3-methyl-but-2-enyl)-phenyl]-ethanone (5) (0.271 g, 0.802 mmols, 1 equiv) and pyridin-2-carbaldehyde (0.802 mmols, 1 equiv) in MeOH (16.3 mL). The mixture was then left at 65° C. for 20 h. After that time, the solution was extracted with AcOEt/H2O [(3×50 mL), 2:1]. The organic phase was dried on sodium sulphate, filtered and evaporated. The crude product (0.280 g), a yellow oil, was purified after adsorption on silica (silica 230-400 mesh, 0.600 g), by flash chromatography on silica gel column (silica 230-400 mesh, diameter 3 cm, height 15 cm), using n-hexane/AcOEt 2:1 as eluent mixture. Yield: 12%.

1H-NMR (200 MHz, CDCl3): δ 8.11 (d, 1H, J=15.6 Hz, ═CHPy-H), 8.17 (d, 1H, J=15.6 Hz, CH═), 8.63-7.27 (m, 4H, Py-H), 6.02 (s, 2H, O—CH2-O), 5.91 (s, H, ArH), 5.19 (t, 1H, J=6.9 Hz, CH═), 5.19 (t, 1H, J=6.9 Hz, CH═), 4.92 (s, 2H, O—CH2-O), 3.83 (s, 3H, OCH3), 3.77 (s, 3H, CH2OCH3), 3.51 (s, 3H, CH2OCH3), 3.34 (d, 2H, J=7.1 Hz, CH2), 1.77 (s, 3H, CH3), 1.68 (s, 3H, CH3).

Example 19: Preparation of 1-[2-hydroxy-6-methoxy-4-methoxymethoxy-3-(3-methyl-but-2-enyl)-phenyl]-3-pyridin-2-yl-propenone [compound (26×HCl)], 1-[4-hydroxy-6-methoxy-2-methoxymethoxy-3-(3-methyl-but-2-enyl)-phenyl]-3-pyridin-2-yl-propenone [compound (27×HCl)] and 1-[2,4-dihydroxy-6-methoxy-3-(3-methyl-but-2-enyl)-phenyl]-3-pyridin-2-yl-propenone [compound (28×HCl)]

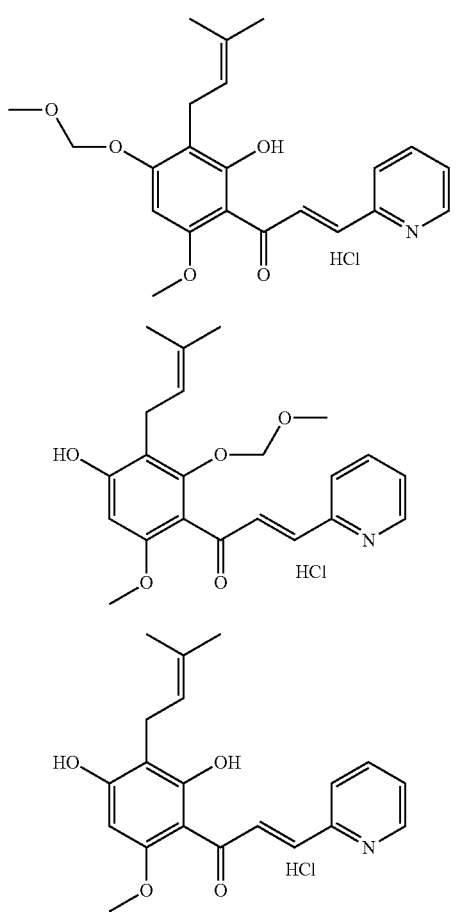

A solution of (25) (0.216 mmols) in MeOH/HCl 1.25 M (2.6 mL) was heated to 45° C. and maintained under these conditions, under stirring, for 1 h. The reaction mixture was evaporated at LP and at RT, obtaining a golden yellow crude oil (0.98 g) which was purified, after adsorption on 0.200 g of silica 230-400 mesh, by flash chromatography on silica gel column (silica 230-400 mesh, diameter 2 cm, height 15 cm) using chloroform/methanol 8:1 as eluent mixture. The hydrochlorides were obtained in succession by evaporation of the most significant fractions: first (26×HCl) (0.013 g) as a yellow oil, then (27×HCl) (0.022 g) as an orange-yellow oil, and finally (28×HCl) (0.011 g) as a brownish-yellow solid.

1H-NMR (200 MHz, DMSO-d6): δ 7.90 (d, 1H, J=16 Hz, CH═), 7.56 (d, 1H, J=16 Hz, CH═), 8.39-9.27 (m, 4H, Py-H), 5.91 (s, H, Ar—H), 5.28 (s, 2H, O—CH2-O), 5.20 (t, 1H, J=6 Hz, CH2CH═), 5.0, (brs, H), 3.92 (s, 3H, CH2OCH3), 3.91 (s, 3H, OCH3), 3.32 (d, 2H, J=6 Hz, CH2), 1.80 (s, 3H, CH3), 1.68 (s, 3H, CH3).

1H-NMR (200 MHz, DMSO-d6): δ 7.95 (d, 1H, J=16 Hz, CH═), 7.77 (d, 1H, J=16 Hz, CH═), 8.35-9.22 (m, 4H, Py-H), 6.02 (s, 2H, O—CH2-O), 5.87 (s, H, Ar—H), 5.21 (t, 1H, J=7 Hz, CH2CH═), 3.94 (s, 3H, OCH3), 3.79 (s, 3H, CH2OCH3), 3.29 (d, 2H, J=7 Hz, CH2), 1.81 (s, 3H, CH3), 1.70 (s, 3H, CH3).

1H-NMR (200 MHz, DMSO-d6): δ 7.90 (d, 1H, J=16 Hz, CH═), 7.56 (d, 1H, J=16 Hz, CH═), 8.39-9.27 (m, 4H, Py-H), 5.87 (s, H, Ar—H), 5.21 (t, 1H, J=7 Hz, CH2CH═), 3.73 (s, 3H, OCH3), 3.29 (d, 2H, J=7 Hz, CH2), 1.81 (s, 3H, CH3), 1.70 (s, 3H, CH3).

Example 20: Preparation of 3-(5-chloro-pyridin-3-yl)-1-[6-methoxy-2,4-bis-methoxymethoxy-3-(3-methyl-but-2-enyl)-phenyl]-propenone [compound (29)]

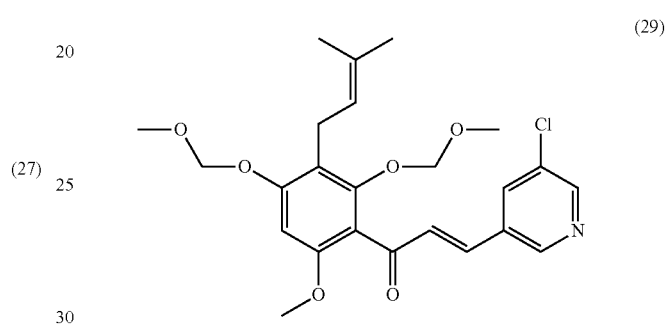

Similarly to compound (25), (29) was obtained as a golden yellow oil by condensing with 5-chloro-pyridin-2-carbaldehyde.

1H-NMR (200 MHz, CDCl3): δ 7.90 (d, 1H, J=15.6 Hz, ═CHPy-H), 7.56 (d, 1H, J=15.6 Hz, CH═), 8.72-8.03 (3m, 3H, Py-H), 6.02 (s, 2H, O—CH2-O), 5.91 (s, H, ArH), 5.19 (t, 1H, J=6.9 Hz, CH═), 5.19 (t, 1H, J=6.9 Hz, CH═), 4.92 (s, 2H, O—CH2-O), 3.79 (s, 3H, OCH3), 3.77 (s, 3H, CH2OCH3), 3.51 (s, 3H, CH2OCH3), 3.34 (d, 2H, J=7.1 Hz, CH2), 1.77 (s, 3H, CH3), 1.68 (s, 3H, CH3).

Example 21: Preparation of 3-(5-chloro-pyridin-3-yl)-1-[2-hydroxy-6-methoxy-4-methoxymethoxy-3-(3-methyl-but-2-enyl)-phenyl]-propenone [compound (30×HCl)], 3-(5-chloro-pyridin-3-yl)-1-[4-hydroxy-6-methoxy-2-methoxymethoxy-3-(3-methyl-but-2-enyl)-phenyl]-propenone [compound (31×HCl)] and 3-(5-chloro-pyridin-3-yl)-1-[2,4-dihydroxy-6-methoxy-3-(3-methyl-but-2-enyl)-phenyl]-propenone [compound (32×HCl)]

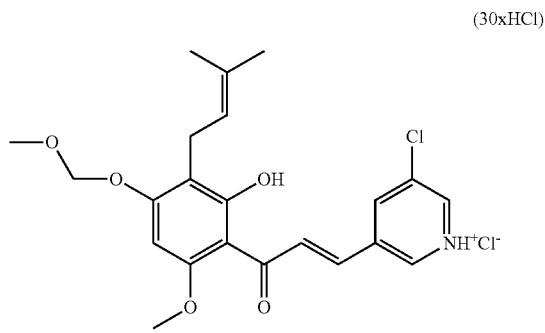

-continued

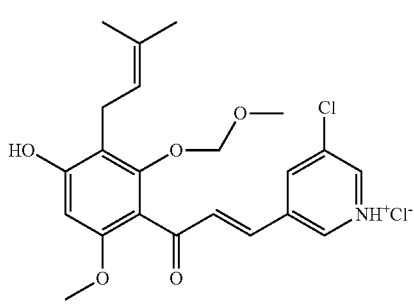
(31xHCl)

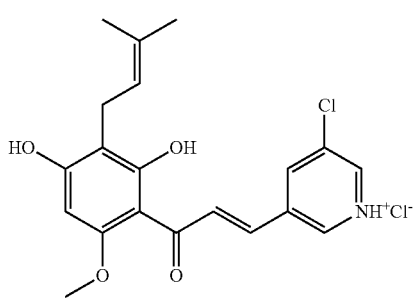
(32xHCl)

Similarly to (26)-(28), (30xHCl)-(32xHCl) were obtained from (29).

1H-NMR (200 MHz, DMSO-d6): δ 7.90 (d, 1H, J=16 Hz, CH═), 7.56 (d, 1H, J=16 Hz, CH═), 9.36-9.31 (m, 3H, Py-H), 5.91 (s, H, Ar—H), 5.30 (s, 2H, O—CH2-O), 5.20 (t, 1H, J=6 Hz, CH2CH═), 5.0, (brs, H), 3.92 (s, 3H, CH2OCH3), 3.91 (s, 3H, OCH3), 3.32 (d, 2H, J=6 Hz, CH2), 1.80 (s, 3H, CH3), 1.68 (s, 3H, CH3).

1H-NMR (200 MHz, DMSO-d6): δ 7.92 (d, 1H, J=16 Hz, CH═), 7.56 (d, 1H, J=16 Hz, CH═), 9.36-9.31 (m, 3H, Py-H), 6.02 (s, 2H, O—CH2-O), 5.88 (s, H, Ar—H), 5.22 (t, 1H, J=7 Hz, CH2CH═), 3.73 (s, 3H, OCH3), 3.79 (s, 3H, CH2OCH3), 3.29 (d, 2H, J=7 Hz, CH2), 1.81 (s, 3H, CH3), 1.70 (s, 3H, CH3).

1H-NMR (200 MHz, DMSO-d6): δ 7.90 (d, 1H, J=16 Hz, CH═), 7.67 (d, 1H, J=16 Hz, CH═), 9.36-9.31 (m, 3H, Py-H), 5.87 (s, H, Ar—H), 5.21 (t, 1H, J=7 Hz, CH2CH═), 3.75 (s, 3H, OCH3), 3.29 (d, 2H, J=7 Hz, CH2), 1.81 (s, 3H, CH3), 1.70 (s, 3H, CH3).

Example 22: Preparation of 1-[6-methoxy-2,4-bis-methoxymethoxy-3-(3-methyl-but-2-enyl)-phenyl]-3-pyridin-4-yl-propenone [compound (33)]

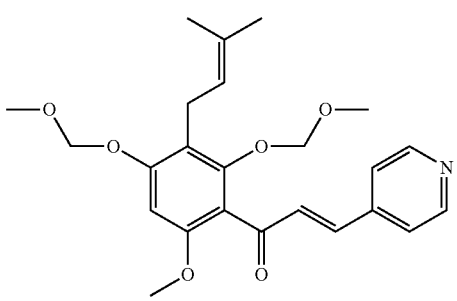
(33)

Similarly to compound (25), (33) was obtained by condensing with pyridin-4-carbaldehyde.

1H-NMR (200 MHz, CDCl3): δ 7.88 (d, 1H, J=15.6 Hz, ═CHPy-H), 7.866 (d, 1H, J=15.6 Hz, CH═), 8.71-7.51 (2m, 4H, Py-H), 6.02 (s, 2H, O—CH2-O), 5.91 (s, H, ArH), 5.19 (t, 1H, J=6.9 Hz, CH═), 5.19 (t, 1H, J=6.9 Hz, CH═), 4.92 (s, 2H, O—CH2-O), 3.73 (s, 3H, OCH3), 3.77 (s, 3H, CH2OCH3), 3.51 (s, 3H, CH2OCH3), 3.34 (d, 2H, J=7.1 Hz, CH2), 1.77 (s, 3H, CH3), 1.68 (s, 3H, CH3).

Example 23: Preparation of 1-[2-hydroxy-6-methoxy-4-methoxymethoxy-3-(3-methyl-but-2-enyl)-phenyl]-3-pyridin-4-yl-propenone [compound (34xHCl)], 1-[4-hydroxy-6-methoxy-2-methoxymethoxy-3-(3-methyl-but-2-enyl)-phenyl]-3-pyridin-4-yl-propenone [compound (35xHCl)] and 1-[2,4-dihydroxy-6-methoxy-3-(3-methyl-but-2-enyl)-phenyl]-3-pyridin-4-yl-propenone [compound (36xHCl)]

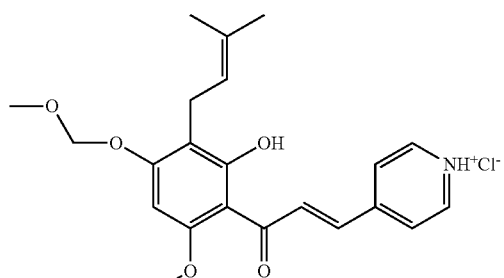
(34xHCl)

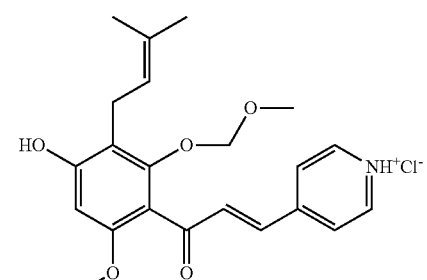
(35xHCl)

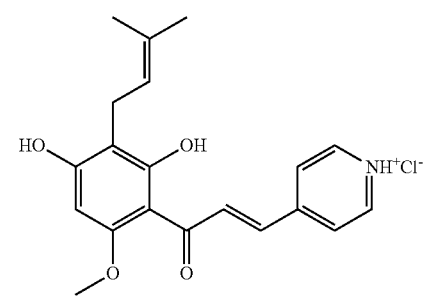
(36xHCl)

Similarly to (26)-(28), (34xHCl)-(36xHCl) were obtained from (33).

1H-NMR (200 MHz, DMSO-d6): δ 7.91 (d, 1H, J=16 Hz, CH═), 7.56 (d, 1H, J=16 Hz, CH═), 9.35-8.63 (m, 4H, Py-H), 5.91 (s, H, Ar—H), 5.30 (s, 2H, O—CH2-O), 5.20 (t, 1H, J=6 Hz, CH2CH═), 5.0, (brs, H), 3.92 (s, 3H, CH2OCH3), 3.91 (s, 3H, OCH3), 3.32 (d, 2H, J=6 Hz, CH2), 1.80 (s, 3H, CH3), 1.68 (s, 3H, CH3).

1H-NMR (200 MHz, DMSO-d6): δ 7.89 (d, 1H, J=16 Hz, CH═), 7.53 (d, 1H, J=16 Hz, CH═), 9.35-8.60 (2m, 4H,

Py-H), 6.02 (s, 2H, O—CH2-O), 5.87 (s, H, Ar—H), 5.22 (t, 1H, J=7 Hz, CH2CH=), 3.73 (s, 3H, OCH3), 3.79 (s, 3H, CH2OCH3), 3.29 (d, 2H, J=7 Hz, CH2), 1.81 (s, 3H, CH3), 1.70 (s, 3H, CH3).

1H-NMR (200 MHz, DMSO-d6): δ 7.90 (d, 1H, J=16 Hz, CH=), 7.56 d, 1H, J=16 Hz, CH=), 9.35-8.60 (2m, 4H, Py-H), 5.85 (s, H, Ar—H), 5.21 (t, 1H, J=7 Hz, CH2CH=), 3.75 (s, 3H, OCH3), 3.29 (d, 2H, J=7 Hz, CH2), 1.81 (s, 3H, CH3), 1.70 (s, 3H, CH3).

Example 24: Preparation of N-(4-{3-[6-methoxy-2,4-bis-methoxymethoxy-3-(3-methyl-but-2-enyl)-phenyl]-3-oxo-propenyl}-phenyl)-methanesulphonamide [compound (37)]

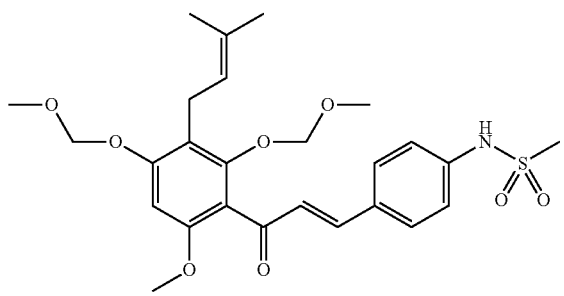

(37)

Similarly to compound (25), (37) was obtained by condensing with N-(4-formyl-phenyl)-methanesulphonamide.

1H-NMR (200 MHz, CDCl3): δ 7.90 (d, 1H, J=16 Hz, =CHAr—H), 7.56 (d, 1H, J=15.6 Hz, CH=), 7.05-6.41 (2m, 4H, Ar—H), 6.02 (s, 2H, O—CH2-O), 5.91 (s, H, ArH), 5.19 (t, 1H, J=6.9 Hz, CH=), 5.19 (t, 1H, J=6.9 Hz, CH=), 4.92 (s, 2H, O—CH2-O), 4.04 (s, NH), 3.73 (s, 3H, OCH3), 3.77 (s, 3H, CH2OCH3), 3.51 (s, 3H, CH2OCH3), 3.34 (d, 2H, J=7.1 Hz, CH2), 2.82 (s, 3H, SO2CH3), 1.77 (s, 3H, CH3), 1.68 (s, 3H, CH3).

Example 25: Preparation of N-(4-{3-[2-hydroxy-6-methoxy-4-methoxymethoxy-3-(3-methyl-but-2-enyl)-phenyl]-3-oxo-propenyl}-phenyl)-methanesulphonamide [compound (38)], N-(4-{(3-[4-hydroxy-6-methoxy-2-methoxymethoxy-3-(3-methyl-but-2-enyl)-phenyl]-3-oxo-propenyl}-phenyl)-methanesulphonamide [compound (39)] and N-(4-{3-[2,4-dihydroxy-6-methoxy-3-(3-methyl-but-2-enyl)-phenyl]-3-oxo-propenyl}-phenyl)-methanesulphonamide [compound (40)]

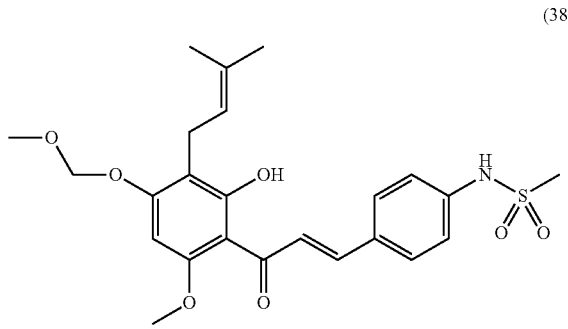

(38)

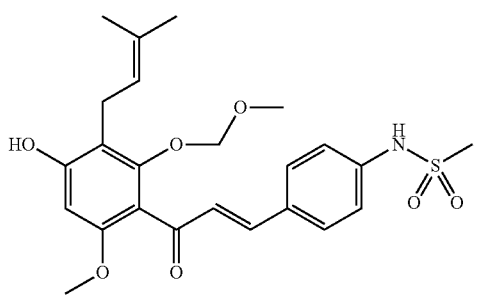

(39)

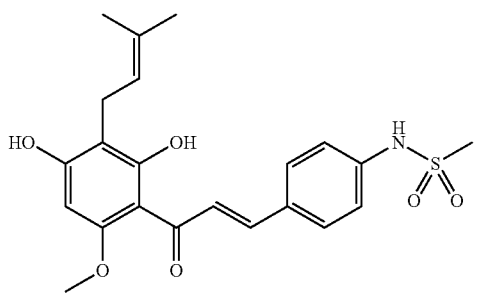

(40)

Similarly to (22)-(24), (38)-(40) were obtained from (37).

1H-NMR (200 MHz, CDCl3): δ 8.00 (d, 1H, J=16 Hz, CH=), 7.83 (d, 1H, J=16 Hz, CH=), 7.05 e 6.41 (2m, 4H Ar—H), 5.91 (s, H, Ar—H), 5.28 (s, 2H, O—CH2-O), 5.20 (t, 1H, J=6 Hz, CH2CH=), 5.01 (brs, H), 4.09 (brs, H, NH), 3.92 (s, 3H, CH2OCH3), 3.91 (s, 3H, OCH3), 3.32 (d, 2H, J=6 Hz, CH2), 2.82 (s, 3H, SO2CH3), 1.80 (s, 3H, CH3), 1.68 (s, 3H, CH3).

1H-NMR (200 MHz, CDCl3): δ 7.90 (d, 1H, J=16 Hz, CH=), 7.83 (d, 1H, J=16 Hz, CH=), 7.12 e 6.41 (2m, 4H Ar—H), 5.87 (s, H, Ar—H), 5.28 (s, 2H, O—CH2-O), 5.20 (t, 1H, J=6 Hz, CH2CH=), 5.1 (brs, H), 4.09 (brs, H, NH), 3.92 (s, 3H, CH2OCH3), 3.91 (s, 3H, OCH3), 3.32 (d, 2H, J=6 Hz, CH2), 2.82 (s, 3H, SO2CH3), 1.80 (s, 3H, CH3), 1.68 (s, 3H, CH3).

1H-NMR (200 MHz, CDCl3): δ 7.90 (d, 1H, J=16 Hz, CH=), 7.56 (d, 1H, J=16 Hz, CH=), 7.06 e 6.42 (2m, 4H Ar—H), 5.87 (s, H, Ar—H), 5.20 (t, 1H, J=6 Hz, CH2CH=), 5.0 (brs, 2H), 4.01 (brs, H, NH), 3.92 (s, 3H, CH2OCH3), 3.91 (s, 3H, OCH3), 3.32 (d, 2H, J=6 Hz, CH2), 2.82 (s, 3H, SO2CH3), 1.80 (s, 3H, CH3), 1.68 (s, 3H, CH3).

Preparation Example 26: 4-chloro-3-chlorosulphonylbenzoic acid [compound (41)]

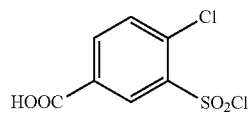

(41)

4-chlorobenzoic acid (2.85 mmols) was cautiously added to a flask containing chlorosulphonic acid (24.9 mmols), followed by NaCl (8.45 mmols) in small portions. When the addition was complete, the reaction mixture was heated to 160° C. for 5 hours. After that time the reaction mixture was poured into an ice bath, and the solid that separated was collected and extracted with AcOEt. The organic phase was dried on Na2SO4 and evaporated in a rotavapor to give (41) as a solid purified residue by crushing from anhydrous hexane. 1H-NMR (200 MHz, CDCl3): δ 8.76 (m, 1H), 8.49 (m, 1H), 7.62 (t, 1H).

Preparation Example 27: 4-chloro-3-sulphamoyl benzoic acid [compound (42)]

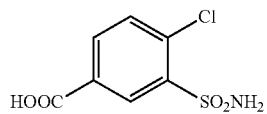

A 2M solution of NH3 in methanol (20 mL) was added to (41) (10 g) and left under stirring at RT for 24 hours. After that time the resulting mixture was concentrated at LP to 50% of its volume, to obtain the formation of a precipitate which was filtered and washed with small portions of MeOH to obtain (42), which was used without further purifications in the subsequent steps.

Preparation Example 28

Sulphonamides (43)-(46) were obtained similarly to (42)

43
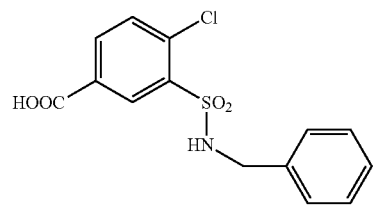

44
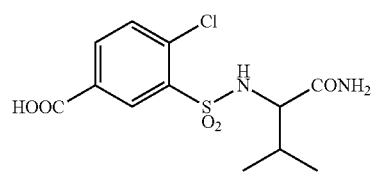

45
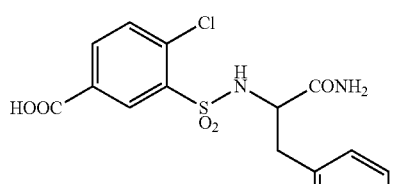

46
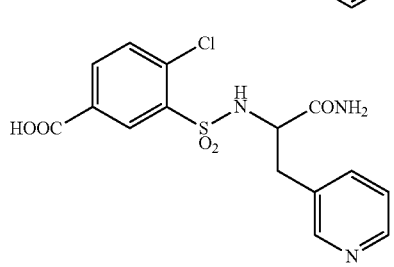

Preparation Example 29: Ethyl 4-chloro-3-sulphamoyl benzoate [compound (47)]

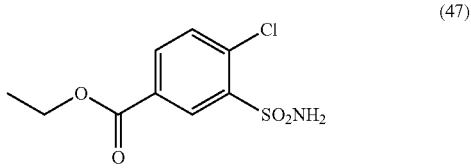 [SMILES: CCOC(=O)c1ccc(Cl)c(S(N)(=O)=O)c1]

Gaseous HCl was bubbled through a solution of (42) (53 mmol) in 125 mL of absolute ethanol for 3 minutes. The resulting suspension was then refluxed for 16 hours. After that time the solvent was evaporated at LP to obtain (47) as a solid which was used "as is" in the subsequent reactions.

Preparation Example 30: Preparation of 2-chloro-5-hydroxymethyl-benzenesulphonamide [compound (48)]

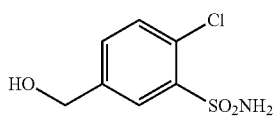

A 2M solution of LiBH4 (49.7 mL) in THF was cautiously added, drop by drop, to a solution of ethyl ester (47) (41.5 mmol) in anhydrous THF (120 mL). The mixture was stirred under reflux for 20 hours, carefully diluted with ice and water (100 mL), cooled to 4° C. for 24 hours and filtered to give (48) (7.2 g) as a white solid.

Preparation Example 31: Preparation of 2-chloro-5-formyl-benzenesulphonamide [compound (49)]

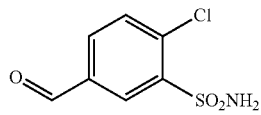

MnO2 (31 g, 5.356 mmol) was added to a vigorously stirred solution of benzyl alcohol (48) (70 mmol) in THF (150 mL). The resulting suspension was reflux heated for 16 hours, filtered through celite and concentrated until dry at low pressure using a rotavapor. The semisolid residue obtained was crushed with hexane to provide the desired aldehyde (49), which was used in the subsequent steps without further purification.

Example 32: Preparation of 2-chloro-5-{3-[2-hydroxy-6-methoxy-4-methoxymethoxy-3-(3-methyl-but-2-enyl)-phenyl]-3-oxo-propenyl}-benzenesulphonamide [compound (50)], 2-chloro-5-{3-[4-hydroxy-6-methoxy-2-methoxymethoxy-3-(3-methyl-but-2-enyl)-phenyl]-3-oxo-propenyl}-benzenesulphonamide [compound (51)], and 2-chloro-5-{3-[2,4-dihydroxy-6-methoxy-3-(3-methyl-but-2-enyl)-phenyl]-3-oxo-propenyl}-benzenesulphonamide [compound (52)]

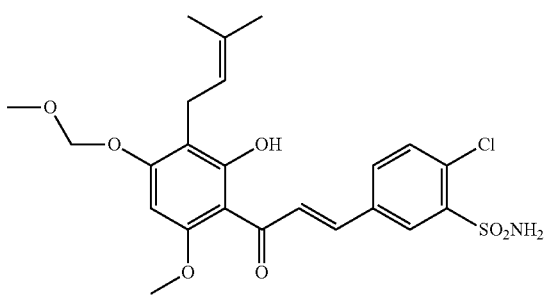
(50)

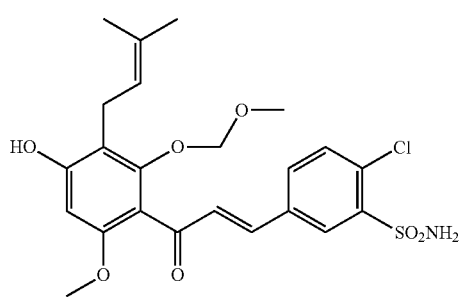
(51)

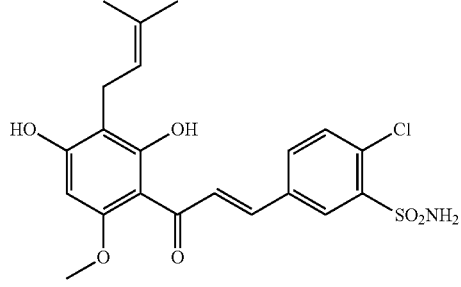
(52)

Similarly to (22)-(24), (50)-(52) are obtained from (53).

1H-NMR (200 MHz, CDCl3): δ 7.91 (d, 1H, J=16 Hz, CH=), 7.89 (d, 1H, J=16 Hz, CH=), 7.90, 7.45 e 7.50 (3m, 3H Ar—H), 5.91 (s, H, Ar—H), 5.28 (s, 2H, O—CH2-O), 5.20 (t, 1H, J=6 Hz, CH2CH=), 5.01 (brs, H), 3.92 (s, 3H, CH2OCH3), 3.91 (s, 3H, OCH3), 3.32 (d, 2H, J=6 Hz, CH2), 2.12 (brs, 2H, SO2NH2), 1.80 (s, 3H, CH3), 1.68 (s, 3H, CH3).

1H-NMR (200 MHz, CDCl3 δ 7.93 (d, 1H, J=16 Hz, CH=), 7.88 (d, 1H, J=16 Hz, CH=), 7.91, 7.50 e 7.48 (3m, 3H Ar—H), 5.87 (s, H, Ar—H), 5.28 (s, 2H, O—CH2-O), 5.20 (t, 1H, J=6 Hz, CH2CH=), 4.90 (brs, H), 3.92 (s, 3H, CH2OCH3), 3.91 (s, 3H, OCH3), 3.32 (d, 2H, J=6 Hz, CH2), 2.01 (brs, 2H, SO2NH2), 1.80 (s, 3H, CH3), 1.68 (s, 3H, CH3).

1H-NMR (200 MHz, CDCl3): δ 7.90 (d, 1H, J=16 Hz, CH=), 7.56 (d, 1H, J=16 Hz, CH=), 7.91, 7.50, e 7.42 (3m, 3H Ar—H), 5.87 (s, H, Ar—H), 5.20 (t, 1H, J=6 Hz, CH2CH=), 5.0 (brs, 2H), 3.92 (s, 3H, CH2OCH3), 3.91 (s, 3H, OCH3), 3.32 (d, 2H, J=6 Hz, CH2), 2.82 (s, 3H, SO2CH3), 2.01 (brs, 2H, SO2NH2), 1.80 (s, 3H, CH3), 1.68 (s, 3H, CH3).

Example 33: Preparation of 2-chloro-5-{3-[6-methoxy-2,4-bis-methoxymethoxy-3-(3-methyl-but-2-enyl)-phenyl]-3-oxo-propenyl}-benzenesulphonamide [compound (53)]

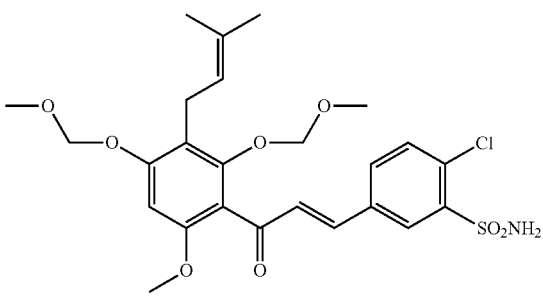
(53)

(53) is obtained by condensing (4a) with (49) under the same conditions as used for (6).

1H-NMR (200 MHz, CDCl3): δ 7.93 (d, 1H, J=16 Hz, CH=), 7.88 (d, 1H, J=16 Hz, CH=), 7.91, 7.50 e 7.48 (3m, 3H Ar—H), 5.87 (s, H, Ar—H), 5.24 (s, 2H, O—CH2-O), 5.14 (t, 1H, J=6.9 Hz, CH2CH=), 4.90 (s, 2H, O—CH2-O), 3.77 (s, 3H, OCH3), 3.50 (s, 3H, CH2OCH3), 3.41 (s, 3H, CH2OCH3), 3.32 (d, 2H, J=6.9 Hz, CH2), 2.01 (brs, 2H, SO2NH2), 1.76 (s, 3H, CH3), 1.68 (s, 3H, CH3).

Example 34: Preparation of 2-chloro-5-{3-[2,4-dihydroxy-6-methoxy-3-(3-methyl-but-2-enyl)-phenyl]-3-oxo-propenyl}-benzenesulphonamide [compound (52)] and 2-chloro-5-[3-(5-hydroxy-7-methoxy-2,2-dimethyl-chroman-6-yl)-3-oxo-propenyl]-benzenesulphonamide [compound (54)]

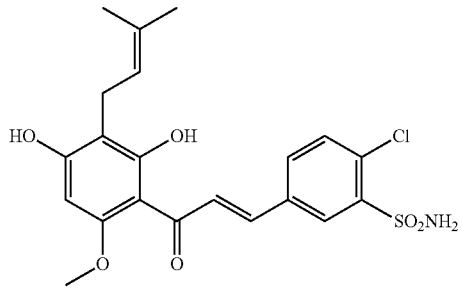
(52)

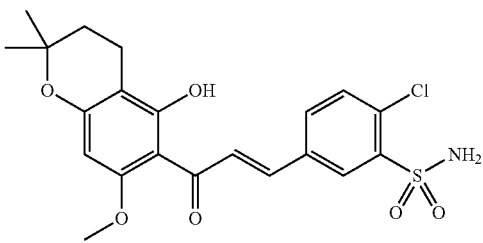
(54)

By operating on (53) under the same conditions as for (8a) and (8b), a mixture of (52) and (54) was obtained which were separated on an Isolute Si II 5 g flash chromatography column, using n-hexane/AcOEt in the ratio of 9:1 as eluent mixture.

(200 MHz, CDCl3): δ 7.90 (d, 1H, J=16 Hz, CH═), 7.56 (d, 1H, J=16 Hz, CH═), 7.91, 7.50, e 7.42 (3m, 3H Ar—H), 5.87 (s, H, Ar—H), 5.20 (t, 1H, J=6 Hz, CH2CH═), 5.0 (brs, 2H), 3.92 (s, 3H, CH2OCH3), 3.91 (s, 3H, OCH3), 3.32 (d, 2H, J=6 Hz, CH2), 2.82 (s, 3H, SO2CH3), 2.01 (brs, 2H, SO2NH2), 1.80 (s, 3H, CH3), 1.68 (s, 3H, CH3).

(200 MHz, CDCl3): δ 7.90 (d, 1H, J=16 Hz, CH═), 7.56 (d, 1H, J=16 Hz, CH═), 7.91, 7.50 e 7.20 (3m, 3H Ar—H), 5.98 (s, H, Ar—H), 5.0 (brs, H), 3.73 (s, 3H, OCH3), 2.84 (brs, 2H, SO2NH2), 2.55 e 1.96 (4H, 2 CH2), 1.66 (s, 3H, CH3), 1.48 (s, 3H, CH3).

Example 35: Preparation of [1-(2-chloro-5-{3-[6-methoxy-2,4-methoxymethoxy-3-(3-methyl-but-2-enyl)-phenyl]-3-oxo-propenyl}-benzenesulphonylaminocarbonyl)-propyl]-benzyl-carbamate [compound (56)]

CBZ aminoacid (55) (2-(N-benzyloxycarbonylamino)butyric acid) (25 mmol), dimethylaminopyridine (50 mmol) and the condensing agent EDCI (25 mmol) were added to a solution of (53) (22 mmol) dissolved in anhydrous DMF (50 mL) cooled to 0° C. and maintained under Ar atmosphere. When the addition was complete, the reaction mixture was heated to room temperature and left under stirring under those conditions for 5 hours. At the end of that time, after TLC monitoring the mixture was evaporated at LP and at a temperature of less than 20° C. using a mechanical pump

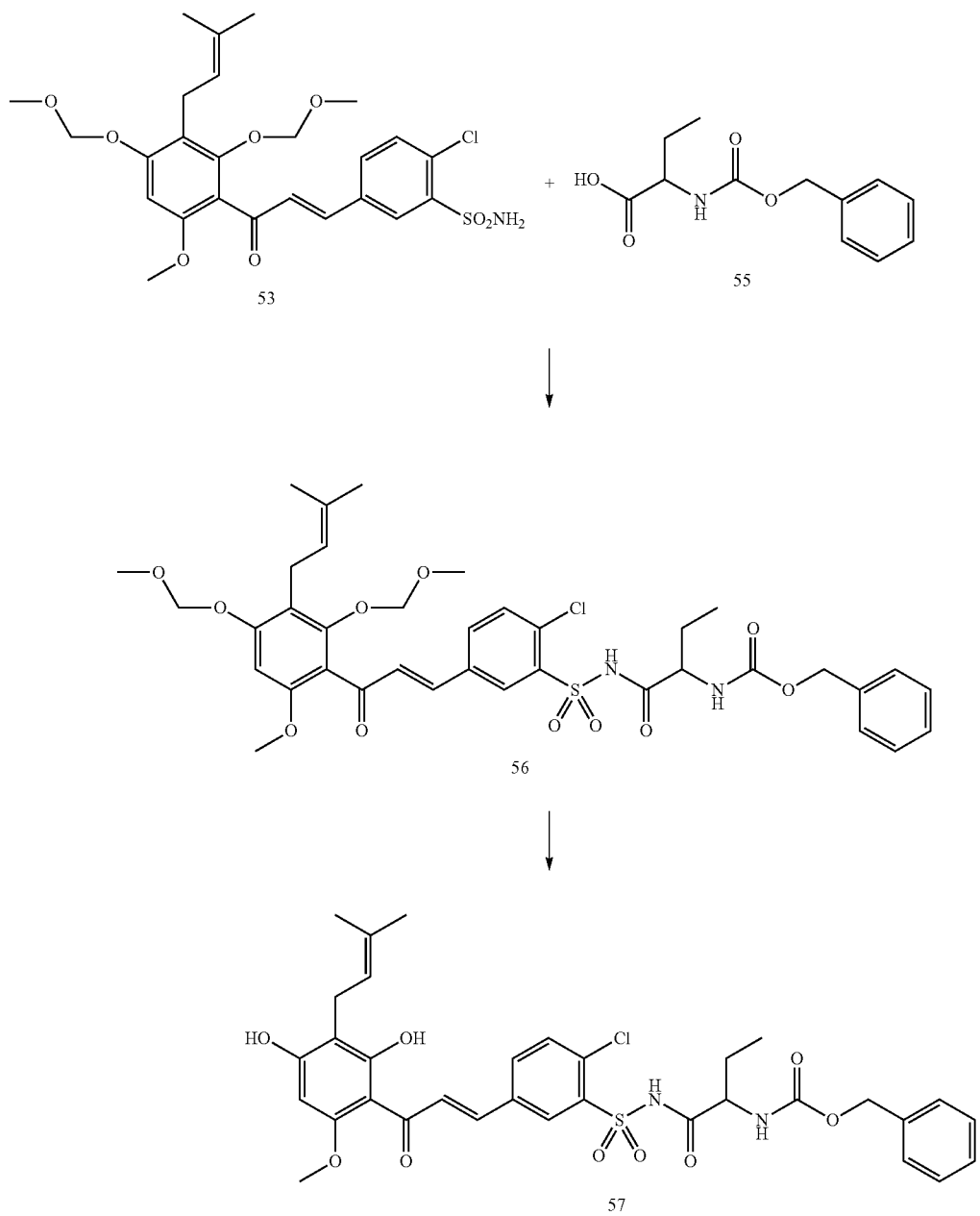 [SMILES: COCOc1cc(OC)c(C(=O)/C=C/c2ccc(Cl)c(S(N)(=O)=O)c2)c(OCOC)c1CC=C(C)C ; CCC(NC(=O)OCc1ccccc1)C(=O)O ; CCC(NC(=O)OCc1ccccc1)C(=O)NS(=O)(=O)c1cc(/C=C/C(=O)c2c(OC)cc(OCOC)c(CC=C(C)C)c2OCOC)ccc1Cl ; CCC(NC(=O)OCc1ccccc1)C(=O)NS(=O)(=O)c1cc(/C=C/C(=O)c2c(OC)cc(O)c(CC=C(C)C)c2O)ccc1Cl]

operating at 0.05 mmHg. The semisolid residue was chromatographed on a silica gel column, eluting with a CHCl3/MeOH 8:1 mixture. A solid residue, mainly consisting of pure (56), was obtained from the most significant intermediate fraction (TLC).

(200 MHz, CDCl3): δ 8.20 (brs, 1H, SO2NHCO), 8.0 (brs, H, NHCO), 7.90 (d, 1H, J=16 Hz, CH═), 7.56 (d, 1H, J=16 Hz, CH═), 7.91, 7.50, e 7.42 (3m, 3H Ar—H), 7.19 (m, 5H, Ar); 5.87 (s, H, Ar—H), 5.30 (s, 2H, CH2Ar), 5.24 (s, 2H, O—CH2-O), 5.14 (t, 1H, J=6.9 Hz, CH2CH═), 4.90 (s, 2H, O—CH2-O), 4.53 (m, H), 3.77 (s, 3H, OCH3), 3.50 (s, 3H, CH2OCH3), 3.41 (s, 3H, CH2OCH3), 3.32 (d, 2H, J=6 Hz, CH2), 1.83 (m, 2H), 1.80 (s, 3H, CH3), 1.68 (s, 3H, CH3), 0.96 (m, 3H).

Example 36: Preparation of [1-(2-chloro-5-{3-[2,4-dihydroxy-6-methoxy-3-(3-methyl-but-2-enyl)-phenyl]-3-oxo-propenyl}-benzenesulphonyl-aminocarbonyl)-propyl]-benzyl-carbamate [compound (57)]

When (56) was treated similarly to the preparation of (22)-(24) of example 17, (57) was obtained as a vitreous residue.

(200 MHz, CDCl3): δ 8.20 (brs, 1H, SO2NHCO), 8.0 (brs, H, NHCO), 7.90 (d, 1H, J=16 Hz, CH═), 7.56 (d, 1H, J=16 Hz, CH═), 7.91, 7.50, e 7.42 (3m, 3H Ar—H), 7.19 (m, 5H, Ar); 5.87 (s, H, Ar—H), 5.30 (s, 2H, CH2Ar), 5.24 5.14 (t, 1H, J=6.9 Hz, CH2CH═), 5.0 (brs, 2H), 4.53 (m, H), 3.77 (s, 3H, OCH3), 3.32 (d, 2H, J=6 Hz, CH2), 1.83 (m, 2H), 1.83 (s, 3H, CH3), 1.68 (s, 3H, CH3), 0.96 (m, 3H).

Compounds 58, 59, 61, 62 and 64-67 were prepared in a one-pot reaction from their precursors, using the same reaction conditions as described for compounds 10 and 11.

Compounds 60 and 63 were prepared using higher temperatures (85° C.) and longer times (48 hours) than for their analogues 18 and 21.

Example 37: Biological Activity of Synthetic Analogues of Xanthohumol

The following table shows the correspondences between the codes of the compounds shown in FIGS. 5-12 and their numbering in accordance with examples 1-36.

TABLE

Correspondences between codes of inhibitors and their numbering

| Code | Numbering |
|---|---|
| XN | Xanthohumol |
| EN233 | 7 |
| EN234 | 8a |
| LR6 | 10 |
| LR7 | 11 |
| LR10 | 13 |
| LR14 | 18 |
| LR15 | 19 |
| LR16 | 20 |
| LR17 | 21 |
| LR18 | 22 |
| LR18b | 23 |
| LR19 | 24 |

MTT Assay

The viability of the HUVEC cells was evaluated with the MTT colorimetric assay (3-(4,5-dimethylthiazol-2-yl)-2,5-diphenyltetrazolium bromide). The cells (1000/well) were plated in complete medium in 96-well plates, and after complete adherence the medium was replaced with a new medium with or without the various inhibitors at different concentrations. The plates were processed at different incubation times (24, 48, 72 and 96 hours), and the absorbance was measured at 570 nm.

Figure 1:
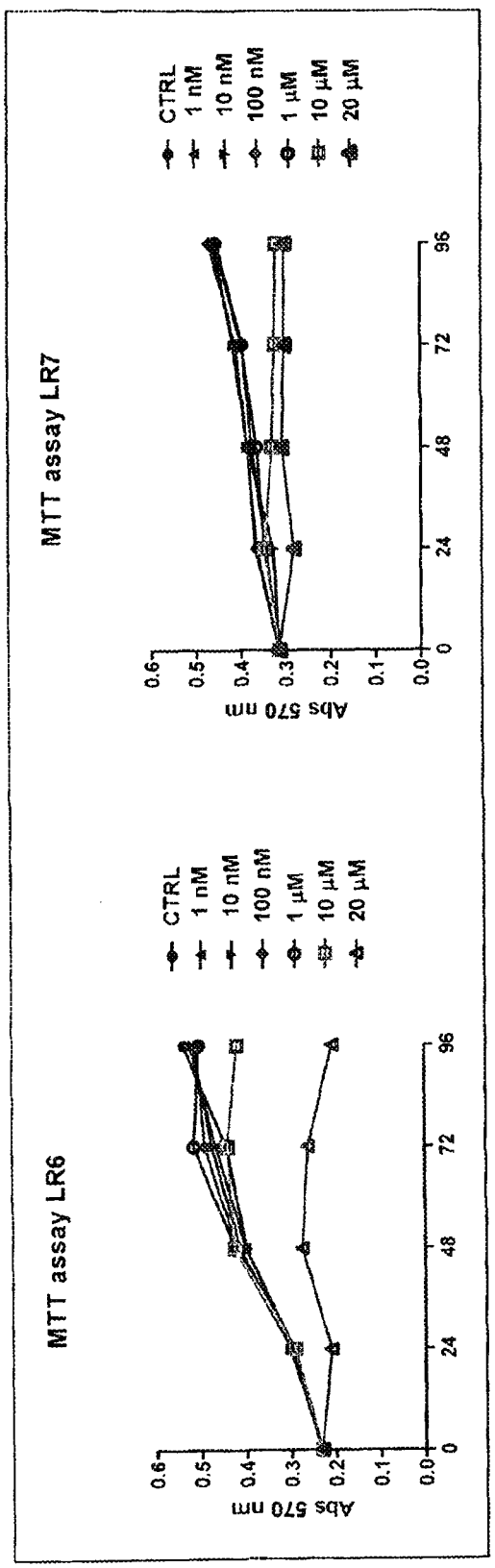
FIG. 1 shows the viability of HUVEC, cells evaluated with the MIT colorimetric assay.

Results:

Significant inhibition of cell growth was observed in the presence of compounds LR6 (10) and LR7 (11) at the concentration of 20 μM after only 24 hours' treatment. Compound LR6, used at the concentration of 10 μM, proved able to reduce cell proliferation after 72 and 96 hours' treatment. At higher concentrations (10 and 20 μM), compound LR7 exhibited cytostatic activity after only 48 hours' incubation. At lower concentrations (1-100 nM and 1 μM), the inhibitors exhibited no significant effect on cell proliferation. The results are shown in FIG. 1.

Migration Assay

The chemotaxis assay was conducted with Boyden chambers [Albini A, Iwamoto Y, Kleinman H K, Martin G R, Aaronson S A, Kozlowski J M, McEwan R N. A rapid in vitro assay for quantitating the invasive potential of tumor cells. Cancer Res. 1987 Jun. 15; 47(12):3239-45; Albini A, Benelli R. The chemoinvasion assay: a method to assess tumor and endothelial cell invasion and its modulation. Nat Protoc. 2007; 2(3):504-11]. The HUVEC cells ($5\times10^4$) were pre-treated for 24 hours with the inhibitors, resuspended in serum-free medium, and plated in the upper compartment of the Boyden chamber. The complete medium was added in the lower compartment of the chamber, and used as chemoattractant. The two chambers were separated by polycarbonate filters (12 μM) coated with collagen (50 μg/mL). After 6 hours' incubation at 37° C., the filters were recovered, the cells present on the upper surface of the filter were mechanically removed, and those on the lower surface were fixed in absolute ethanol and stained with DAPI. The cells were then counted in eight consecutive fields on each filter by fluorescence microscopy.

Figure 2:
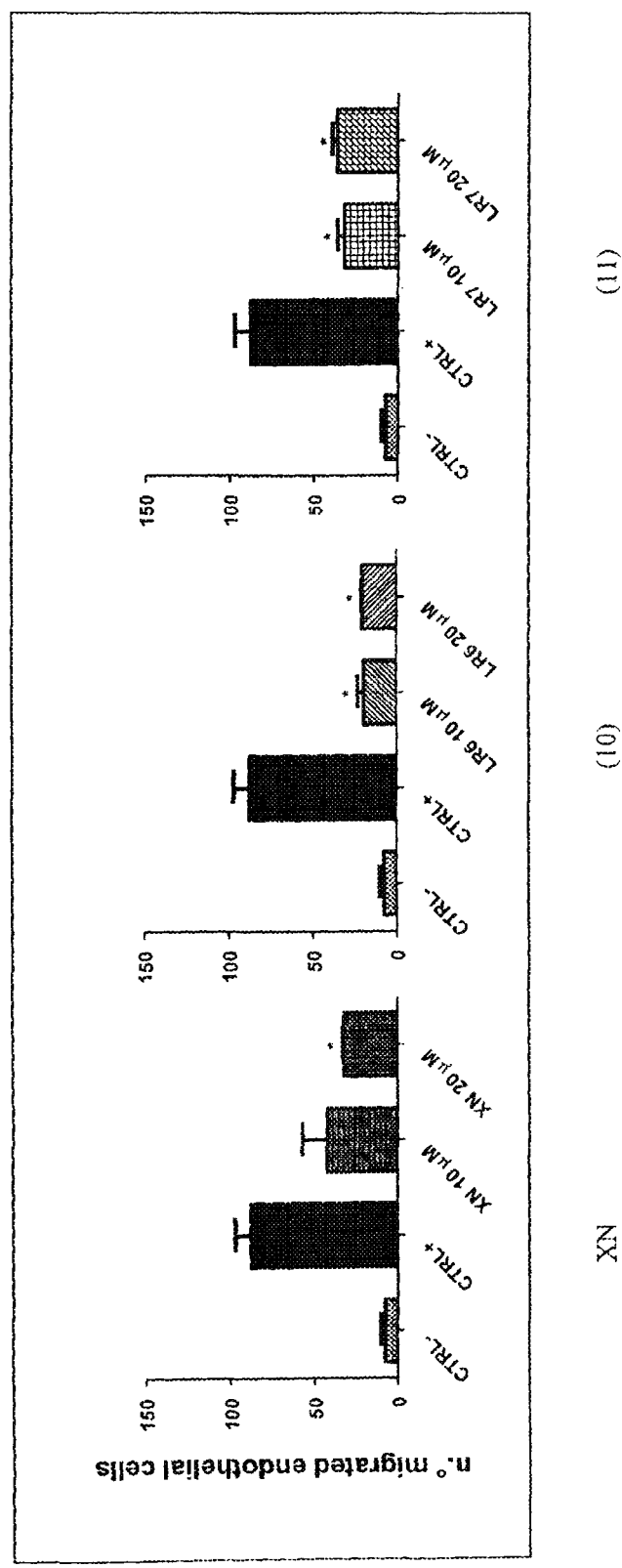
FIG. 2 shows the results of the chemotaxis assay conducted on HUVEC cells using Boyden chambers.

Results:

Significant inhibition of migration (*$P<0.05$) of the HUVEC cells was observed after 24 hours' pre-treatment with inhibitors LR6. (10) and LR7 (11) at the concentrations of 10 μM and 20 μM. The results are shown in FIG. 2. XN was used as control.

Invasion Assay

The chemoinvasion assay was conducted with Boyden chambers [Albini A, Iwamoto Y, Kleinman H K, Martin G R, Aaronson S A, Kozlowski J M, McEwan R N. A rapid in vitro assay for quantitating the invasive potential of tumor cells. Cancer Res. 1987 Jun. 15; 47(12):3239-45; Albini A, Benelli R. The chemoinvasion assay: a method to assess tumor and endothelial cell invasion and its modulation. Nat Protoc. 2007; 2(3):504-11]. The HUVEC cells ($5\times10^4$) were pre-treated for 24 hours with the inhibitors, resuspended in serum-free medium, and plated in the upper compartment of the chamber. The complete medium was added in the lower compartment of the chamber, and used as chemoattractant. The 12 m polycarbonate filters were coated with matrigel (1 mg/mL). After 18 hours' incubation, the cells in the upper compartment of the chamber were mechanically removed, while those adhering to the lower surface of the filter were fixed in absolute ethanol and stained with DAPI. The cells were counted double-blind in eight consecutive fields by fluorescence microscopy.

Figure 3:
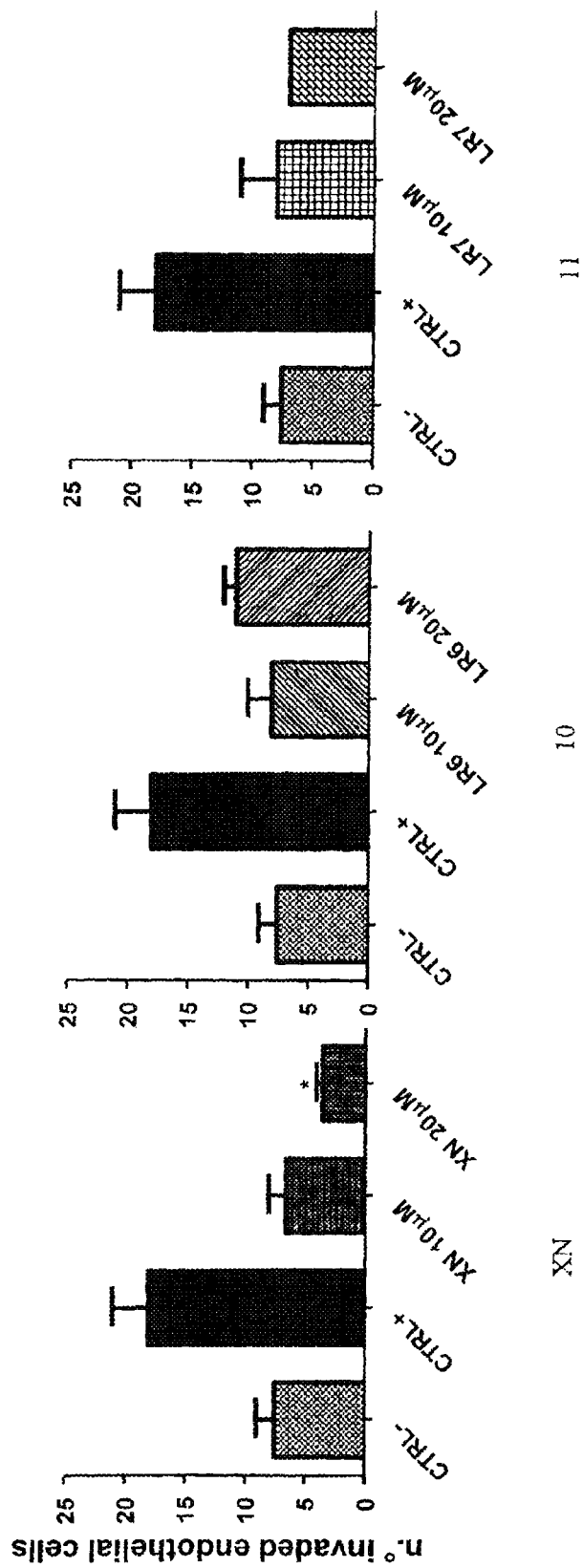
FIG. 3 shows the results of the chemoinvasion assay conducted on HUVEC cells using Boyden chambers.

Results:

24 hours' pre-treatment with inhibitors LR6 (10) and LR7 (11) significantly reduces invasion in the presence of serum (FBS, Foetal Bovine Serum) (*$P<0.05$), even at low concentrations (10 μM). The results are shown in FIG. 3.

Morphogenesis

A 24-well plate was coated with 300 µl/well of liquid matrigel (10 mg/mL) at 4° C., using cold pipettes and avoiding bubbles. The plate was then incubated for one hour at 37° C., until the matrigel polymerised. The HUVEC cells, pre-treated with the different inhibitors, were resuspended in 1 mL of complete medium and then plated in the different wells. The serum-free medium was used as negative control (CTRL-). After 6 hours' incubation, the organisation of the cells in capillary-like structures was examined with an inverted microscope equipped with a camera for the acquisition of images and a digital analysis system.

Figure 4:
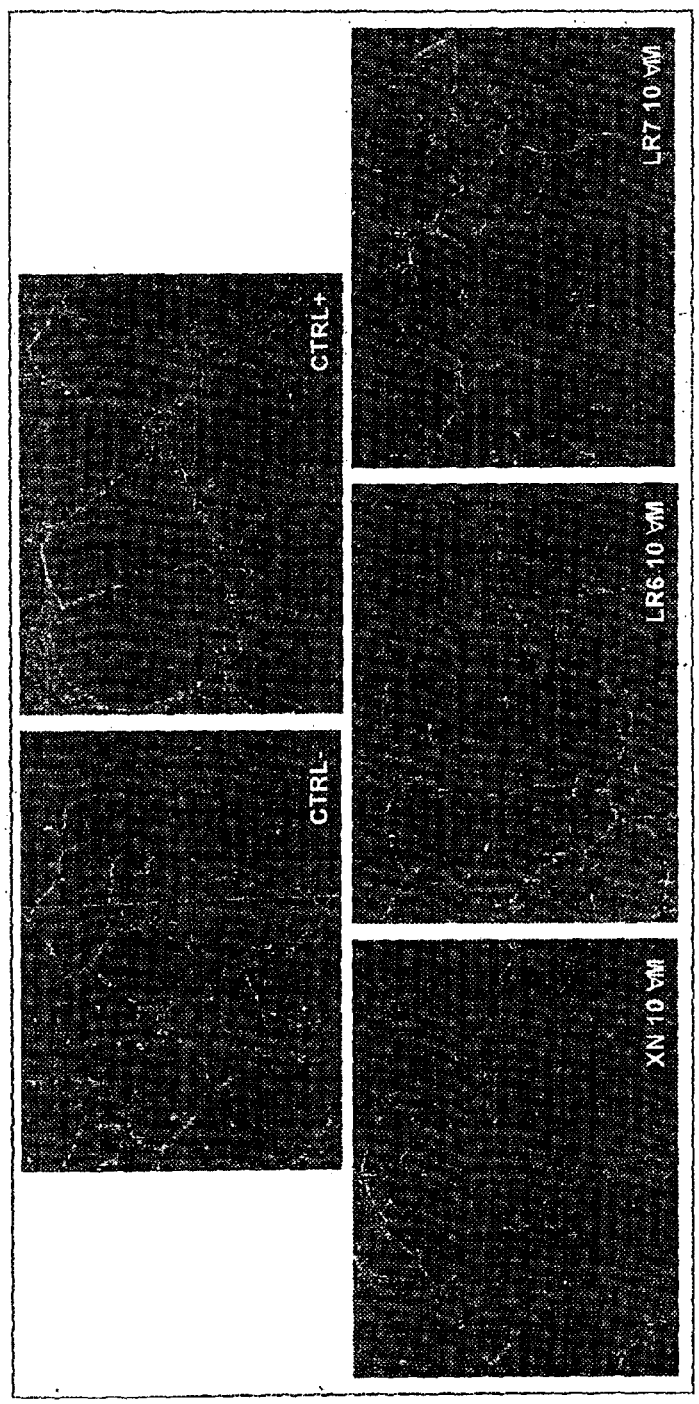
FIG. 4 shows the tendency of HUVEC cells to organise themselves into capillary-like structures.

Results:

The HUVEC cells tend to organise themselves into capillary-like structures when plated on a layer of matrigel, imitating in vitro the events that take place in vivo during angiogenesis. 24 hours' pre-treatment with inhibitors LR6 (10) and LR7 (11) interferes with FBS-dependent morphogenesis. Xanthohumol (XN) was used as control. The results are shown in FIG. 4.

Apoptosis Assay

The HUVEC cells (1×10$^5$) were plated in six-well plates and left to adhere for 18 hours. The next day, the cells were pre-treated with inhibitors LR6 and LR7 (10 µM) in the presence of complete medium. After 24 hours, the cells were detached, washed with PBS and transferred to tubes for cytofluorimetric analysis. The cells were pelletted and resuspended in Annexin V-binding buffer (0.01M HEPES (4-(2-hydroxyethyl)-1-piperazineethanesulphonic acid) (pH 7.4); 0.14 M NaCl; 2.5 mM CaCl$_2$. Fluorescein isothiocyanate Annexin V and 7-amino-actinomycin D were added to the tubes, and the cells were incubated for 15 minutes at room temperature in the dark. The cells were then washed in PBS, the supernatant was removed and the cells resuspended in 400 mL of binding buffer. The samples were analysed on a FACSCanto cytofluorimeter (BD Biosciences), and analysed with FACSDiva Software 6.1.2.

Figure 5:
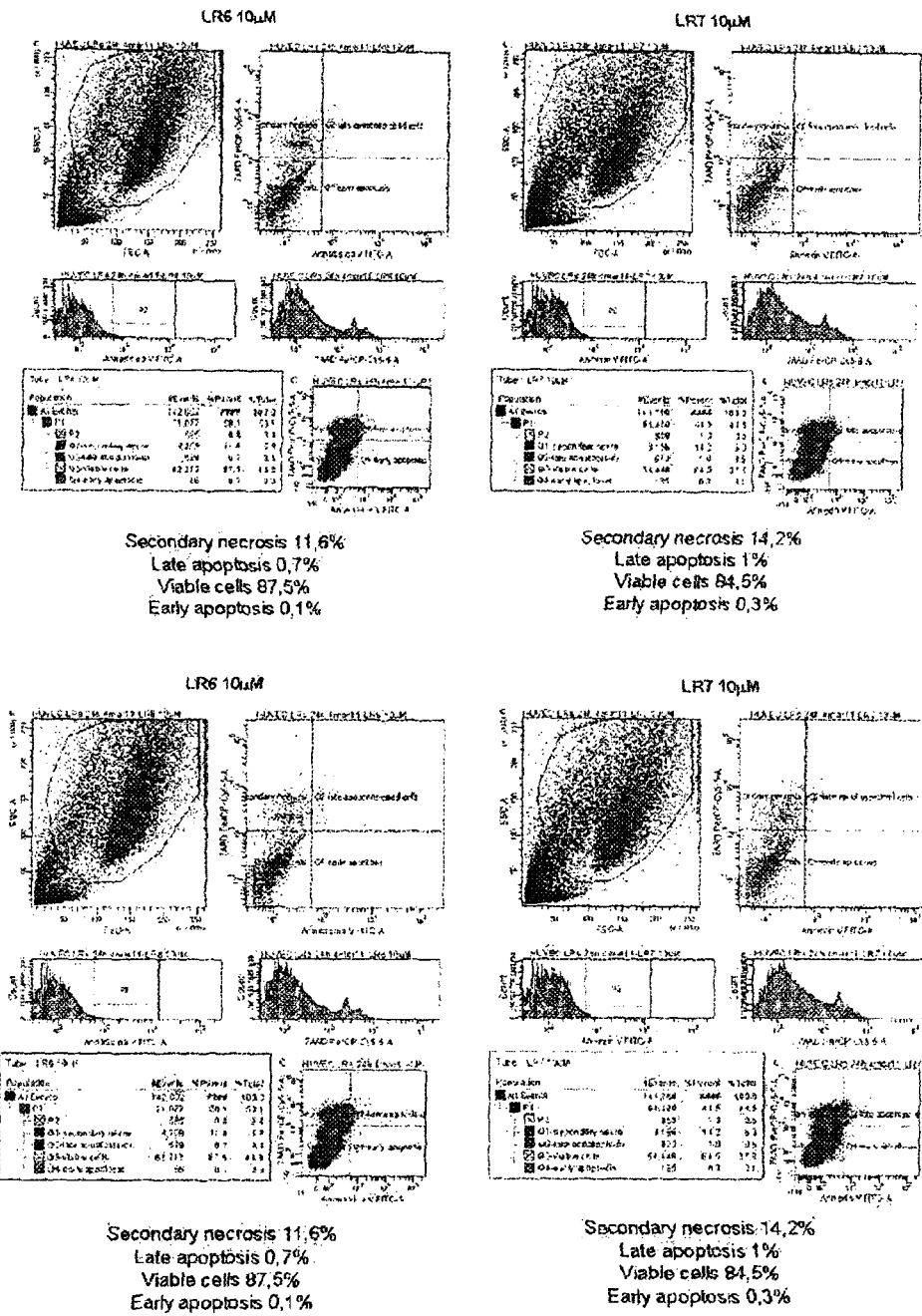
FIG. 5 shows the results of the apoptosis assay conducted on HUVEC cells.

Results:

The endothelial cells treated for 24 hours with inhibitors LR6 (10) and LR7 (11) at the concentration of 10 µM presented a high percentage of viability (about 90%) and absence of apoptosis (FIG. 5). The data obtained suggest that the inhibitors are non-toxic, and do not induce apoptosis in endothelial cells. The results are shown in FIG. 5. XN was used as control.

Figure 6:
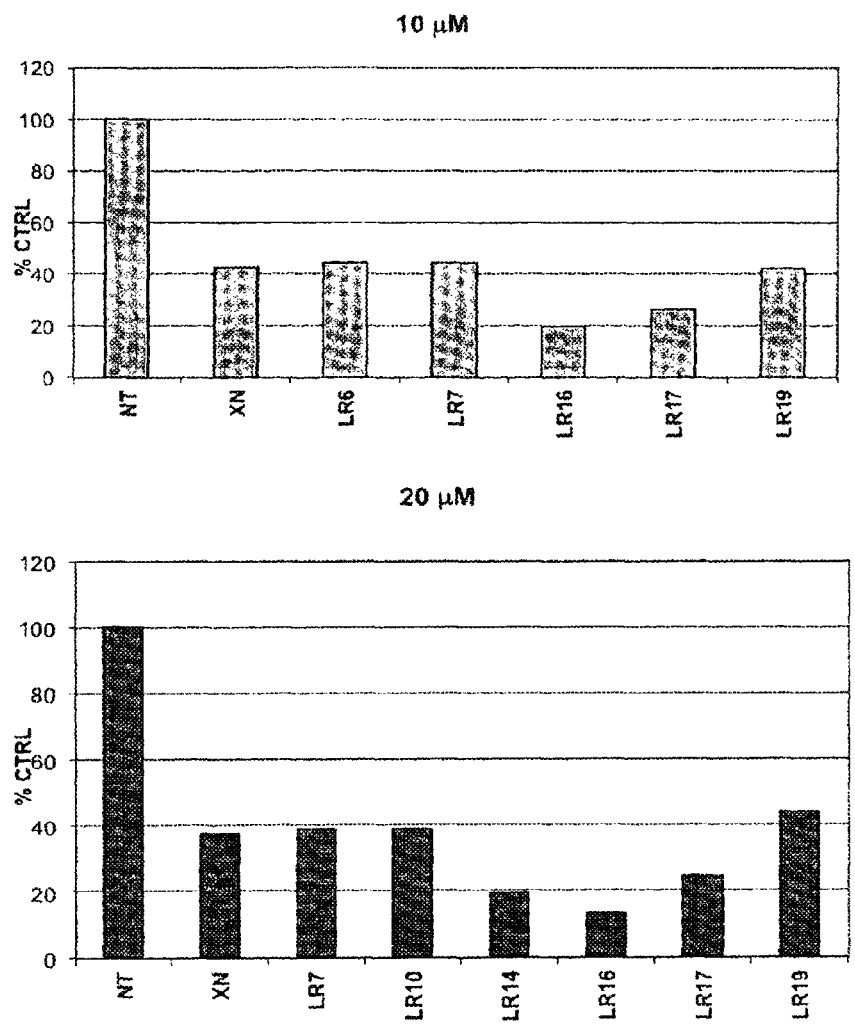
FIG. 6 shows the results of the invasion assay conducted on HUVEC cells.
Figure 7:
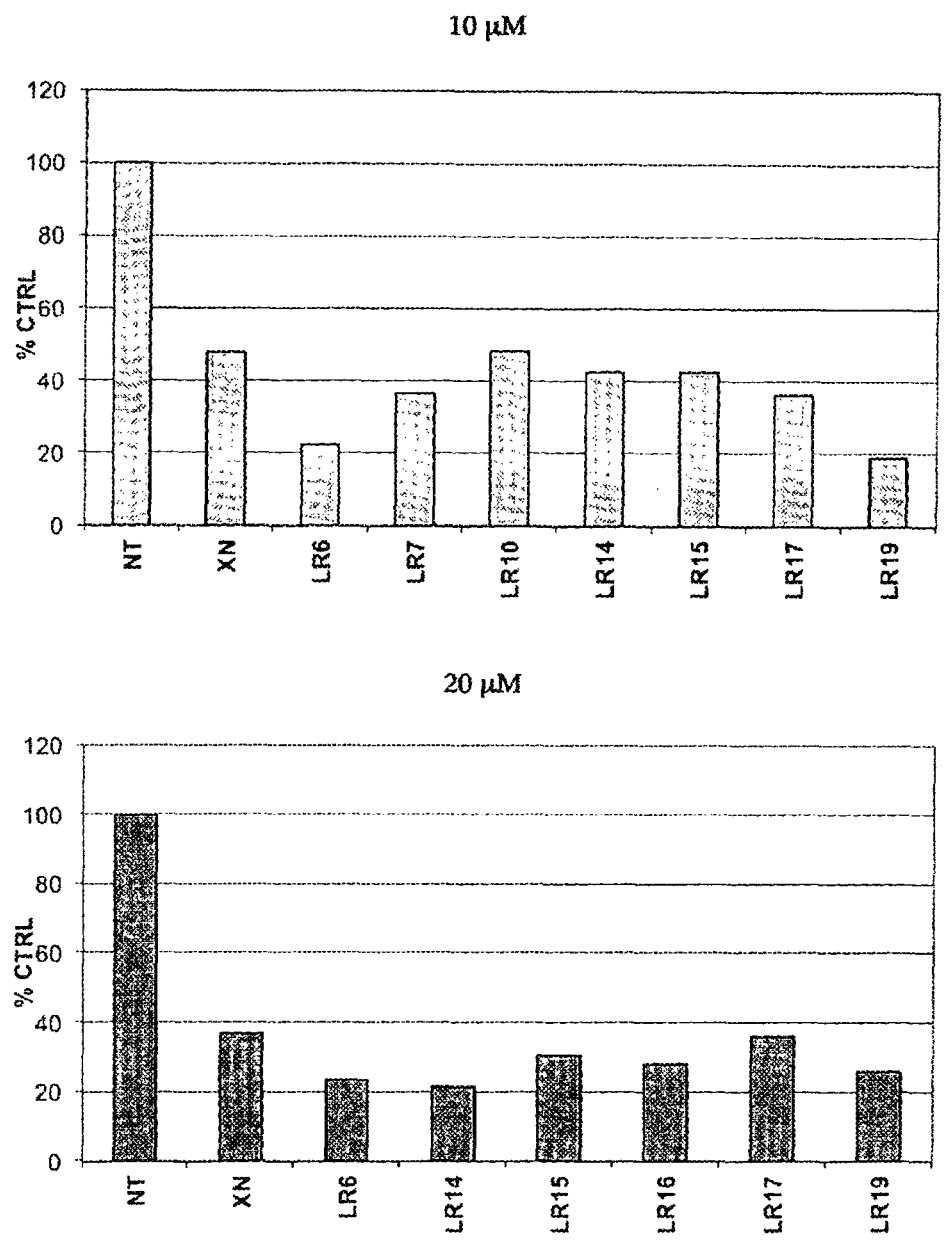
FIG. 7 shows the results of the migration assay conducted on HUVEC cells.

The cumulative comparison tables of the biological activities of XN and its synthetic analogues are reported in FIGS. 6-8.

Invasion Assays—HUVEC Pre-Treated for 24 Hours; Values Standardised on Control

As shown in FIG. 6, the XN control at the concentration of 10 µM reduces endothelial cell invasion by about 60%; some of the novel derivatives, such as LR16 and LR17, at the same concentration, exhibit a greater inhibitory effect (a reduction of about 80% and 75% respectively). The inhibitory effect of the novel compounds is most evident at the concentration of 20 µM.

Migration Assays—HUVEC Pre-Treated for 24 Hours; Values Standardised on Control

As shown in FIG. 7, the XN control at the concentration of 10 µM reduces endothelial cell migration by about 50%; some of the novel derivatives, such as LR19 and LR6, at the same concentration, exhibit a greater inhibitory effect (a reduction of about 80% and 75% respectively). The inhibitory effect of the novel compounds is most evident at the concentration of 20 µM.

The invention claimed is:
1. Compounds of general formula (i):

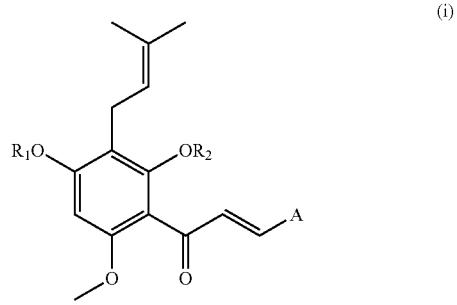

wherein:
$R_1$ and $R_2$ are independently selected from the group consisting of H; methyl; straight or branched alkyl from 2 to 10 carbon atoms; straight or branched alkyl from 2 to 10 carbon atoms containing 1 or 2 insaturations; cycloalkyl from 4 to 6 carbon atoms; cycloalkyl from 4 to 6 carbon atoms containing 1 or 2 insaturations; alkoxyalkyl selected from the group consisting of CH$_3$OCH$_2$—, CH$_3$OCH$_2$CH$_2$— or CH$_3$(OCH$_2$CH$_2$)$_n$—, CH$_3$(NHCH$_2$CH$_2$)$_n$—, CH$_3$(CH$_2$)$_n$CO(NHCH$_2$CH$_2$)$_n$—, CH$_3$(CH$_2$)$_n$SO$_2$(NHCH$_2$CH$_2$)$_n$—, HN(CH$_2$CH$_2$)$_2$N—(CH$_2$CH$_2$)$_n$—, CH$_3$N(CH$_2$CH$_2$)$_2$N—(CH$_2$CH$_2$)$_n$—, CH$_3$(CH$_2$)$_n$CO—N(CH$_2$CH$_2$)$_2$N—(CH$_2$CH$_2$)$_n$, CH$_3$(CH$_2$)$_n$SO$_2$—N(CH$_2$CH$_2$)$_2$N—(CH$_2$CH$_2$)$_n$—, O(CH$_2$CH$_2$)$_2$N—(CH$_2$CH$_2$)$_n$—; benzyl; benzyl optionally substituted in any of the free positions of the ring by 1 to 5 halogen atoms independently selected from the group consisting of F, Cl, Br, I; benzyl substituted with —NH$_2$, —NHCH$_3$, —NHCOCH$_3$, —NHCO-alkyl, —NHSO$_2$CH$_3$, —NHSO$_2$-alkyl, —SO$_2$CH$_3$, —SO$_2$-alkyl, —SO$_2$NHCH$_3$, —SO$_2$NHCO-alkyl, —NO$_2$, —OCH$_3$, —CO$_2$H, —CONHCH$_3$, —CONH-alkyl, —CO$_2$CH$_3$, —CO$_2$-alkyl, —CONHSO$_2$CH$_3$, —CONHSO$_2$—alkyl, alkyl being as defined above;
n is an integer ranging from 1 to 5;
A is a monocyclic or bicyclic aryl, or an aromatic or non-aromatic heterocyclic ring selected from the group consisting of pyrrole, pyrrolidine, 3-pyrroline, 2H-pyrrole, 2-pyrroline, indole, isoindole, 3H-indole, indolizine, indoline, carbazole, furan, benzofuran, isobenzofuran, 2H-pyran, 4H-pyran, benzo[b]thiophene, thiophene, pyridine, piperidine, 4H-quinolizine, isoquinoline, quinoline, tetrahydroquinoline, 1,8-naphthyridine, acridine, oxazole, isoxazole, benzoxazole, benzothiazole, isothiazole, thiazole, imidazole, 2-imidazole, imidazolidine, tetrazole, 1,2,3-triazole, 1,2,4-triazole, 1,2,3-oxadiazole, benzimidazole, purine, 1,4-dioxane, 1,3-dioxolane, 1,3-dithiane, 1,4-dithiane, 1,3,5-trithiane, morpholine, thiomorpholine, phenothiazine, pyrazole, 2-pyrazoline, pyrazolidine, quinazoline, cinnoline, pyrimidine, pyrazine, pteridine, phthalazine, 1,2,4-triazine, 1,3,5-triazine, pyridazine, piperazine, quinoxaline, phenazine, 1H-indazole,
wherein the substituents on ring A, independently from each other, are selected from the group consisting of H, —O-alkyl, —OCH$_3$, Cl, F, Br, I, —NO$_2$, —NH$_2$, —NHCH$_3$, —NH-alkyl, —NHCOCH$_3$, —NHCO-alkyl, —NHSO$_2$CH$_3$, —NHSO$_2$-alkyl, —SO$_2$CH$_3$, —SO$_2$-alkyl, —SO$_2$NH$_2$, —SO$_2$NHCH$_3$, —SO$_2$NH-alkyl, —SO$_2$NHCOCH$_3$, —SO$_2$NHCO-alkyl, —CO₂H, —CONHCH₃, —CONH-alkyl, —CO₂CH₃, —CO₂-alkyl, —CONHSO₂CH₃, —CONHSO₂-alkyl, alkyl being as defined above for R₁ and R₂; wherein at least one of the substituents on the A ring is H; provided that the compound of general formula (i) is not:
(E)-3-phenyl-1-(2,4,6-trimethoxy-3-(3-methylbut-2-enyl) phenyl)prop-2-en-1-one; or
(E)-3-phenyl-1-(2-hydroxy-4,6-dimethoxy-3-(3-methylbut-2-enyl)phenyl)prop-2-en-1-one;
tautomers, pharmaceutically acceptable salts and prodrugs thereof.

2. Compounds according to claim 1, wherein said aromatic or non-aromatic heterocyclic ring is benzofused and/or further substituted with halogen, alkyl, alkenyl, alkynyl, alkoxy, amino, amido, acylamido, sulphonamido, acyl, sulphonyl, aryl or heteroaryl.

3. Compounds according to claim 1, wherein when R₁ is H or R₂ is H, the isoprenyl group of general formula (i) forms a cycle with one of the oxygen atoms adjacent to it to give compounds of general formula (ii) or (iii)

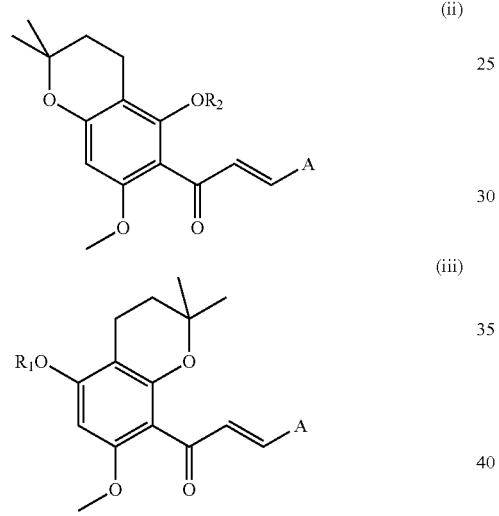

wherein R₁, R₂ are independently selected from the group consisting of H; methyl; straight or branched alkyl from 2 to 10 carbon atoms; straight or branched alkyl from 2 to 10 carbon atoms containing 1 or 2 insaturations; cycloalkyl from 4 to 6 carbon atoms; cycloalkyl from 4 to 6 carbon atoms containing 1 or 2 insaturations; alkoxyalkyl selected from the group consisting of CH₃OCH₂—, CH₃OCH₂CH₂— or CH₃(OCH₂CH₂)ₙ—, CH₃(NHCH₂CH₂)ₙ—, CH₃(CH₂)ₙCO(NHCH₂CH₂)ₙ—, CH₃(CH₂)ₙSO₂(NHCH₂CH₂)ₙ—, HN(CH₂CH₂)₂N—(CH₂CH₂)ₙ—, CH₃N(CH₂CH₂)₂N—(CH₂CH₂)ₙ—, CH₃(CH₂)ₙCO—N(CH₂CH₂)₂N—(CH₂CH₂)ₙ, CH₃(CH₂)ₙSO₂—N(CH₂CH₂)₂—N—(CH₂CH₂)ₙ—, O(CH₂CH₂)₂N—(CH₂CH₂)ₙ—; benzyl; benzyl optionally substituted in any of the free positions of the ring by 1 to 5 halogen atoms independently selected from the group consisting of F, Cl, Br, I; benzyl substituted with —NH₂, —NHCH₃, —NHCOCH₃, —NHCO-alkyl, —NHSO₂CH₃, —NHSO₂-alkyl, —SO₂CH₃, —SO₂-alkyl, —SO₂NHCH₃, —SO₂NHCO-alkyl, —NO₂, —OCH₃, —CO₂H, —CONHCH₃, —CONH-alkyl, —CO₂CH₃, —CO₂-alkyl, —CONHSO₂CH₃, —CONHSO₂-alkyl, alkyl being as defined above and A is a monocyclic or bicyclic aryl, or an aromatic or non-aromatic heterocyclic ring selected from the group consisting of pyrrole, pyrrolidine, 3-pyrroline, 2H-pyrrole, 2-pyrroline, indole, isoindole, 3H-indole, indolizine, indoline, carbazole, furan, benzofuran, isobenzofuran, 2H-pyran, 4H-pyran, benzo[b]thiophene, thiophene, pyridine, piperidine, 4H-quinolizine, isoquinoline, quinoline, tetrahydroquinoline, 1,8-naphthyridine, acridine, oxazole, isoxazole, benzoxazole, benzothiazole, isothiazole, thiazole, imidazole, 2-imidazole, imidazolidine, tetrazole, 1,2,3-triazole, 1,2,4-triazole, 1,2,3-oxadiazole, benzimidazole, purine, 1,4-dioxane, 1,3-dioxolane, 1,3-dithiane, 1,4-dithiane, 1,3,5-trithiane, morpholine, thiomorpholine, phenothiazine, pyrazole, 2-pyrazoline, pyrazolidine, quinazoline, cinnoline, pyrimidine, pyrazine, pteridine, phthalazine, 1,2,4-triazine, 1,3,5-triazine, pyridazine, piperazine, quinoxaline, phenazine, 1H-indazole, wherein the substituents on ring A, independently from each other, are selected from the group consisting of H, —O-alkyl, —OCH₃, Cl, F, Br, I, —NO₂, —NH₂, —NHCH₃, —NH-alkyl, —NHCOCH₃, —NHCO-alkyl, —NHSO₂CH₃, —NHSO₂-alkyl, —SO₂CH₃, —SO₂-alkyl, —SO₂NH₂, —SO₂NHCH₃, —SO₂NH-alkyl, —SO₂NHCOCH₃, —SO₂NHCO-alkyl, —CO₂H, —CONHCH₃, —CONH-alkyl, —CO₂CH₃, —CO₂-alkyl, —CONHSO₂CH₃, —CONHSO₂-alkyl, alkyl being as defined above for R₁ and R₂; wherein at least one of the substituents on the A ring is H.

4. Compounds according to claim 1 of general formula (iv):

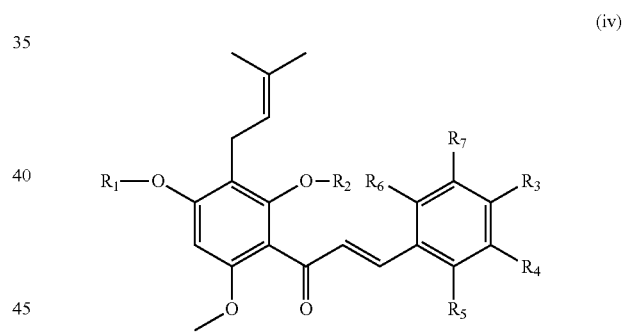

wherein R₁, R₂ are independently selected from the group consisting of H; methyl; straight or branched alkyl from 2 to 10 carbon atoms; straight or branched alkyl from 2 to 10 carbon atoms containing 1 or 2 insaturations; cycloalkyl from 4 to 6 carbon atoms; cycloalkyl from 4 to 6 carbon atoms containing 1 or 2 insaturations; alkoxyalkyl selected from the group consisting of CH₃OCH₂—, CH₃OCH₂CH₂— or CH₃(OCH₂CH₂)ₙ—, CH₃(NHCH₂CH₂)ₙ—, CH₃(CH₂)ₙCO(NHCH₂CH₂)ₙ—, CH₃(CH₂)ₙSO₂(NHCH₂CH₂)ₙ—, HN(CH₂CH₂)₂N—(CH₂CH₂)ₙ—, CH₃N(CH₂CH₂)₂N—(CH₂CH₂)ₙ—, CH₃(CH₂)ₙCO—N(CH₂CH₂)₂N—(CH₂CH₂)ₙ, CH₃(CH₂)ₙSO₂—N(CH₂CH₂)₂N—(CH₂CH₂)ₙ—, O(CH₂CH₂)₂N—(CH₂CH₂)ₙ—; benzyl; benzyl optionally substituted in any of the free positions of the ring by 1 to 5 halogen atoms independently selected from the group consisting of F, Cl, Br, I; benzyl substituted with —NH₂, —NHCH₃, —NHCOCH₃, —NHCO-alkyl, —NHSO₂CH₃, —NHSO₂-alkyl, —SO₂CH₃, —SO₂- alkyl, —SO₂NHCH₃, —SO₂NHCO-alkyl, —NO₂, —OCH₃, —CO₂H, —CONHCH₃, —CONH-alkyl, —CO₂CH₃, —CO₂-alkyl, —CONHSO₂CH₃, —CONHSO₂-alkyl, alkyl being as defined above and A is a monocyclic or bicyclic aryl, or an aromatic or non-aromatic heterocyclic ring selected from the group consisting of pyrrole, pyrrolidine, 3-pyrroline, 2H-pyrrole, 2-pyrroline, indole, isoindole, 3H-indole, indolizine, indoline, carbazole, furan, benzofuran, isobenzofuran, 2H-pyran, 4H-pyran, benzo[b]thiophene, thiophene, pyridine, piperidine, 4H-quinolizine, isoquinoline, quinoline, tetrahydroquinoline, 1,8-naphthyridine, acridine, oxazole, isoxazole, benzoxazole, benzothiazole, isothiazole, thiazole, imidazole, 2-imidazole, imidazolidine, tetrazole, 1,2,3-triazole, 1,2,4-triazole, 1,2,3-oxadiazole, benzimidazole, purine, 1,4-dioxane, 1,3-dioxolane, 1,3-dithiane, 1,4-dithiane, 1,3,5-trithiane, morpholine, thiomorpholine, phenothiazine, pyrazole, 2-pyrazoline, pyrazolidine, quinazoline, cinnoline, pyrimidine, pyrazine, pteridine, phthalazine, 1,2,4-triazine, 1,3,5-triazine, pyridazine, piperazine, quinoxaline, phenazine, 1H-indazole and R₃, R₄, R₅, R₆ and R₇, independently from each other, are selected from the group consisting of H, —O-alkyl, —OCH₃, Cl, F, Br, I, —NO₂, —NH₂, —NHCH₃, —NH-alkyl, —NHCOCH₃, —NHCO-alkyl, —NHSO₂CH₃, —NHSO₂-alkyl, —SO₂CH₃, —SO₂-alkyl, —SO₂NH₂, —SO₂NHCH₃, —SO₂NH-alkyl, —SO₂NHCOCH₃, —SO₂NHCO-alkyl, —CO₂H, —CONHCH₃, —CONH-alkyl, —CO₂CH₃, —CO₂-alkyl, —CONHSO₂CH₃, —CONHSO₂-alkyl, alkyl being as defined for R₁, R₂ as above, wherein at least one of R₃, R₄, R₅, R₆ and R₇ is H;

provided that when R₁ is methyl, R₃, R₄, R₅, R₆ and R₇ are H, and R₂ is not H or methyl.

5. Compounds according to claim 3, wherein when R₁ is H or R₂ is H, the isoprenyl group of general formula (iv) forms a cycle with one of the oxygen atoms adjacent to it to give compounds of general formula (v) or (vi):

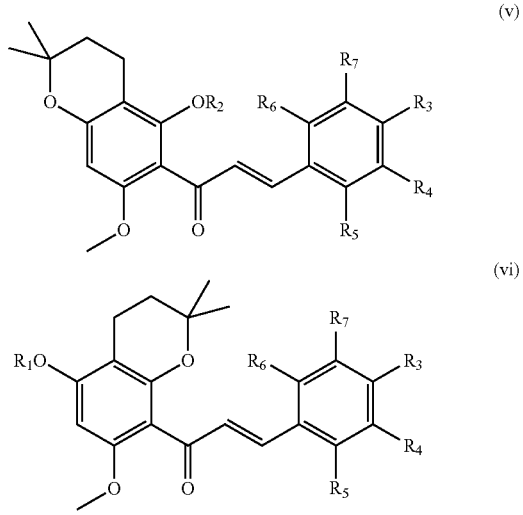

wherein R₁, R₂, are independently selected from the group consisting of H; methyl; straight or branched alkyl from 2 to 10 carbon atoms; straight or branched alkyl from 2 to 10 carbon atoms containing 1 or 2 insaturations; cycloalkyl from 4 to 6 carbon atoms; cycloalkyl from 4 to 6 carbon atoms containing 1 or 2 insaturations; alkoxyalkyl selected from the group consisting of CH₃OCH₂—, CH₃OCH₂CH₂— or CH₃(OCH₂CH₂)ₙ—, CH₃(NHCH₂CH₂)ₙ—, CH₃(CH₂)ₙCO(NHCH₂CH₂)ₙ—, CH₃(CH₂)ₙSO₂(NHCH₂CH₂)ₙ—, HN(CH₂CH₂)₂N—(CH₂CH₂)ₙ—, CH₃N(CH₂CH₂)₂N—(CH₂CH₂)ₙ—, CH₃(CH₂)ₙCO—N(CH₂CH₂)₂N—(CH₂CH₂)ₙ, CH₃(CH₂)ₙSO₂—N(CH₂CH₂)₂N—(CH2CH2n—, O(CH₂CH₂)₂N—(CH₂CH₂)ₙ—; benzyl; benzyl optionally substituted in any of the free positions of the ring by 1 to 5 halogen atoms independently selected from the group consisting of F, Cl, Br, I; benzyl substituted with —NH₂, —NHCH₃, —NHCOCH₃, —NHCO-alkyl, —NHSO₂CH₃, —NHSO₂-alkyl, —SO₂CH₃, —SO₂-alkyl, —SO₂NHCH₃, —SO₂NHCO-alkyl, —NO₂, —OCH₃, —CO₂H, —CONHCH₃, —CONH-alkyl, —CO₂CH₃, —CO₂-alkyl, —CONHSO₂CH₃, —CONHSO₂-alkyl, alkyl being as defined above and A is a monocyclic or bicyclic aryl, or an aromatic or non-aromatic heterocyclic ring selected from the group consisting of pyrrole, pyrrolidine, 3-pyrroline, 2H-pyrrole, 2-pyrroline, indole, isoindole, 3H-indole, indolizine, indoline, carbazole, furan, benzofuran, isobenzofuran, 2H-pyran, 4H-pyran, benzo[b]thiophene, thiophene, pyridine, piperidine, 4H-quinolizine, isoquinoline, quinoline, tetrahydroquinoline, 1,8-naphthyridine, acridine, oxazole, isoxazole, benzoxazole, benzothiazole, isothiazole, thiazole, imidazole, 2-imidazole, imidazolidine, tetrazole, 1,2,3-triazole, 1,2,4-triazole, 1,2,3-oxadiazole, benzimidazole, purine, 1,4-dioxane, 1,3-dioxolane, 1,3-dithiane, 1,4-dithiane, 1,3,5-trithiane, morpholine, thiomorpholine, phenothiazine, pyrazole, 2-pyrazoline, pyrazolidine, quinazoline, cinnoline, pyrimidine, pyrazine, pteridine, phthalazine, 1,2,4-triazine, 1,3,5-triazine, pyridazine, piperazine, quinoxaline, phenazine, 1H-indazole and R₃, R₄, R₅, R₆ and R₇, independently from each other, are selected from the group consisting of H, —O-alkyl, —OCH₃, Cl, F, Br, I, —NO₂, —NH₂, —NHCH₃, —NH— alkyl, —NHCOCH₃, —NHCO-alkyl, —NHSO₂CH₃, —NHSO₂-alkyl, —SO₂CH3, —SO₂-alkyl, —SO₂NH₂, —SO₂NHCH₃, —SO₂NH-alkyl, —SO₂NHCOCH₃, —SO₂NHCO-alkyl, —CO₂H, —CONHCH₃, —CONH-alkyl, —CO₂CH₃, —CO₂-alkyl, —CONHSO₂CH3, —CONHSO₂-alkyl, alkyl being as defined for R₁, R₂ above, wherein at least one of R₃, R₄, R₅, R₆ and R₇ is H.

6. Compounds according to claim 1, wherein A is a 2-, 3- or 4-pyridyl ring.

7. Compounds according to claim 1, wherein R₁ and R₂ are, independently from each other, hydrogen or methoxymethyl and the substituents on ring A or R₃, R₄, R₅, R₆ and R₇ are independently H, —OCH₃ fluorine, chlorine, —NO₂, —CONHCH₃, —SO₂NH₂, —NHSO₂CH₃, or the —SO₂NHCOCH(Et)NHCOOCH₂Ph group, wherein at least one of R₃, R₄, R₅, R₆ and R₇ is H.

8. Compound according to claim 1, selected from:
(E)-3-(3,4-dichloro-phenyl)-1-(6-methoxy-2,4-bis (methoxymethyloxy)-3-(3-methyl-but-2-enyl)phenyl) prop-2-en-1-one;
(E)-3-(3,4-dichloro-phenyl)-1-[2-hydroxy-6-methoxy-4-(methoxymethyloxy)-3-(3-methyl-but-2-enyl)-phenyl]-prop-2-en-1-one;
(E)-3-(3,4-dichloro-phenyl)-1-[2,4-dihydroxy-6-methoxy-3-(3-methyl-but-2-enyl)-phenyl]-prop-2-en-1-one;

(E)-3-(3,4-diclorophenyl)-1-(5-hydroxy-7-methoxy-2,2-dimethylchroman-6-yl)prop-2-en-1-one;
(E)-3-(4-fluorophenyl)-1-[6-methoxy-2,4-di-methoxymethyloxy-3-(3-methyl-but-2-enyl)-phenyl]-prop-2-en-1-one;
(E)-1-[2,4-dihydroxy-6-methoxy-3-(3-methyl-but-2-enyl)prenyl]-3-(4-fluorophenyl)-prop-2-en-1-one;
(E)-3-(4-fluorophenyl)-1-[2-hydroxy-6-methoxy-4-(methoxymethyloxy)-3-(3-methyl-but-2-enyl]-phenyl)prop-2-en-1-one;
(E)-1-[6-methoxy-2,4-dimethoxymethyloxy)-3-(3-methylbut-2-enyl)phenyl]-3-(4-nitrophenyl)prop-2-en-1-one;
(E)-1-[2-hydroxy-6-methoxy-4-(methoxymethyloxy)-3-(3-methylbut-2-enyl)phenyl]-3-(4-nitrophenyl)prop-2-en-1-one;
(E)-1[2,4-dihydroxy-6-methoxy-3-(3-methylbut-2-enyl)phenyl]-3-(4-nitrophenyl)prop-2-en-1-one;
(E)-N-(4-{3-[6-methoxy-2,4-bis-methoxymethyloxy-3-(3-methyl-but-2-enyl)phenyl]-3-(oxoprop-1-enyl}phenyl)-acetamide;
(E)-N-(4-{3-[2-hydroxy-6-methoxy-4-methoxymethyloxy-3-(3-methyl-but-2-enyl)phenyl]-3-oxoprop-1-enyl}phenyl)acetamide;
(E)-N-(4-{3-[2,4-dihydroxy-6-methyloxy-3-(3-methyl-but-2-enyl)phenyl]-3-oxoprop-1-enyl}-phenyl)acetamide;
(E)-3-(3,4-difluoro-phenyl)-1-[6-methoxy-2,4-bis-methoxymethyloxy-3-(3-methyl-but-2-enyl)phenyl]-prop-2-en-1-one;
(E)-3-(3,4-difluorophenyl)-1-[2-hydroxy-6-methoxy-4-methoxymethyloxy-3-(3-methyl-but-2-enyl)phenyl]prop-2-en-1-one;
(E)-3-(3,4-difluorophenyl)-1-[2,4-dihydroxy-6-methoxy-3-(3-methyl-but-2-enyl)-phenyl]-prop-2-en-1-one;
(E)-3-(2,4-difluoro-phenyl)-1-[6-methoxy-2,4-dimethoxymethyloxy-3-(3-methyl-but-2-enyl)phenyl]-prop-2-en-1-one;
(E)-3-(2,4-difluoro-phenyl)-1-[2-hydroxy-6-methoxy-4-methoxymethyloxy-3-(3-methyl-but-2-enyl)-phenyl]-prop-2-en-1-one;
(E)-3-(2,4-difluoro-phenyl)-1-[4-hydroxy-6-methoxy-2-methoxymethyloxy-3-(3-methyl-but-2-enyl)-phenyl]-prop-2-en-1-one;
(E)-3-(2,4-difluoro-phenyl)-1-[2,4-dihydroxy-6-methoxy-3-(3-methyl-but-2-enyl)-phenyl]-prop-2-en-1-one;
1-[6-methoxy-2,4-bis-methoxymethoxy-3-(3-methyl-but-2-enyl)-phenyl]-3-pyridin-2-yl-propenone;
1-[2-hydroxy-6-methoxy-4-methoxymethoxy-3-(3-methyl-but-2-enyl)-phenyl]-3-pyridin-2-yl-propenone hydrochloride;
1-[4-hydroxy-6-methoxy-2-methoxymethoxy-3-(3-methyl-but-2-enyl)-phenyl]-3-pyridin-2-yl-propenone hydrochloride;
1-[2,4-dihydroxy-6-methoxy-3-(3-methyl-but-2-enyl)-phenyl]-3-pyridin-2-yl-propenone hydrochloride;
3-(5-chloro-pyridin-3-yl)-1-[6-methoxy-2,4-bis-methoxymethoxy-3-(3-methyl-but-2-enyl)-phenyl]-propenone;
3-(5-chloro-pyridin-3-yl)-1-[2-hydroxy-6-methoxy-4-methoxymethloxy-3-(3-methyl-but-2-enyl)-phenyl]-propenone hydrochloride;
3-(5-chloro-pyridin-3-yl)-1-[4-hydroxy-6-methoxy-2-methoxymethoxy-3-(3-methyl-but-2-enyl)-phenyl]-propenone hydrochloride;
3-(5-chloro-pyridin-3-yl)-1-[2,4-dihydroxy-6-methoxy-3-(3-methyl-but-2-enyl)-phenyl]-propenone hydrochloride;
1-[6-methoxy-2,4-bis-methoxymethoxy-3-(3-methyl-but-2-enyl)-phenyl]-3-pyridin-4-yl-propenone;
1-[2-hydroxy-6-methoxy-4-methoxymethoxy-3-(3-methyl-but-2-enyl)-phenyl]-3-pyridin-4-yl-propenone hydrochloride;
1-[4-hydroxy-6-methoxy-2-methoxymethoxy-3-(3-methyl-but-2-enyl)-phenyl]-3-pyridin-4-yl-propenone hydrochloride;
1-[2,4-dihydroxy-6-methoxy-3-(3-methyl-but-2-enyl)-phenyl]-3-pyridin-4-yl-propenone hydrochloride;
N-(4-{3-[6-methoxy-2,4-bis-methoxymethoxy-3-(3-methyl-but-2-enyl)-phenyl]-3-oxo-propenyl}-phenyl)-methanesulphonamide;
N-(4-{3-[2-hydroxy-6-methoxy-4-methoxymethoxy-3-(3-methyl-but-2-enyl)-phenyl]-3-oxo-propenyl}-phenyl)-methanesulphonamide;
N-(4-{3-[4-hydroxy-6-methoxy-2-methoxymethoxy-3-(3-methyl-but-2-enyl)-phenyl]-3-oxo-propenyl}-phenyl)-methanesulphonamide;
N-(4-{3-[2,4-dihydroxy-6-methoxy-3-(3-methyl-but-2-enyl)-phenyl]-3-oxo-propenyl}-phenyl)-methanesulphonamide;
2-Chloro-5-{3-[2-hydroxy-6-methoxy-4-methoxymethoxy-3-(3-methyl-but-2-enyl)-phenyl]-3-oxo-propenyl}-benzenesulphonamide;
2-Chloro-5-{3-[4-hydroxy-6-methoxy-2-methoxymethoxy-3-(3-methyl-but-2-enyl)-phenyl]-3-oxo-propenyl}-benzenesulphonamide;
2-chloro-5-{3-[2,4-dihydroxy-6-methoxy-3-(3-methyl-but-2-enyl)-phenyl]-3-oxo-propenyl}-benzenesulphonamide;
2-chloro-5-{3-[6-methoxy-2,4-bis-methoxymethoxy-3-(3-methyl-but-2-enyl)-phenyl]-3-oxo-propenyl}-benzenesulphonamide;
2-chloro-5-[3-(5-hydroxy-7-methoxy-2,2-dimethyl-chroman-6-yl)-3-oxo-propenyl]-benzenesulphonamide.

9. Compound as claimed claim 1, selected from:
(E)-3-(2-fluorophenyl)-1-(6-methoxy-2-hydroxy-4-methoxymethoxy-3-(3-methylbut-2-enyl)phenyl)prop-2-en-1-one;
(E)-3-(2-fluorophenyl)-1-(6-methoxy-2,4-dihydroxy-3-(3-methylbut-2-enyl)phenyl)prop-2-en-1-one;
(E)-3-(3-fluoro-4-methoxyphenyl)-1-(6-methoxy-2,4-bis(methoxymethoxy)-3-(3-methylbut-2-enyl)phenyl)prop-2-en-1-one;
(E)-3-(3-fluoro-4-methoxyphenyl)-1-(6-methoxy-2-hydroxy-4-methoxymethoxy-3-(3-methylbut-2-enyl)phenyl)prop-2-en-1-one;
(E)-3-(3-fluoro-4-methoxyphenyl)-1-(6-methoxy-2,4-dihydroxy-3-(3-methylbut-2-enyl)phenyl)prop-2-en-1-one;
(E)-3-(2-fluoro-4-methoxyphenyl)-1-(6-methoxy-2,4-bis(methoxymethoxy)-3-(3-methylbut-2-enyl)phenyl)prop-2-en-1-one;
(E)-3-(2-fluoro-4-methoxyphenyl)-1-(6-methoxy-2-hydroxy-4-methoxymethoxy-3-(3-methylbut-2-enyl)phenyl)prop-2-en-1-one;
(E)-3-(2-fluoro-4-methoxyphenyl)-1-(6-methoxy-4-hydroxy-2-methoxymethoxy-3-(3-methylbut-2-enyl)phenyl)prop-2-en-1-one;
(E)-3-(2-fluoro-4-methoxyphenyl)-1-(6-methoxy-2,4-dihydroxy-3-(3-methylbut-2-enyl)phenyl)prop-2-en-1-one;

(E)-3-(4-nitrophenyl)-1-(6-methoxy-2-hydroxy-4-methoxymethoxy-3-(3-methylbut-2-enyl)phenyl)prop-2-en-1-one.

10. Method of treating tumours in subjects in need thereof, said methods comprising;
   administering an effective amount of compounds according to claim 1 to said subjects; and
   treating said tumours.

11. Methods of treating inflammatory, cardiovascular and neurodegenerative disorders in subjects in need thereof, said methods comprising;
   administering an effective amount of compounds according to claim 1 to said subjects; and
   treating said subjects.

12. Methods of treating disorders characterized by alteration of angiogenesis in patients in need thereof, said method comprising;
   administering an effective amount of compounds as claimed in claim 1 to said subjects; and
   treating said subjects.

13. Pharmaceutical composition comprising at least one compound according to claim 1 and at least one pharmaceutically acceptable excipient.

* * * * *